US009945761B2

(12) United States Patent
Celio

(10) Patent No.: US 9,945,761 B2
(45) Date of Patent: Apr. 17, 2018

(54) INTERFACE DESIGNED WITH DIFFERENTIAL PUMPING AND BUILT-IN FIGURE OF MERIT METHOD TO MONITOR CHAMBERS WHERE ENVIRONMENTALLY SENSITIVE SAMPLES ARE PREPARED AND TRANSFERRED FOR ANALYSIS

(71) Applicant: Board of Regents of the University of Texas System, Austin, TX (US)

(72) Inventor: Hugo Celio, Austin, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 447 days.

(21) Appl. No.: 14/445,650

(22) Filed: Jul. 29, 2014

(65) Prior Publication Data

US 2015/0037904 A1 Feb. 5, 2015

Related U.S. Application Data

(60) Provisional application No. 61/860,039, filed on Jul. 30, 2013.

(51) Int. Cl.
*G01N 1/00* (2006.01)
*G01N 1/28* (2006.01)
*H01J 49/04* (2006.01)
*H01J 37/18* (2006.01)

(52) U.S. Cl.
CPC ............ *G01N 1/28* (2013.01); *H01J 49/0495* (2013.01); *H01J 37/185* (2013.01); *Y10T 436/2575* (2015.01)

(58) Field of Classification Search
CPC ........................................................ G01N 1/28

USPC ........................................................ 436/180
See application file for complete search history.

(56) References Cited

U.S. PATENT DOCUMENTS

| 4,785,666 | A | 11/1988 | Bergquist |
| 5,164,593 | A | 11/1992 | Chapman et al. |
| 5,513,499 | A | 5/1996 | deRijke |

(Continued)

OTHER PUBLICATIONS

International Search Report and Written Opinion from PCT/US14/48585, dated Dec. 5, 2014, The University of Texas System Board of Regents, pp. 1-8.

(Continued)

*Primary Examiner* — Christine T Mui
*Assistant Examiner* — Emily R. Berkeley
(74) *Attorney, Agent, or Firm* — Meyertons, Hood, Kivlin, Kowert & Goetzel, P.C.

(57) ABSTRACT

In some embodiments, a system may function to transfer samples in a controlled environment. The system may include a sample container configured to convey a sample from a first device to a second device. The first device may be under pressure and the second device may be under vacuum. The second device may include a load chamber which functions to accept the sample from the sample container and a pump chamber coupled to the load chamber. The second device may include a high vacuum pump coupled to the pump chamber and a vacuum pump coupled to the pump chamber through the high vacuum pump in sequence. The second device may include an orifice sized to significantly restrict the flow of fluids through the conduit coupling the pump chamber to the load chamber, wherein the orifice is configured to allow for a transition from a viscous into a molecular flow.

13 Claims, 43 Drawing Sheets

(56) References Cited

U.S. PATENT DOCUMENTS 7,644,637 B2  1/2010  Moore et al.
8,366,370 B2  2/2013  Nakamura et al.

OTHER PUBLICATIONS

Gomlak et al. "Multipurpose high vacuum laser ablation/thin film deposition system" Rev. Sci. Instrum. 70, 3701 (1999), Abstract.
Goede et al. "A compact and flexible transfer cell for surface analysis" Meas. Sci. Technol. (1998) 9, 712, Abstract.
Firpo et al. High performance portable vacuum suitcase Rev. Sci. Instrum. 76, 026108 (2005).
Clausing et al. "Fifteen-centimeter-diameter UHV transfer system for remote plasma-wall interaction experiments" Journal of Vacuum Science and Technology; v. 17(3) p. 709-713, 1980.

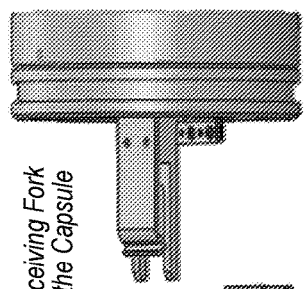
*Receiving Fork in the Capsule*
FIG. 6A
*Sample Bar*
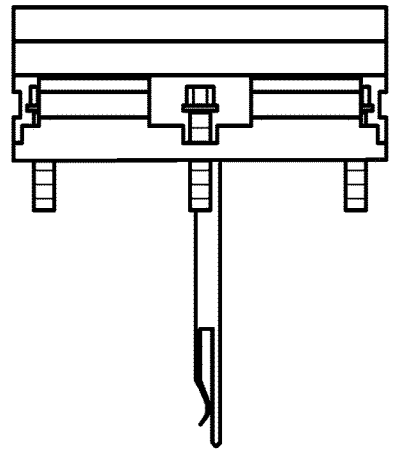
FIG. 6D
*Sample Bar holding, e.g., 25 samples (black squares) dimensions: l=0.5mm, w=0.5mm, and h=0.1mm*
FIG. 6C
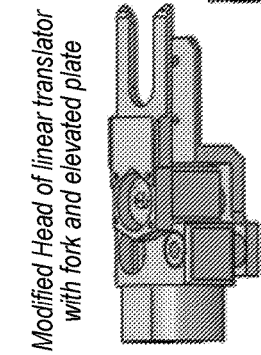
*Modified Head of linear translator with fork and elevated plate*
*Elevating Plate with Pin*
FIG. 6B
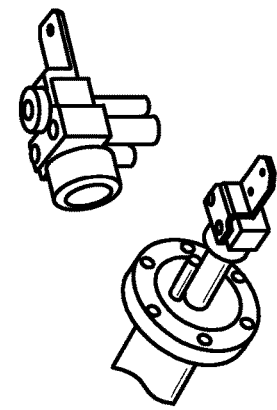
FIG. 6E

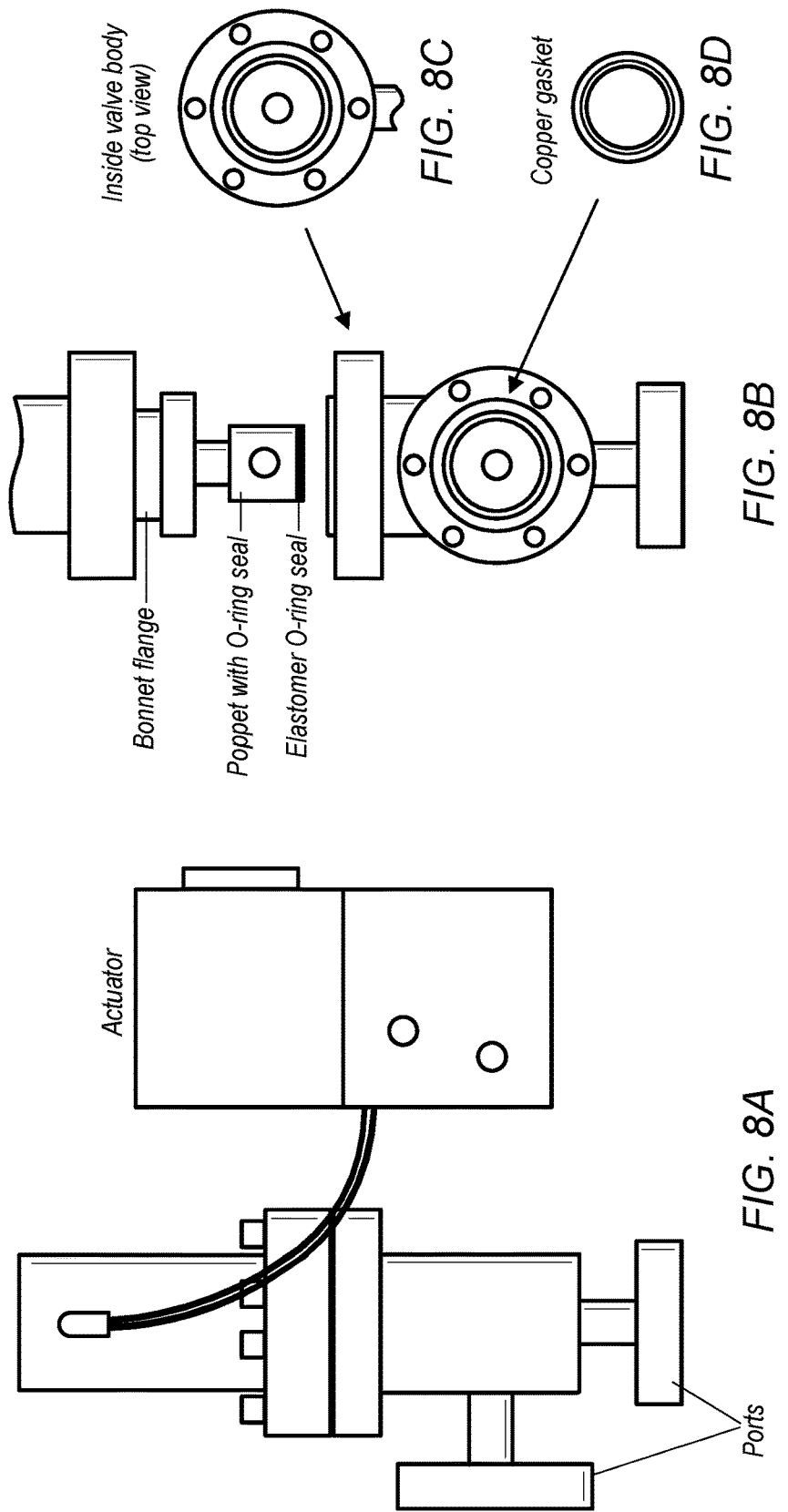

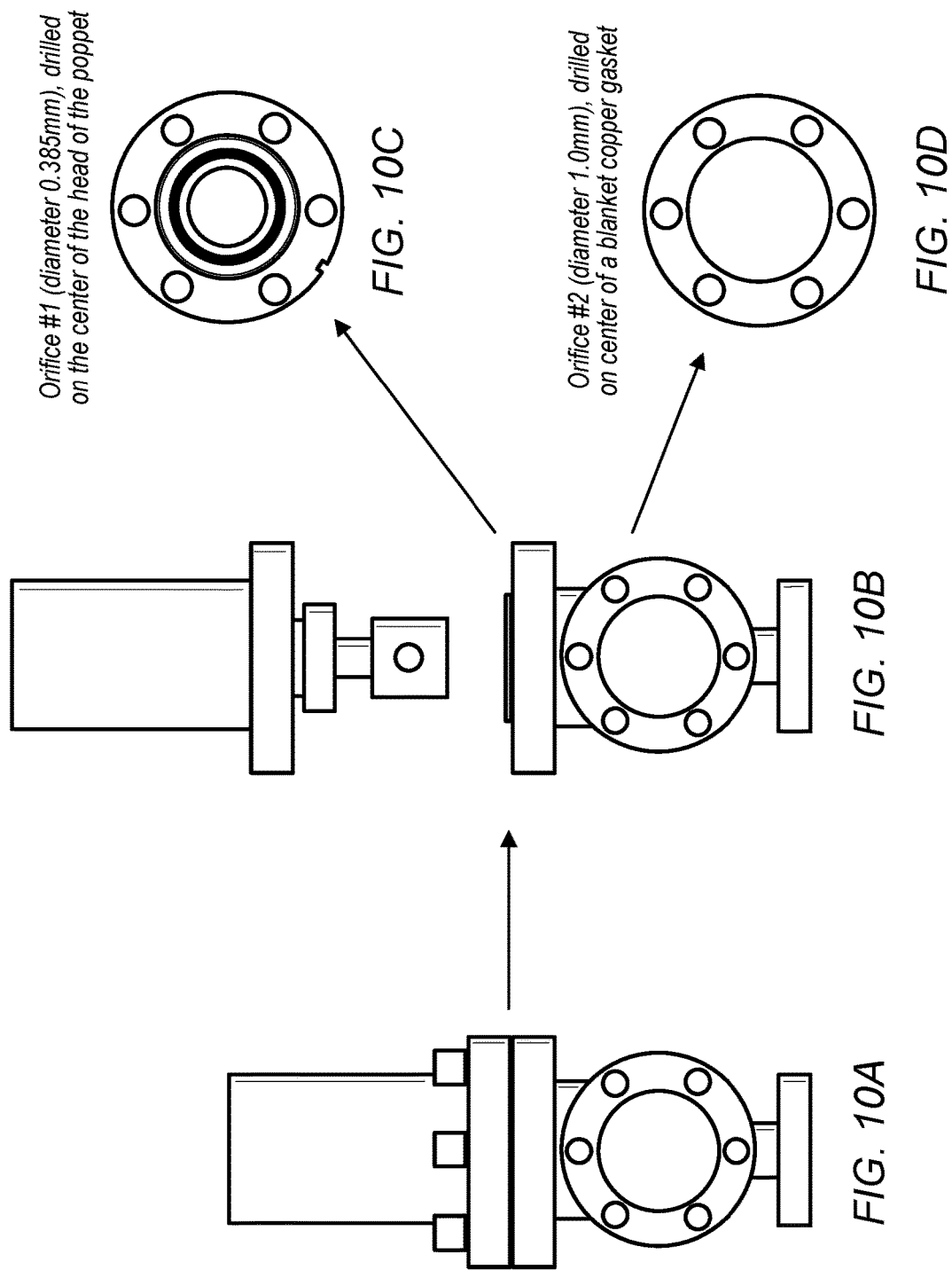

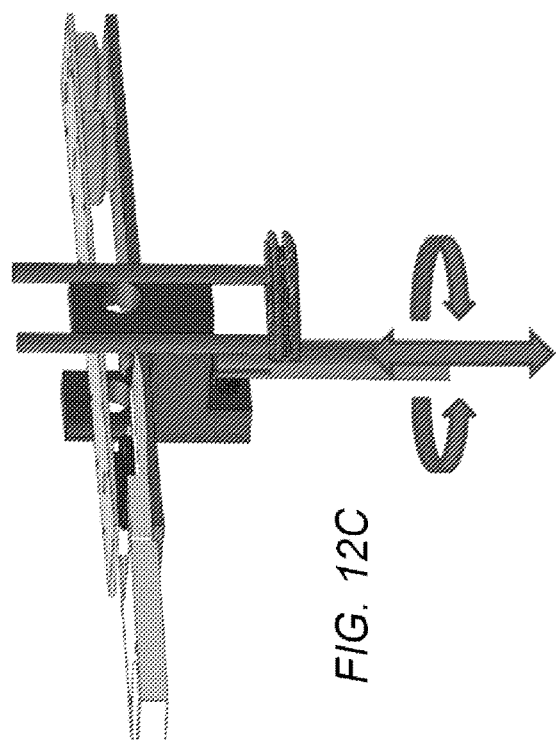
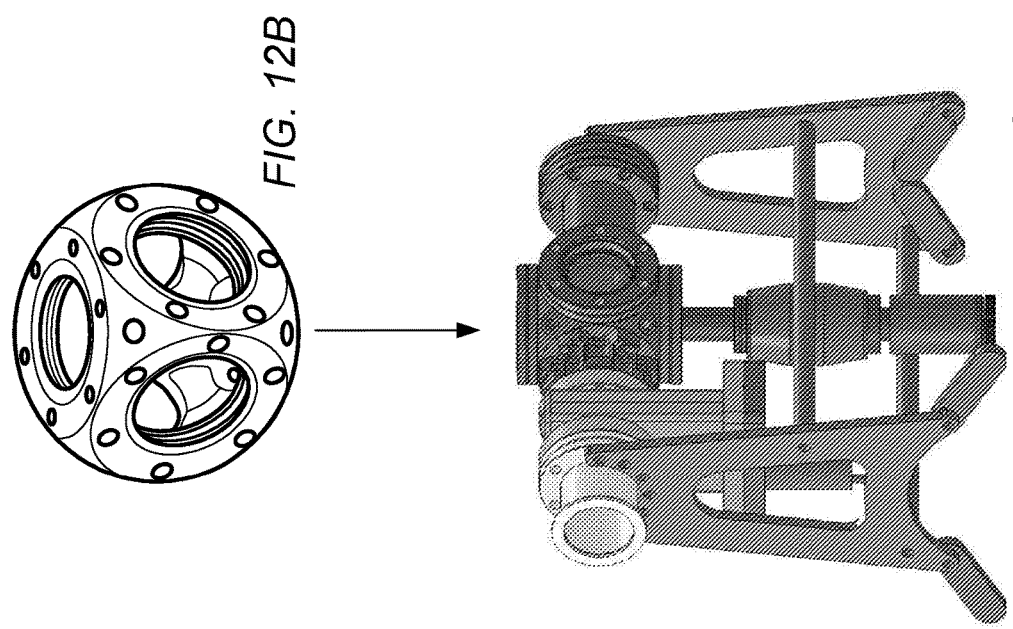
FIG. 12C
FIG. 12B
FIG. 12A

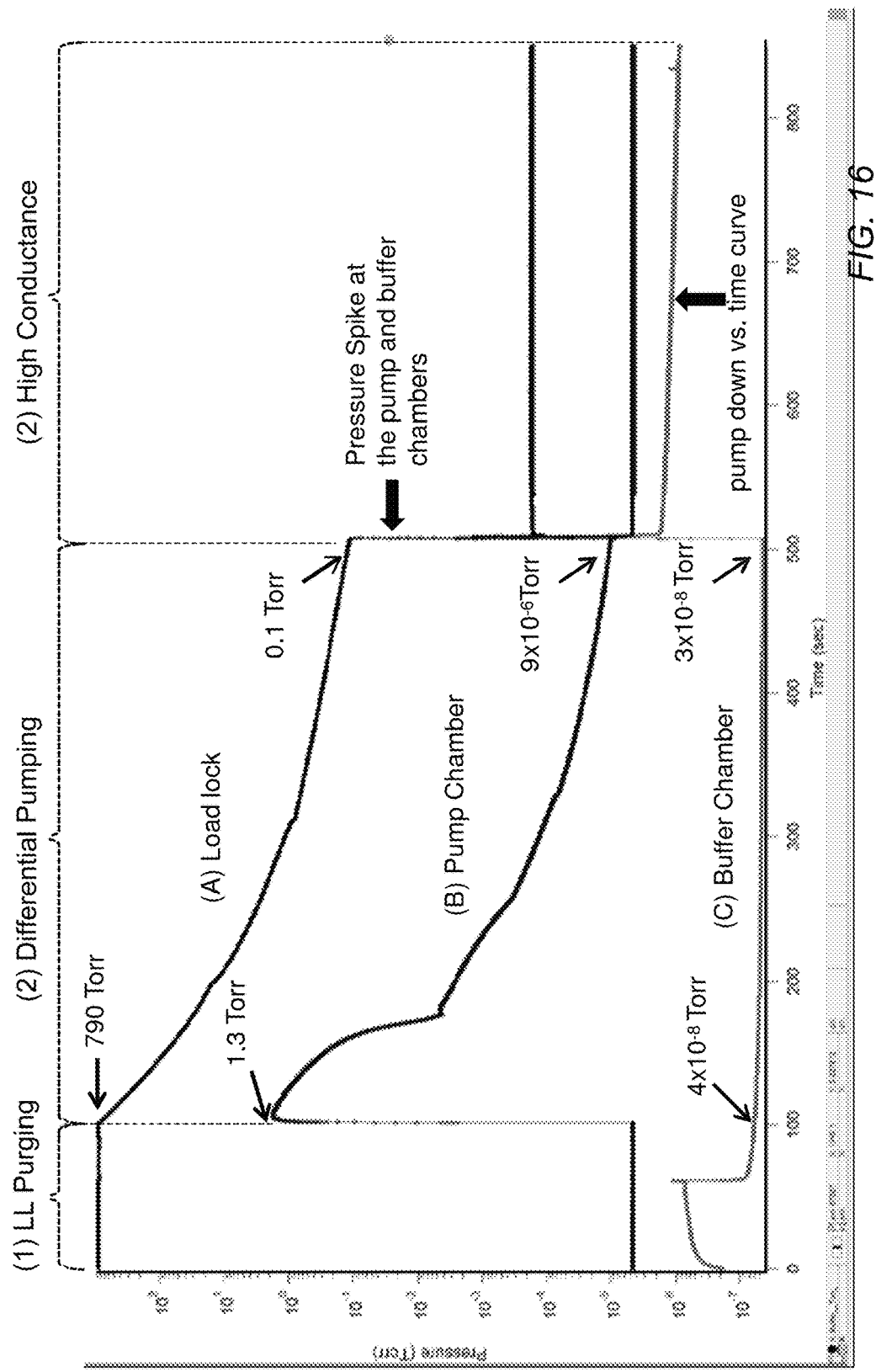

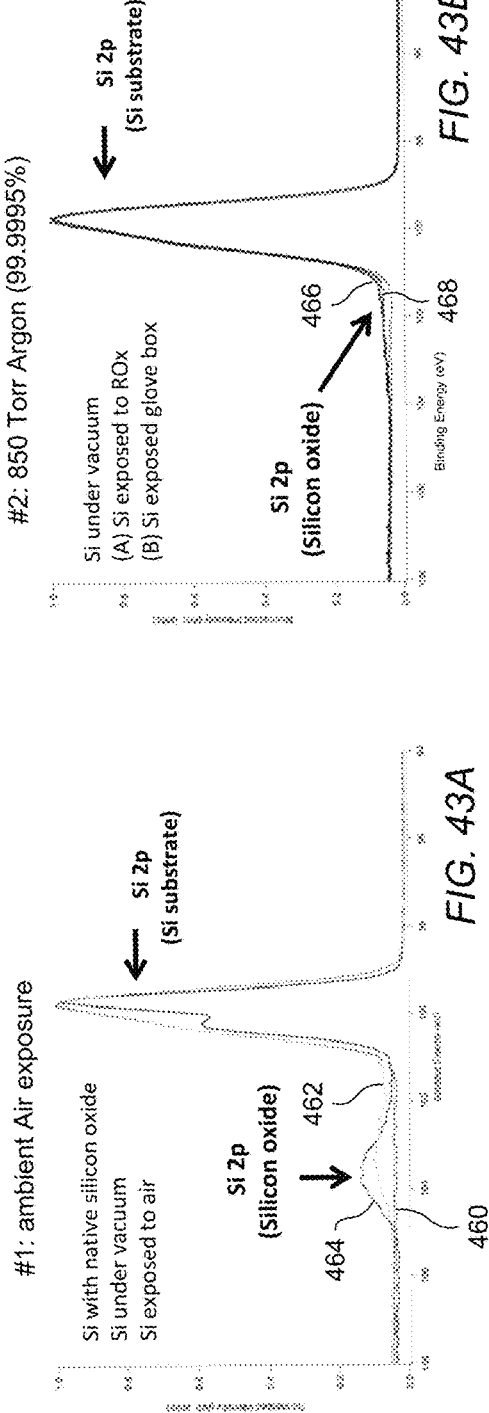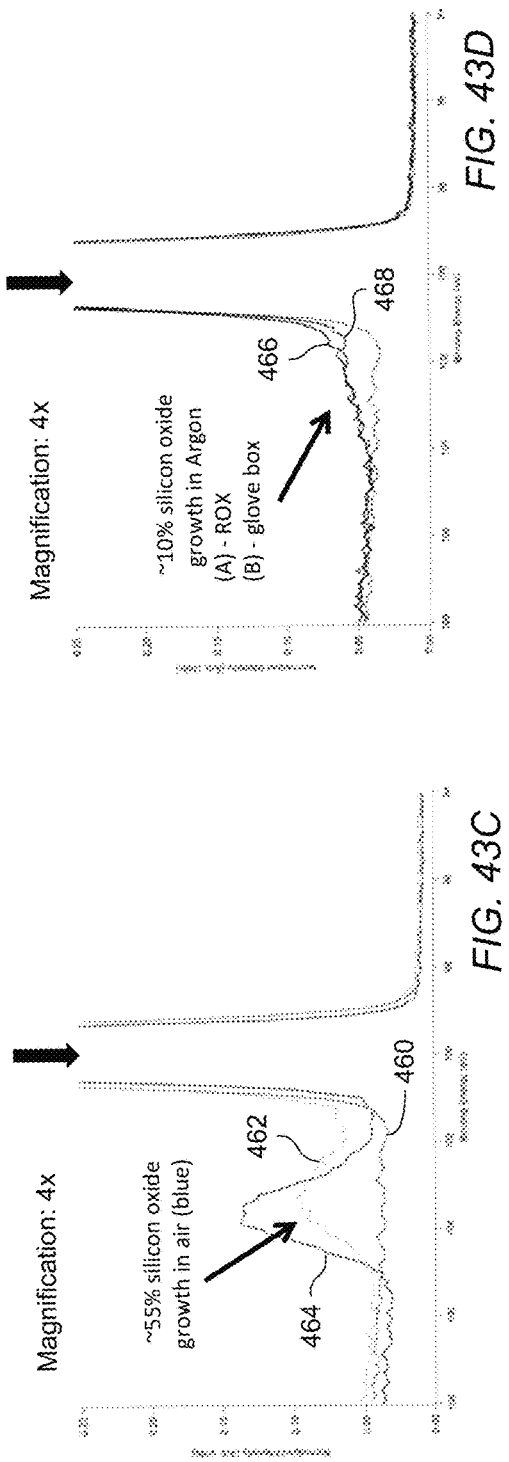

INTERFACE DESIGNED WITH DIFFERENTIAL PUMPING AND BUILT-IN FIGURE OF MERIT METHOD TO MONITOR CHAMBERS WHERE ENVIRONMENTALLY SENSITIVE SAMPLES ARE PREPARED AND TRANSFERRED FOR ANALYSIS

PRIORITY CLAIM

This application claims priority to U.S. Provisional Patent Application No. 61/860,039 entitled "INTERFACE DESIGNED WITH DIFFERENTIAL PUMPING AND BUILT-IN FIGURE OF MERIT METHOD TO MONITOR CHAMBERS WHERE ENVIRONMENTALLY SENSITIVE SAMPLES ARE PREPARED AND TRANSFERRED FOR ANALYSIS" to Celio filed on Jul. 30, 2013, all of which is incorporated by reference herein.

BACKGROUND OF THE INVENTION

1. Field of the Invention

The present disclosure generally relates to safely transferring sensitive materials. More particularly, the disclosure generally relates to systems and methods for facilitating the transfer of sensitive materials such that exposure to, for example, oxidants is reduced.

2. Description of the Relevant Art

Environmentally sensitive samples are typically transferred from an apparatus filled with an inert gas (e.g., a glove box filled with 99.9995% Argon) or from an ultra-high vacuum (UHV) chamber, into a UHV surface analysis chamber of interest. Transferring and loading environmentally sensitive samples from ambient pressure and into a UHV surface analysis chamber requires a transfer interface, applied as a load lock, with four key capabilities. These capabilities include (1) a sequence with inert gas purging, followed by a pump down to high vacuum, (2) pump down mechanism to transition from viscous to molecular flow regimes, (3) sample manipulation, and (4) software to carry out semiautomatic sequences for repeatability.

The sequence of the inert gas purge, followed by a pump down sequence is an important capability of a commercial load lock. This sequence begins with purging the load lock to displace air (mainly water and molecular oxygen to baseline levels), is followed by applying a positive flow of an inert gas for ~30 minutes, and is further followed by a pump down to UHV conditions. However, current commercial load locks and transfer interfaces do not have a quality control method to ensure a user that the load lock and other components are operating at working specifications, prior to loading samples into a load lock.

To obtain UHV conditions, a mechanism of differential pumping may be used. In general, differential pumping is a technique to generate a large difference in pressure between neighboring vacuum chambers, e.g., a load lock and pump chambers. This pressure difference is produced when these chambers are physically separated by a plate containing a small orifice while the pump chamber is under continuous vacuum pumping and its neighboring load lock chamber is under pressure, e.g., atmospheric pressure. This technique works because molecules in the pump chamber have a long free mean path (>1 meter) and randomly colliding against the chamber's wall. The latter condition is also known as the molecular flow, while molecules in the load lock under high pressure are traveling in a laminar flow.

Turbomolecular pumps have the widest operating pressure range of typical vacuum pumps and capable of crossing over from high vacuum (molecular flow, $p<10^{-4}$ Torr) to backing vacuum (Laminar flow, $p>1$ Torr (1.3 mbar)) and back to high vacuum without detrimental changes in pumping speed and/or throughput. The pump down mechanism to transition from a viscous to molecular flow regimes of commercial interfaces or load locks is typically based on a configuration where a turbomolecular (TM) pump is backed by a rough pump (e.g., a mechanical or dry pump). During the rough pumping, starting at atmospheric pressure (viscous flow), the TM is turned off or isolated and the gas load is re-routed directly into the rough pump. When the pressure drops to less than 0.1 Torr, the power of the TM pump is switched on to pump gas at the molecular flow regime. However, this configuration does not prevent additional exposure to oxidants exposure and/or hydrocarbon contamination, which can originate from roughing pumps during the transition from atmospheric pressure (viscous flow) to UHV conditions (molecular flow). Furthermore, currently available commercial load locks do not have a method for controlling the quality or reliability of the sample transfer.

Environmentally sensitive samples may be loaded into a sample transfer capsule for transitioning into and out of the load lock or transfer interface. However, current sample transfer capsules have many design flaws that may prevent a user from obtaining reliable and repeatable results. Current commercial designs lack the ability to evaluate leaks and/or back streaming generated during operation of the roughing pump. The sample transfer capsule may also be exposed to a pressure gap when the method for transitioning from ambient pressure to UHV is inefficient. In some examples, a single sample may be transported during each transfer event. This may lead directly to inter-sample variance, and current designs are not equipped with repeatability and reliability tests. Indeed, no "golden reference" has been developed to reliably evaluate and compare sample oxidation and contamination during the transfer process. The National Institute of Standards and Technology has never tested a method of transport for measurable kinetics of oxidation, and no prior art discloses methods or systems to reliably calibrate samples during differential pumping.

SUMMARY

To target at least the above issues a system and methods were developed for reliable sample transfer. In some embodiments, a system may function to transfer samples in a controlled environment. The system may include a sample container configured to convey a sample from a first device to a second device. The first device may be under pressure and the second device may be under vacuum. The second device may include a load chamber which functions to accept the sample from the sample container. The second device may include a pump chamber coupled to the load chamber using a conduit such that the pump chamber is in fluid communication with the load chamber as required. The second device may include a high vacuum pump coupled to the pump chamber. The second device may include a vacuum pump coupled to the pump chamber through the high vacuum pump in sequence. The second device may include an orifice sized to significantly restrict the flow of fluids through the conduit coupling the pump chamber to the load chamber, wherein the orifice is configured to allow for a transition from a viscous into a molecular flow.

A system and methods were developed for reliable sample transfer referred to herein as ROx or nanoROx are described. NanoROx was designed and constructed with primarily off-the-shelf UHV components and may be installed either as transfer interface (coupled to an existing load lock of a surface analysis chamber) or as a load lock coupled directly on a chamber of the surface analysis instrument of interest. NanoROx may operate with differential pumping via an orifice (or with multiple orifices in a series, or a variable aperture) while directing the viscous flow of gases directly into a turbomolecular pump, but not through its own roughing pump. This pump down mechanism allows the transition from viscous into molecular flow, without a power interruption (or isolation) of the turbomolecular pump. This pumping mechanism may prevent back-streaming of oxidants and hydrocarbon contamination from the roughing pump, particularly, during the transition from viscous to molecular flow (high vacuum). The operation of differential pumping may be executed using a pneumatic valve that actuates the gas flow from a load lock from atmospheric pressure to 0.1 Torr (or another chosen set point), while a single 0.385 mm diameter orifice may modulate the gas throughput from the load lock to the TM pump.

NanoROx may have a set of routines that may allow a user to generate a repeatable purge inert gas sequence, followed by pump down (via differential pumping as described above). Most notably, during the transition from viscous to molecular flow, the ROx may generate a tunable pressure spike (at viscous flow), followed by slower pressure pump down (at the molecular flow). The pressure spike and pump down may be recorded as a function of time, labeled as R1, and then repeated for a second time and labeled as R2. Using the pressure spike as a time reference peak from both of these curves, R1 and R2 may be overlapped while the slower pump down curves may have distinct pressure values at the molecular regime. Taking a ratio between R1 and R2, Ratio=(absolute(R1−R2))/R1, may yield a dimensionless 2-dimensional curve as a function of time and may be divided into divergence and convergence regions. The divergence region may be modeled using either a single or a sum of two exponential functions while the convergence region may be modeled either with a linear or single exponential function. The combined coefficients of these functions may allow a user to derive a set of FOMs for quality control with 6% repeatability (limited by the repeatability of the cold cathode gauge).

Furthermore, a user may evaluate the reliability of the entire transfer and loading process (i.e., glove box to surface analysis chamber) via a set of FOMs. One set may be derived from ROx itself and another set may be derived from apparatus filled with an inert gas (e.g., a glove box) where environmentally sensitive samples are synthesized or prepared. Both of these sets of FOMs may provide a range for quality control of the transfer and loading of samples to ensure that components of ROx are free of air leaks, hydrocarbon contaminants, and that the purity level of the purge/carrier gas is within specifications. In some embodiments, the FOM may test and evaluate contaminant specifications of an apparatus filled with an inert gas (e.g., a glove box) where environmentally sensitive materials are synthesized and/or handled prior to transfer. In some embodiments, a mass spectrometer may be incorporated into ROx as an independent instrument to quantify the figure of merits of the ROx.

Finally, once NanoROx checks and meets sample transfer specifications of an application, sample manipulation may be carried with linear and rational translators. The head of a commercial linear translator may be modified to retrieve a rectangular bar, which holds multiple samples, from a capsule coupled to the load lock. This retrieval may be based on a pull-lock mechanism, allowing line of sight manipulation of a bar with multiple samples. With this approach, a sample bar may be retrieved to an existing load lock or directly into the chamber of a surface analysis instrument. The present disclosure will be described in detail under the above areas.

In some embodiments, a system for transferring sample from ambient pressure to high vacuum may include a carrying capsule, a load lock, a buffer chamber, a pump chamber, and an inert gas reservoir. The Capsule may be coupled to the load lock chamber, with, for example, an easy to connect chain link and a metal-elastomer seal. The loadlock may be coupled to the pump chamber via a conduit and further coupled to an inert gas reservoir via a pneumatic valve and vent port with a long path coil via pneumatic valve. The buffer chamber may be coupled to the pump chamber via a pneumatic valve and furthermore to the sample analysis chamber ultra-high vacuum analysis chamber via a pneumatic valve. The pump chamber may have a high vacuum pump backed by a mechanical pump. The conduit may include a manual valve that is upstream from the orifice and a pneumatic valve. Furthermore, pressure gauges may be coupled to one or more of the buffer chamber, a loadlock, and/or a pump chamber. A mass spectrometer may be coupled to the buffer chamber.

The transferring of samples to a sample analysis chamber may include a linear translator and a rotational translator. The linear translator may include a two prong metal fork and an elevating plate including a pin. The elevating plate may function to elevate throughout the duration of the linear stroke. The linear translator may function to lock a sample bar into a conformation suitable for retrieving the sample bar from a capsule and delivering the sample bar to the sample analysis chamber. The sample bay may hold multiple samples that may be transferred during a single linear stroke. The capsule may include a receiving fork with a spring loaded plate to secure the sample bar during transport and for facilitating the transfer of the sample into and out of the capsule.

BRIEF DESCRIPTION OF THE DRAWINGS

Advantages of the present invention may become apparent to those skilled in the art with the benefit of the following detailed description of the preferred embodiments and upon reference to the accompanying drawings.

FIG. 6A depicts a diagram of components of a sample transfer capsule.

FIG. 6B depicts a diagram of an example head of a linear translator.

FIG. 6C depicts a diagram of an example sample bar.

FIG. 6D depicts a diagram of an example receiving fork.

FIG. 6E depicts a diagram of a commercially available linear translator.

FIG. 8A depicts a diagram of an example pneumatic angle valve assembly.

FIGS. 8B-D depict diagrams of components of an example pneumatic angle valve assembly.

FIGS. 10A-D depict perspective views of a pneumatic valve assembled with two orifices.

FIGS. 12A-C depict schematic diagrams of components of a sample transfer capsule.

FIG. 16 depicts an example plot of representative pressure vs. time curves during a differential pumping operation.

FIGS. 43A-D depict a set of plots depicting the oxidation of a crystalline silicon wafer.

Figure 1:
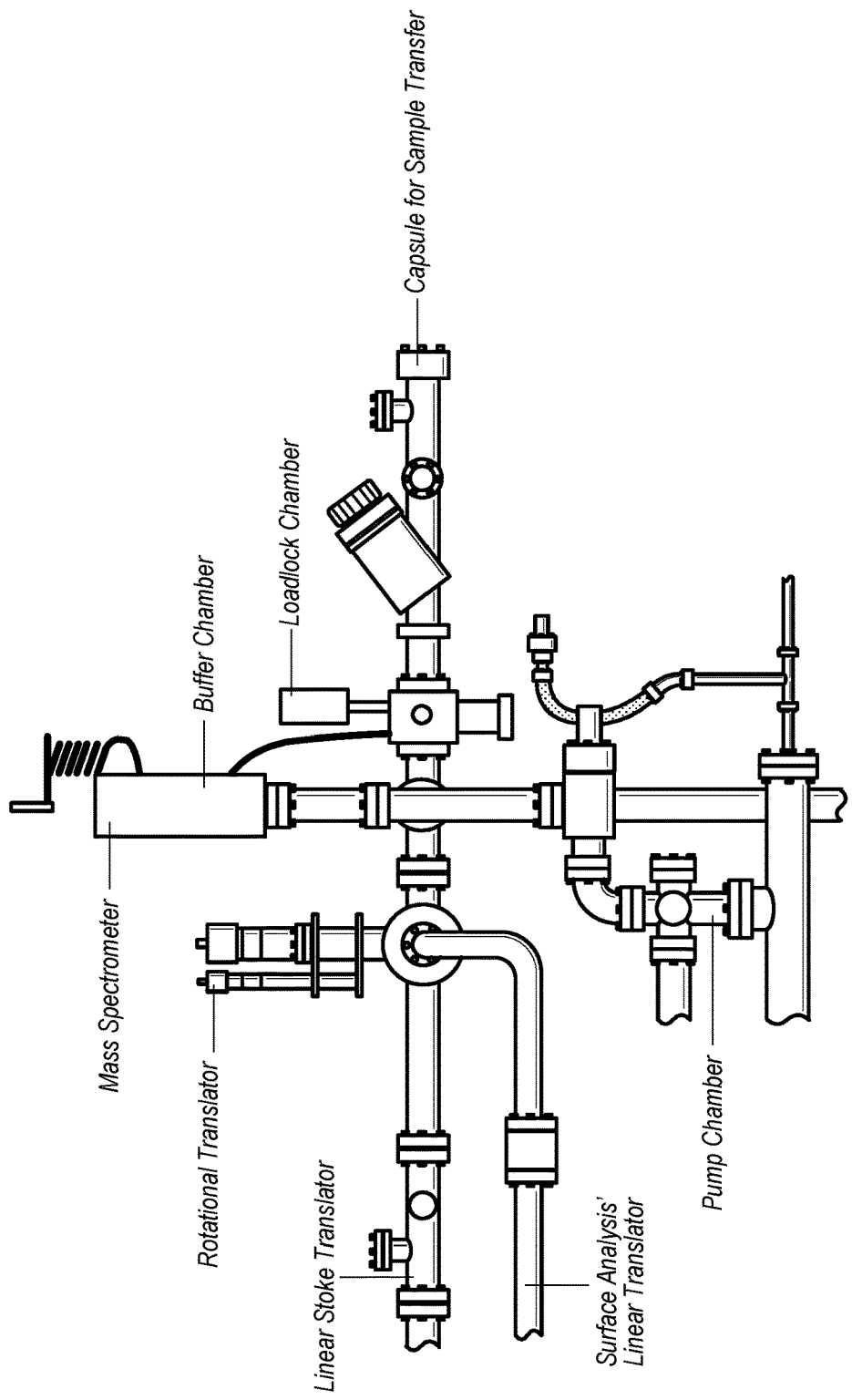
FIG. 1 depicts an example installation layout of an example nanoROx interface coupled to a load lock chamber of a UHV surface analysis chamber.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

In some embodiments, a system for transferring sample from ambient pressure to high vacuum may include a carrying capsule, a load lock, a buffer chamber, a pump chamber, and an inert gas reservoir. The Capsule may be coupled to the load lock chamber, with, for example, an easy to connect chain link and a metal-elastomer seal. The loadlock may be coupled to the pump chamber via a conduit and further coupled to an inert gas reservoir via a pneumatic valve and vent port with a long path coil via pneumatic valve. The buffer chamber may be coupled to the pump chamber via a pneumatic valve and furthermore to the sample analysis chamber ultra-high vacuum analysis chamber via a pneumatic valve. The pump chamber may have a high vacuum pump backed by a mechanical pump. The conduit may include a manual valve that is upstream from the orifice and a pneumatic valve. Furthermore, pressure gauges may be coupled to one or more of the buffer chamber, a loadlock, and/or a pump chamber. A mass spectrometer may be coupled to the buffer chamber.

The transferring of samples to a sample analysis chamber may include a linear translator and a rotational translator. The linear translator may include a two prong metal fork and an elevating plate including a pin. The elevating plate may function to elevate throughout the duration of the linear stroke. The linear translator may function to lock a sample bar into a conformation suitable for retrieving the sample bar from a capsule and delivering the sample bar to the sample analysis chamber. The sample bay may hold multiple samples that may be transferred during a single linear stroke. The capsule may include a receiving fork with a spring loaded plate to secure the sample bar during transport and for facilitating the transfer of the sample into and out of the capsule.

A goal of the system disclosed herein (referred to herein as ROx or nanoROx) is to reduce oxidation at the nano scale using differential pumping to transition from atmospheric pressure (viscous flow) to UHV conditions (molecular flow). In some embodiments, differential pumping may allow a user to acquire a repeatable and tunable pressure spike, followed by a pump down curve as a function of time. These 2-dimensional curves are analyzed and fitted to a plurality of functions with multiple coefficients. These coefficients are assigned as figures of merit (FOMs) and are applied as a quality control measure of the sample transfer reliability prior to loading samples into a surface analysis chamber under UHV. In combination with mass spectrometry analysis of gases, FOMs may be used to quantitatively evaluate if samples have or have not been exposed to oxidants and/or hydrocarbon contamination at levels above the specifications of an application. Thus, a user can evaluate the reliability of the entire transfer and loading process using a set of FOMs for each of the chambers of ROx (e.g., capsule, load lock, buffer, and pumping chamber), including an FOM for a glove box where environmentally samples were prepared under an inert environment.

FIG. 1 depicts an installation layout of an example nanoROx interface coupled to a load lock chamber of a UHV surface analysis chamber. In some embodiments, the interface may include a plurality of chambers, including a pump chamber, a load lock chamber and a buffer chamber. The pump chamber may include a turbomolecular pump. The interface may further include a capsule for sample transfer, as well as a linear stoke translator and a rotational translator. In this example, the linear stoke translator is 36 inches long, but may be longer or shorter depending on the parameters of the interface and analysis chamber. The capsule for sample transfer may be equipped with one or more manual valves configured to isolate samples during the transfer from one chamber to another. The linear stoke and rotational translators may be configured to manipulate and retrieve samples from the capsule, and may transfer samples to a linear translator coupled to the surface analysis chamber. The interface may include a mass spectrometer, which may be used for residual gas analysis. The turbomolecular pump may be configured to match vacuum conditions within the sample transfer capsule to the vacuum conditions of the load lock chamber.

Figure 2:
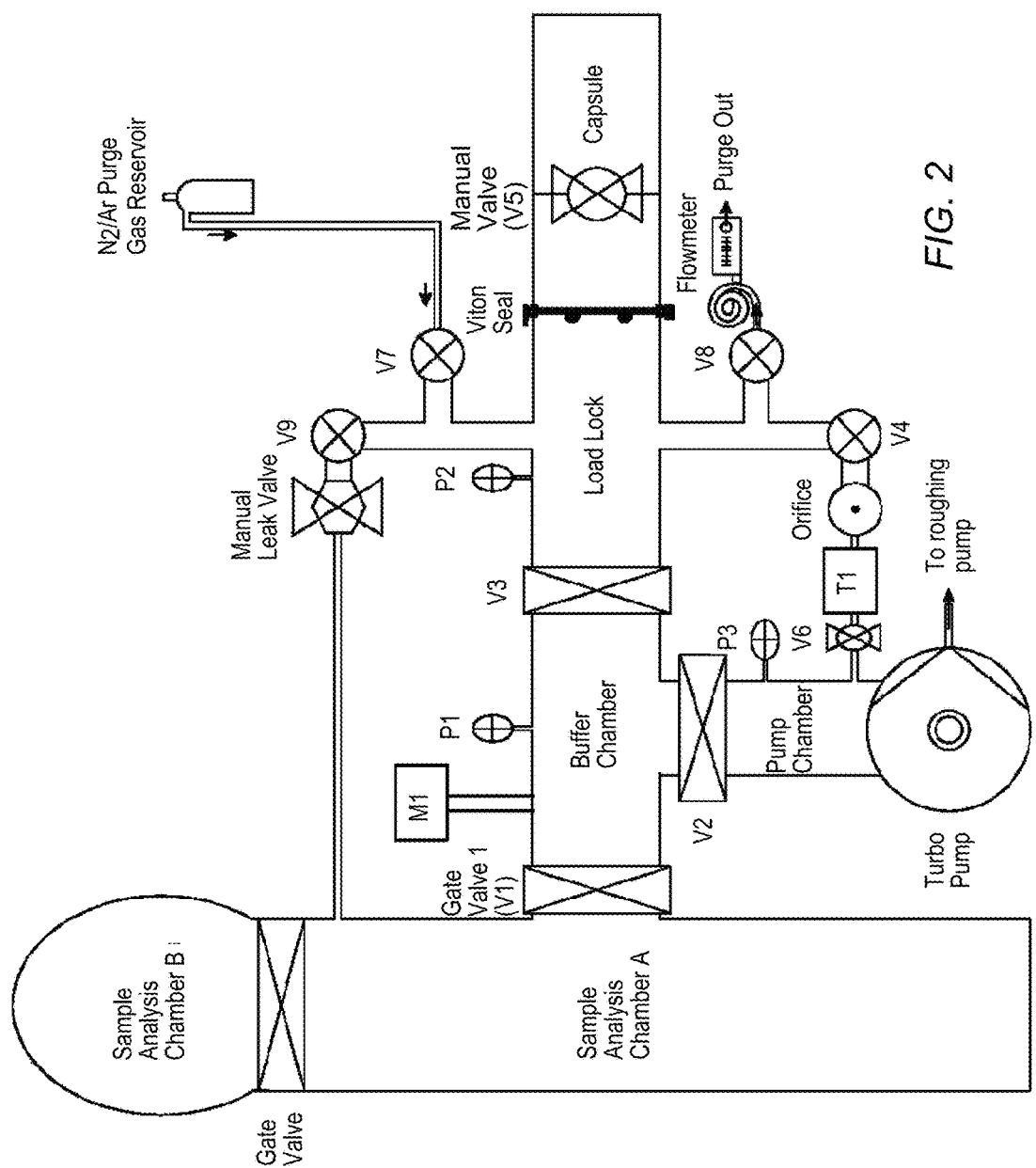
FIG. 2 depicts a schematic diagram of the ROx coupled to a surface analysis chamber under ultra-high vacuum.

FIG. 2 depicts a schematic diagram of the ROx coupled to a surface analysis chamber under ultra-high vacuum. In some embodiments, the sample transfer capsule may be coupled to a load lock chamber via a manual valve (V5) and a seal, such as a Viton seal. The load lock chamber may be coupled to a pressure gage (P2). The load lock chamber may be coupled to a buffer chamber via pneumatic valve V3. The buffer chamber may be coupled to a pressure gage (P1). The buffer chamber may be further coupled to sample analysis chamber A via pneumatic gate valve V1 and further coupled to a pump chamber via pneumatic valve V2. The pump chamber may be coupled to a pressure gauge (P3). The pump chamber may be coupled to a turbomolecular pump, which may be further coupled to a roughing pump. The pump chamber and load lock chamber may be coupled through a conduit. The conduit coupling the pump chamber and load lock chamber may include a manual valve (V6), a flexible metal tube (T1), an orifice and a pneumatic valve (V4). The conduit may be further connected to a purge outlet via a pneumatic valve (V8), a 1 meter long coil, and a flowmeter.

The load lock chamber may be coupled to a purge gas reservoir via a conduit which may include a pneumatic valve (V7). The purge gas reservoir may contain Nitrogen ($N_2$), Argon (Ar) or another inert gas. The reservoir may be kept under a controlled pressure. The load lock chamber may be further coupled to sample analysis chamber A via a conduit that includes a manual leak valve and a pneumatic valve (V9). Sample analysis chamber A may be coupled to sample analysis chamber B via a gate valve. A mass spectrometer (M1) may be coupled to the buffer chamber. The capsule chamber may be coupled to a glove box or other sample preparation chamber. A sample may thus pass from the glove box to the load lock chamber before entering the buffer chamber under UHV conditions, and eventually to the sample analysis chambers.

Within the interface, the overall base pressure may be set on the magnitude of $2\times10^{-8}$ Torr. Using the turbomolecular pump, the load lock chamber and capsule chamber may be pumped down from 850 Torr of inert gas to high vacuum, (on the order of $-2\times10^{-7}$ Torr), in less than 12 minutes.

A user may control the 7 pneumatic valves and read pressure from three gauges in a manual mode. This may be accomplished through instructions executed by a controller, for example a code written in Labview software. In a semiautomatic mode, a user can execute a code with subroutines to acquire a set of pressure peaks & pressure-vs.-time curve pump down curves. The total pump down time may be chosen by the user. The pump down curves may be used to extract figures of merit (FOM) in order to qualify sample transfer reliability.

Sample transfer reliability may include testing ROx and the chamber where the samples originated (e.g., a glove box) by using a set of figures of merit. For ROx and a glove box, for instance, they may be labeled as ROx-FOM and GB-FOM, respectively. These FOMS may form the basis for analyzing sample transfer reliability.

In combination with the FOMs described above, a mass spectrometer for residual gas analysis (RAG) may be integrated into the ROx to verify the pump down curves of ROx as well as to absolutely differentiate between oxidant exposure and outgassing of samples. Under 850 Torr of static inert gas, samples may be exposed to ~1 ppm $O_2$ and 1 ppm $H_2O$ during transport from glove box to the surface analysis chamber, or vice-versa. Levels of $O_2$ and $H_2O$ depend on the purity of the inert gas supply, and not on the design of ROx interface.

The capsule may be designed to carry a commercial sample bar, for example a Kratos sample bar with 12 samples per load (where sample size is ≤5 mm×≤5 mm×≤1 mm) during transfer. The capsule may transport solid and/or powder samples under 850 Torr of an inert gas (e.g., $N_2$ or Argon) or under vacuum.

The ROx interface may be installed as an interface on an existing load lock chamber of a surface analysis chamber or directly as a load lock on a surface analysis chamber. In the latter, ROx may be used to load both air sensitive or air stable samples directly into the surface analysis chamber.

Figure 3:
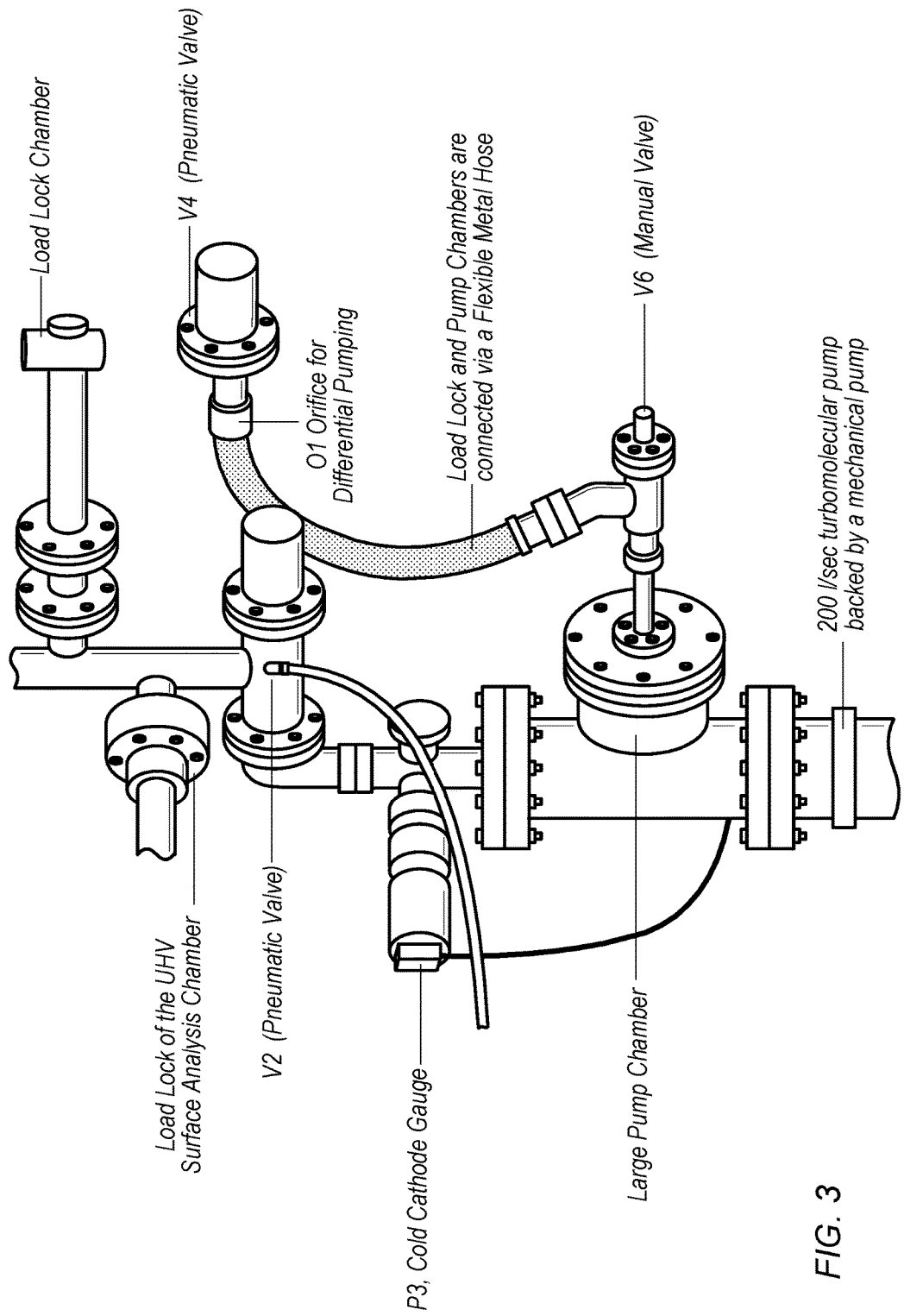
FIG. 3 depicts an example installation layout of a ROx pump chamber coupled to a load lock chamber.

FIG. 3 depicts an example installation layout of a ROx pump chamber coupled to a load lock chamber. The pump chamber may include a turbomolecular pump, which may be further coupled to a mechanical or roughing pump. In this example, the turbomolecular pump is configured to pump gas at a rate of 200 L/s. As shown in FIGS. 1 and 2 the pump chamber may be coupled to a buffer chamber. A pneumatic valve (V2) may be included between the pump chamber and buffer chamber such that valve V2 may control gas flow from the buffer chamber to the pump chamber. The pump chamber may be coupled to pressure gauge P3. In some examples, gauge P3 may be a cold cathode pressure gauge. Gauge P3 may be configured to measure pressures within a predetermined range of possible pump chamber pressures, for example from 600 Torr to $2\times10^{-9}$ Torr. The pump chamber may be further coupled to the load lock chamber via a conduit including manual valve V6.

The conduit coupling the pump chamber to the load lock chamber may be configured as a flexible metal hose (T1), which may comprise an orifice (O1) and a pneumatic valve (V4). Orifice O1 may be configured as two conflate flanges bolted against each other in a manner so as to press a copper gasket between the two flanges while connecting the load lock to the pump chamber. Pneumatic valve V4 may control gas flow from the load lock to orifice O1 and to the pump chamber during pump down events.

The pump chamber may allow ROx to be pumped independently from the UHV surface analysis chamber. The pump chamber may be engaged during the differential pumping of the load lock chamber, which may allow the pump chamber to transition from laminar flow to molecular flow without interruption while exclusively using the turbomolecular pump.

Figure 4B:
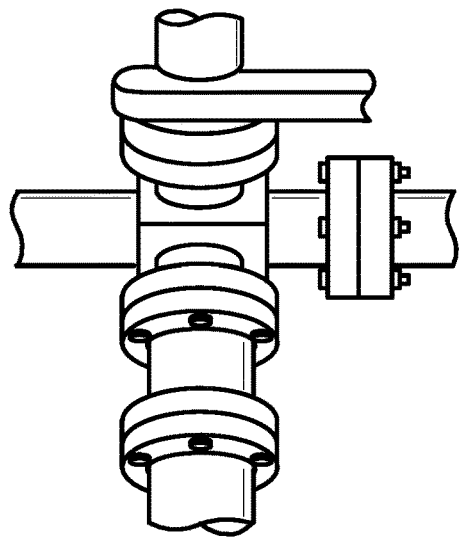
FIG. 4B depicts a side view of an example installation layout of a buffer chamber connecting to a pump chamber and a load lock chamber.
Figure 4A:
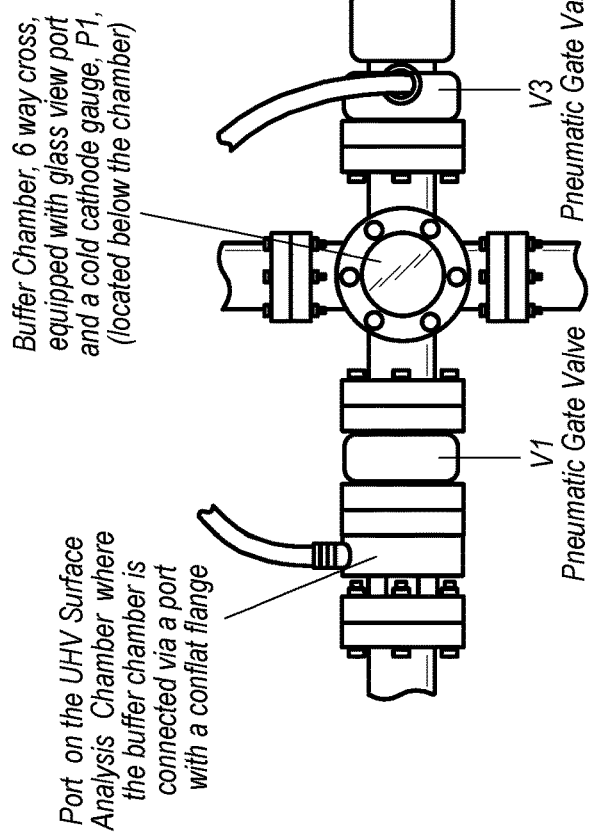
FIG. 4A depicts a top-down view of an example installation layout of a buffer chamber connecting to a pump chamber and a load lock chamber.

FIG. 4A depicts a top-down view of an example installation layout of a buffer chamber connecting to a pump chamber and a load lock chamber. FIG. 4B depicts a side view of the same example installation layout. In this example, the buffer chamber is a six-way chamber, equipped with a glass view port and a cold cathode pressure gauge (P1). The buffer chamber may be coupled to a UHV surface analysis chamber via a port including a conflat flange, and further coupled to a mass spectrometer.

The buffer chamber may include pneumatic valve V1, which may be configured to isolate the buffer chamber from the UHV surface analysis chamber. In some embodiments, the buffer chamber may include pneumatic valve V2, which may be configured to isolate the buffer chamber from the pump chamber, as described above in regards to FIGS. 2 and 3. In some embodiments, the buffer chamber may include pneumatic valve V3, which may be configured to isolate the buffer chamber form the load lock chamber.

The buffer chamber may be kept under the lowest vacuum level of the chambers included in the interface, for example a pressure on the order of $2 \times 10^{-8}$ Torr. This pressure may be maintained by intermittently using the turbomolecular pump included in the surface analysis chamber, and the turbomolecular pump included in the pump chamber. The cold cathode gauge, P1, may primarily be used to record the pressure spike and pressure-vs.-time pump down curves while masses for water and molecular oxygen are selected for the mass spectrometer. Both of these curves may be used to generate the figures of merit (FOM) to evaluate and qualify the reliability of sample transfer.

Figure 5C:
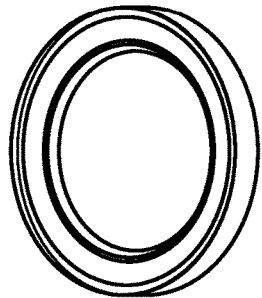
FIG. 5C depicts a diagram of an example elastomer seal.
Figure 5B:
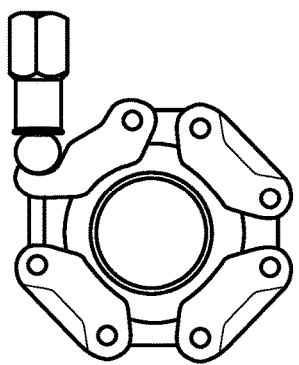
FIG. 5B depicts a diagram of an example chain clamp.
Figure 5A:
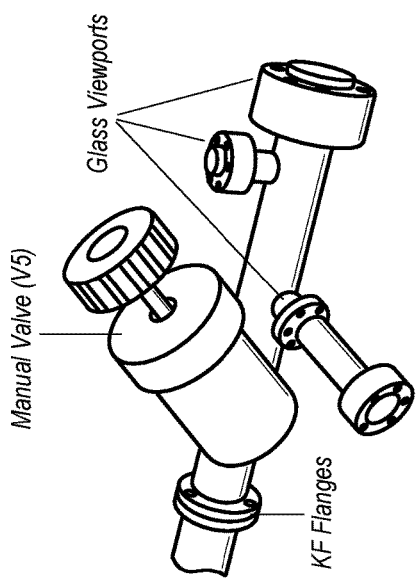
FIG. 5A depicts an example installation layout of a sample transfer capsule coupled to a load lock.
Figure 5D:
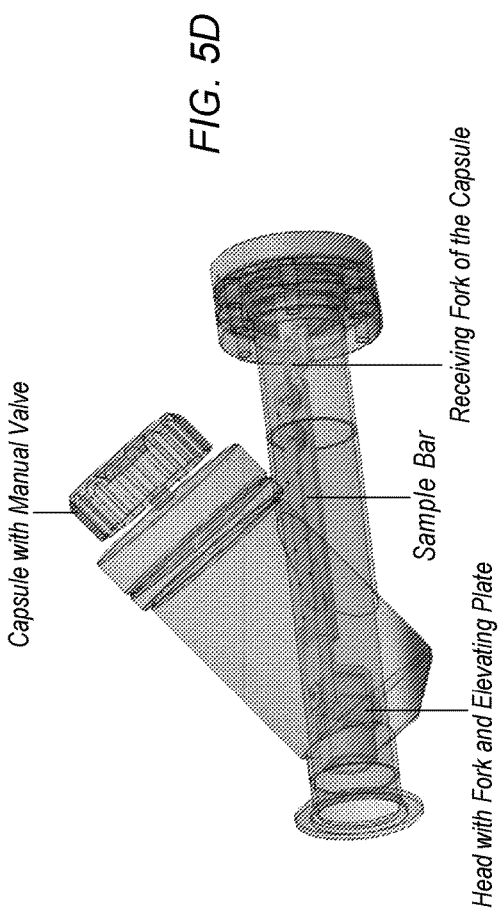
FIG. 5D depicts a schematic diagram of a sample transfer capsule.

FIG. 5A depicts an example installation layout of a sample transfer capsule coupled to a load lock. The capsule may be coupled to the load lock via manual valve V5 and further coupled to the load lock through KF flanges coupled to an EVAC chain clamp and an elastomer seal. FIG. 5B depicts a diagram of an example chain clamp. As depicted here, the chain clamp is configured as an EVAC chain clamp. The clamp may press two KF flanges together while in place. FIG. 5C depicts a diagram of an example elastomer seal. As depicted here, the seal is an NW40 seal including an aluminum outer ring and a Teflon inner ring. The elastomer seal may be used for multiple sample transfer applications and may be configured to seal under high vacuum conditions. FIG. 5D depicts a schematic diagram of a sample transfer capsule in accordance with the present disclosure. The capsule is shown with a manual valve, and may include a receiving fork. The receiving fork may facilitate transfer of a sample bar to a linear translator head that includes a fork and an elevating plate. Through the use of the KF flanges, an elastomer seal and an EVAC chain clamp, the sample capsule may be quickly connected to the load lock chamber of the interface.

FIG. 6A depicts a schematic diagram of components of a sample transfer capsule, including a receiving fork, sample bar and modified head of a linear translator. A diagram of a commercially available linear translator is shown for reference in FIG. 6E. The linear translator, for example, a linear translator with a 36 inch stroke, may include a head is configured to enable a plate to elevate for the duration of the stroke of the translator. The head may be modified to include a fork to facilitate transfer of the sample bar. FIG. 6B depicts a diagram of an example head of a linear translator modified to include a fork and pin. The fork and pin allow the head of the linear translator to lock onto the sample bar during transfer. The linear translator may thus be used either to retrieve a sample bar from the capsule or to load a sample bar into the capsule. FIG. 6C depicts a diagram of an example sample bar holding 25 samples, the samples having dimensions of l=0.5 mm, w=0.5 mm and h=0.1 mm. The sample bar may be used to transfer samples between chambers, including between UHV chambers. For example, the sample bar may be configured to transfer samples between a ToF-SEMS chamber and a Kratos XPS chamber, or vice-versa. FIG. 6D depicts a diagram of an example receiving fork. The receiving fork may be integrated into the sample chamber and may facilitate transfer of a sample bar to or from the head of the linear translator. FIG. 12A depicts a schematic diagram of a sample transfer capsule. FIG. 12B depicts a schematic diagram of a spherical chamber positionable in the depicted sample transfer capsule. FIG. 12C depicts a schematic diagram of an actuation control arm with 2 degrees of freedom. In some embodiments, actuation is provided by a control arm with two degrees of freedom. In some embodiments, rotation provides a locking mechanism. Rotation may provide yaw rotation to produce offset in the horizontal plane. Translation may provide vertical plane offset and enable removal of the stage interlocking mechanism once the carrier bar is handed off to the instrument translation arm.

Figures 7A, 7B:
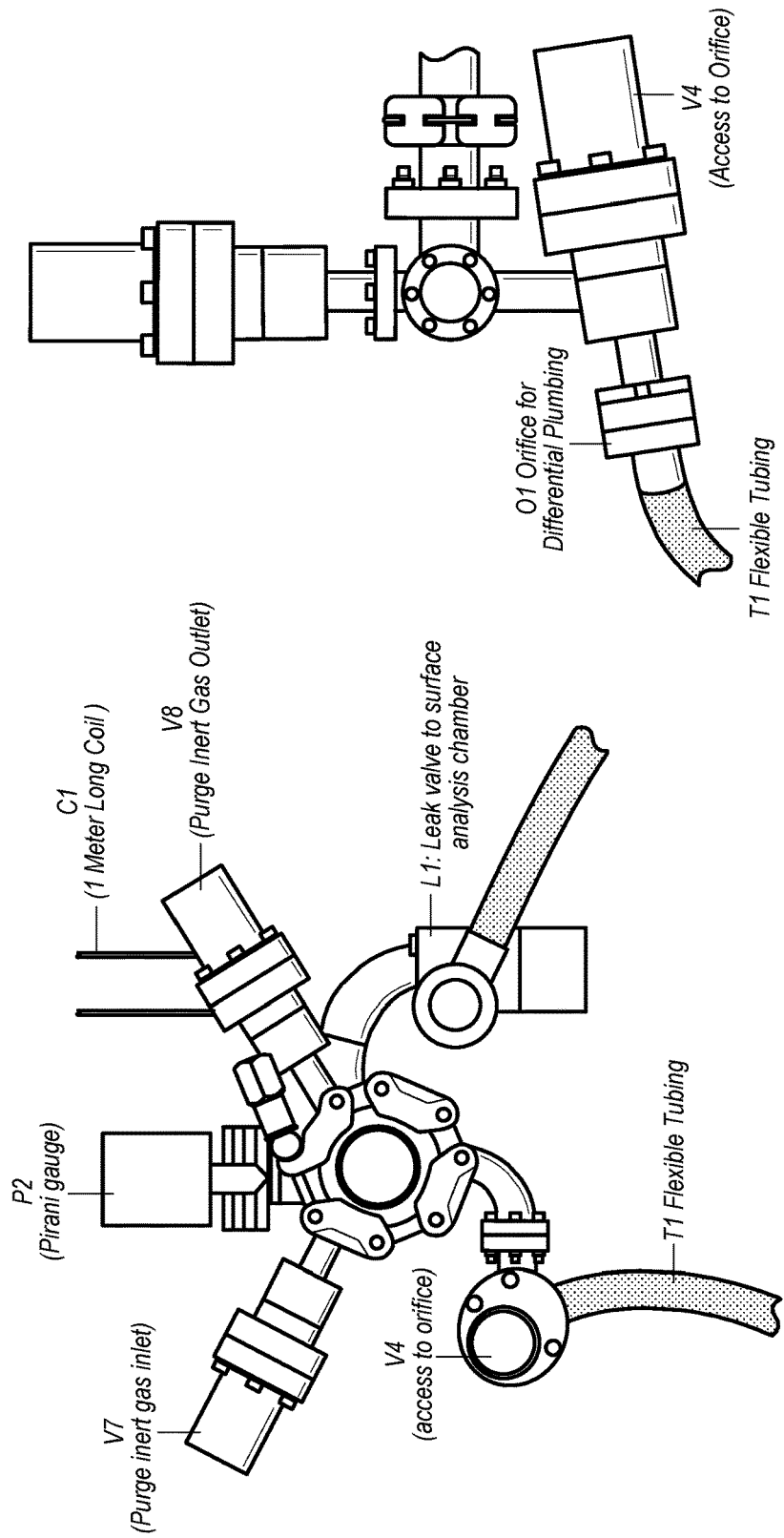
FIG. 7A depicts a front-view of an example installation layout of a load lock.
FIG. 7B depicts a side-view of an example installation layout of a load lock.

FIG. 7A depicts a front-view of an example installation layout of a load lock. In this example, the load lock includes a single orifice (O1) for differential pumping. FIG. 7B depicts a side-view of the example installation layout of a load lock as shown in FIG. 7A. The load lock chamber may include pressure gauge P2. Pressure gauge P2 may be a pirani pressure gauge, and may be configured to measure pressures within a predetermined range of possible pump chamber pressures, for example from $5 \times 10^{-4}$ Torr to 1000 Torr. The load lock chamber may include pneumatic valve V4. Pneumatic valve V4 may control gas flow leading to orifice O1. Orifice O1 may couple two conflat flanges: a first flange from pneumatic valve V4, and a second flange from flexible tube T1. The flanges may be bolted against each other to press a "blank" copper gasket, for example a gasket with a 0.385 mm diameter orifice at the center. The flanges may engage the copper gasket while connecting the load lock to the pump chamber.

The load lock chamber may include pneumatic valve V7. Pneumatic valve V7 may serve as an inlet and may control the flow of inert gas (e.g., Argon or Nitrogen) during purging. In some embodiments, the load lock chamber may include pneumatic valve V8. Pneumatic valve V8 may serve as an outlet and may control venting of the inert gas flow during purging. The load lock chamber may include metal coil C1. Metal coil C1 may be configured to increase the path length during purging. Metal coil C1 may minimize the quantity of air back streaming into load lock during purging of the load lock as well as when the purging stops, for example during the time period between the time point when V8 closes to the time point when V7 closes. The load lock chamber may include leak valve L1. Leak valve L1 may be used to control the gas flow from the load lock into the surface analysis chamber where a residual gas analyzer mass spectrometer may be housed.

FIG. 8A depicts a diagram of an example pneumatic angle valve assembly. The valve body may include two ports. Each port may include conflate flanges and may use copper gaskets as seals. The valve body may be coupled to an actuator connect to a power supply and configured to supply a constant rate of pressurized air, in response to commands from a controller. FIGS. 8B-D depict diagrams of components of an example pneumatic angle valve assembly. The assembly may include a bonnet flange, for example, a circular bonnet flange. The assembly may further include a poppet with an O-ring seal, for example an elastomer O-ring seal.

The configuration of the valve assembly may be regulated by the actuator. The actuator may provide power to the assembly via pressurized air. The pressurized air may be used to translate the valve's poppet up (port open) or down (port close). The poppet may be attached to the valve's body via a circular bonnet flange. The poppet has an O-ring seal to seal the valve's body ports. The valve body is a vacuum tight chamber that is flanged into a larger vacuum chamber via conflat flanges, for example 1.33" conflat flanges with copper gaskets.

Figure 9C:
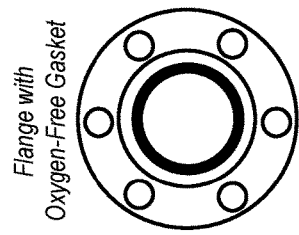
FIGS. 9C-E depict schematic diagrams of gas flow through a pneumatic angle valve assembly.
Figure 9D:
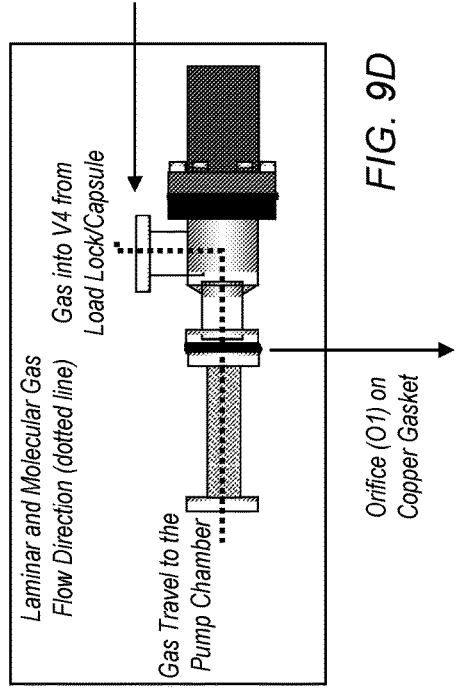
Figure 9E:
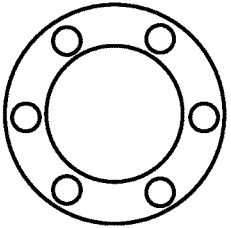
Figure 9B:
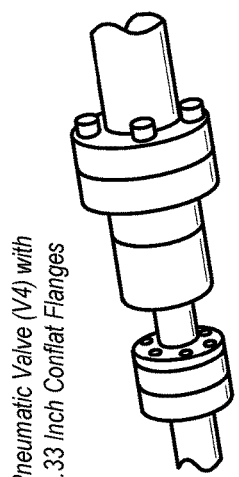
FIGS. 9A-B depict examples of installation layouts of a pneumatic angle valve assembly.
Figure 9A:
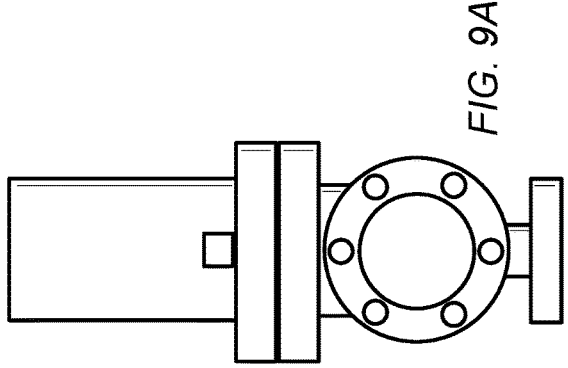

FIGS. 9A-B depict an example installation layout of a pneumatic angle valve assembly. Pneumatic valve V4 is shown with 1.33" conflate flanges with copper gaskets, and is shown coupled to a conduit between the pump chamber and the load lock chamber. FIGS. 9C-E depict a schematic diagram of gas flow through a pneumatic angle valve assembly. The valve assembly may include a flange with an oxygen-free gasket, for example a 1.5 cm diameter gasket. The valve assembly may further include Orifice O1. Orifice O1 may have diameter of 0.388 mm, and may be bored on the center of an oxygen-free gasket, for example a blank gasket with a thickness of 2.5 mm. The orifice may further be pressed between two conflate flanges to form an ultra-high vacuum seal. As represented by the dotted line in FIG. 9B, gas may enter valve V4 from the load lock or capsule, passing through a flange. Gas may subsequently pass through the orifice and travel out of the valve assembly and to the pump chamber. During differential pumping of gases in the load lock, the pneumatic valve may actuate the gas flow from load lock into V4 while the 0.385 mm diameter orifice modulates the gas throughput into the pump chamber.

FIGS. 10A-D depict perspective views of a pneumatic valve assembled with two orifices. In this example, the first orifice (O1) is drilled on the center of the head of the poppet valve. The second orifice (O2) in this example is drilled on the center of a blank copper gasket. In this example, the O1 has a diameter of 0.385 mm and O2 has a diameter of 1.0 mm. The diameter of the orifices may differ depending on the application and the size and configuration of the pneumatic valve. In general, the diameter of the second orifice may be larger than the diameter of the first orifice.

Figure 11:
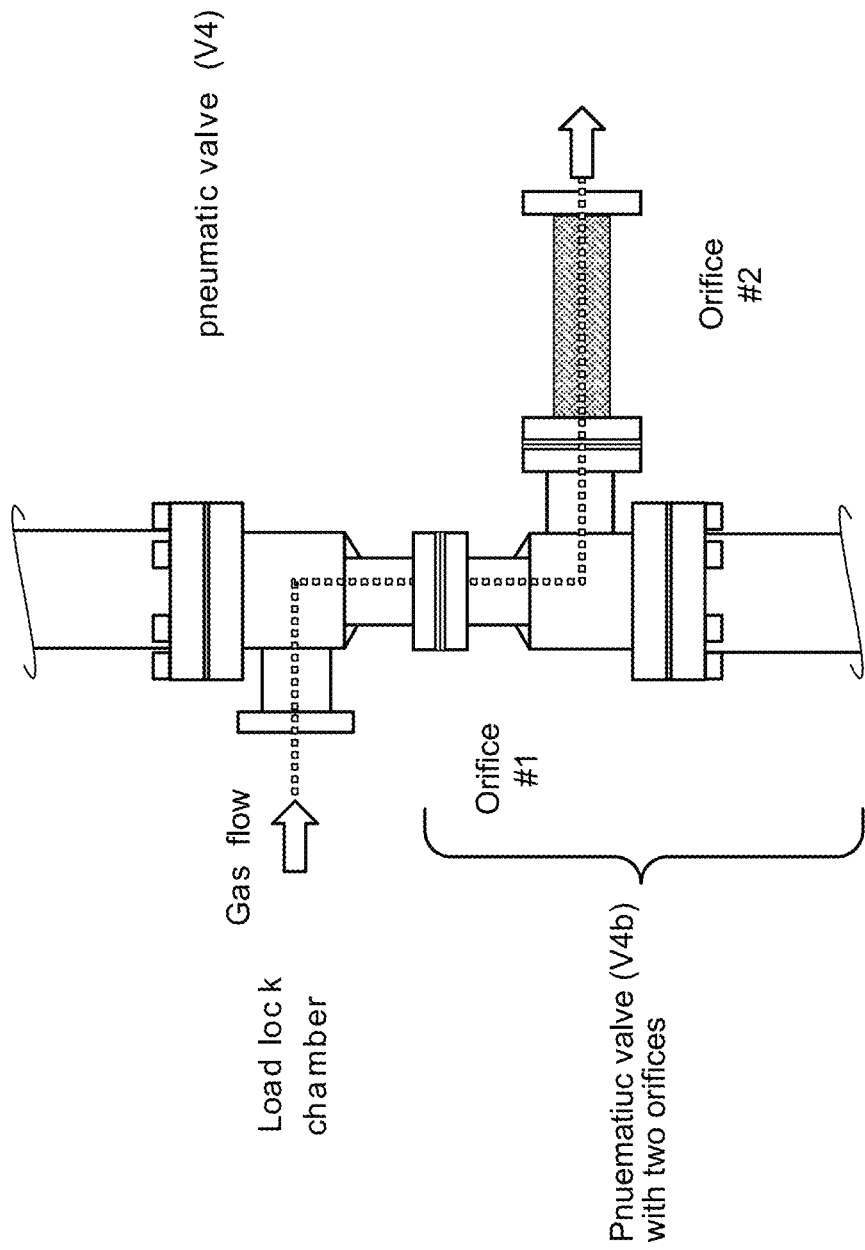
FIG. 11 depicts a schematic diagram of two angle valves in series.

FIG. 11 depicts a schematic diagram of two angle valves in series. In this example, pneumatic valve V4 is shown coupled to the load lock chamber. Pneumatic valve V4b is shown coupled to pneumatic valve V4 downstream of the load lock chamber. Pneumatic valve V4b is further coupled to the pump chamber. In this example, during differential pumping of gases in the load lock, the pneumatic valve (V4) may actuate the gas flow from the load lock into V4b, while Orifice #1 (0.385 mm diameter orifice) modulates the gas flow from atmospheric pressure to 0.1 Torr while V4b is in the close position. When the pressure drops below 0.1 Torr, V4b opens and Orifice #2 (1.0 mm diameter orifice) modulates gas throughput from 0.1 to 0.01 Torr into the pump chamber. The main function of the second orifice is to increase the throughput by a factor of three. Thus, the total time during differential pumping is reduced, while achieving lower pressures prior to the pressure spike and pump down.

Figure 13:
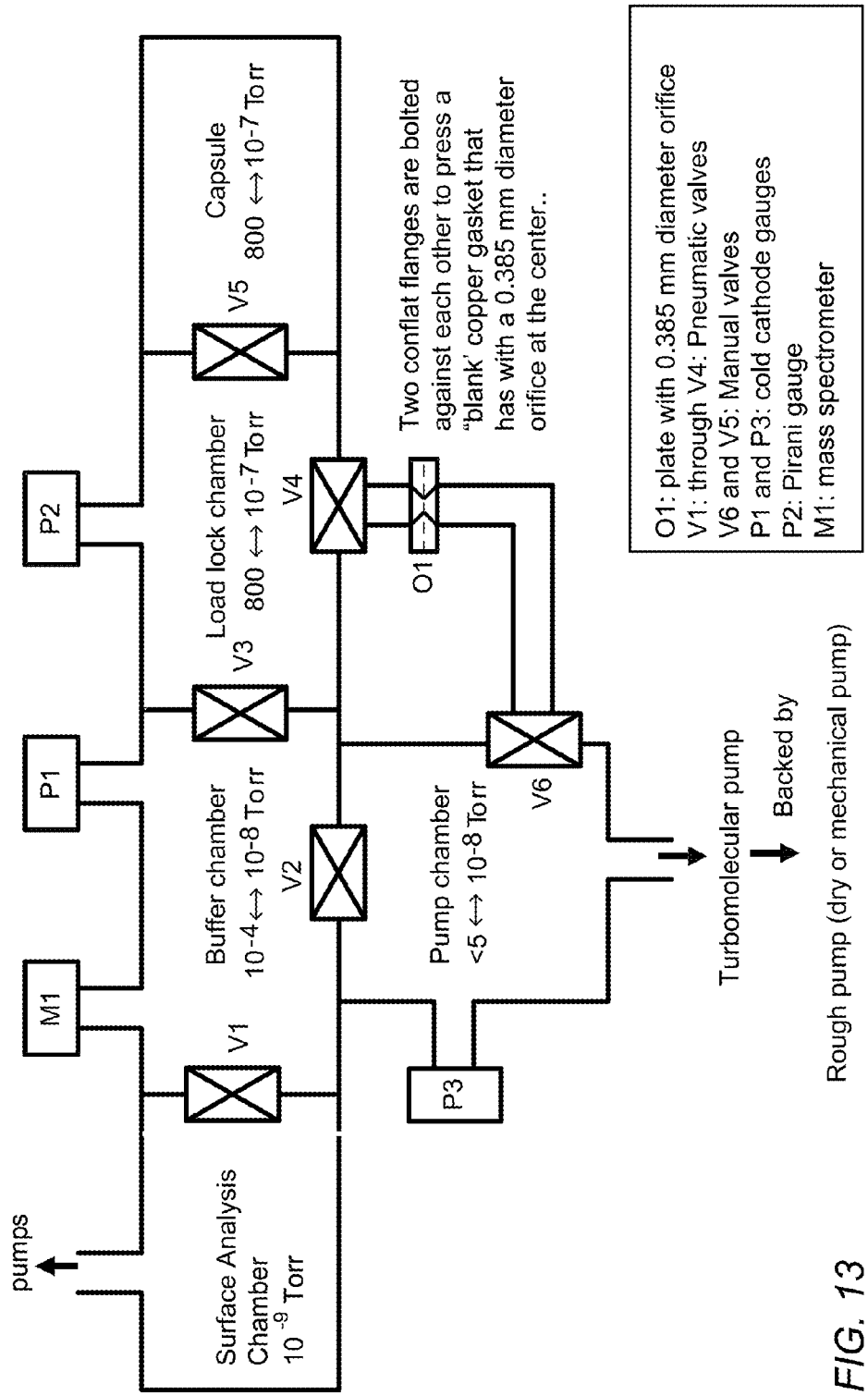
FIG. 13 depicts a schematic diagram of the ROx coupled to a surface analysis chamber under ultra-high vacuum.

FIG. 13 depicts a schematic diagram of the ROx coupled to a surface analysis chamber under ultra-high vacuum. Each chamber of the ROx is shown with a range of pressures that may be obtained via differential pumping. With differential pumping, a transition may be made from atmospheric pressure (760 Torr) to UHV ($10^{-8}$ Torr) in under 12 minutes. The capsule chamber and load lock chamber may both transition between pressures of 800 Torr and $10^{-7}$ Torr. The buffer chamber may transition between pressures of $10^{-4}$ Torr and $10^{-8}$ Torr. The pump chamber may transition between pressures of 5 Torr and $10^{-8}$ Torr. The surface analysis chamber may maintain a pressure on the order of $10^{-9}$ Torr.

Figure 14:
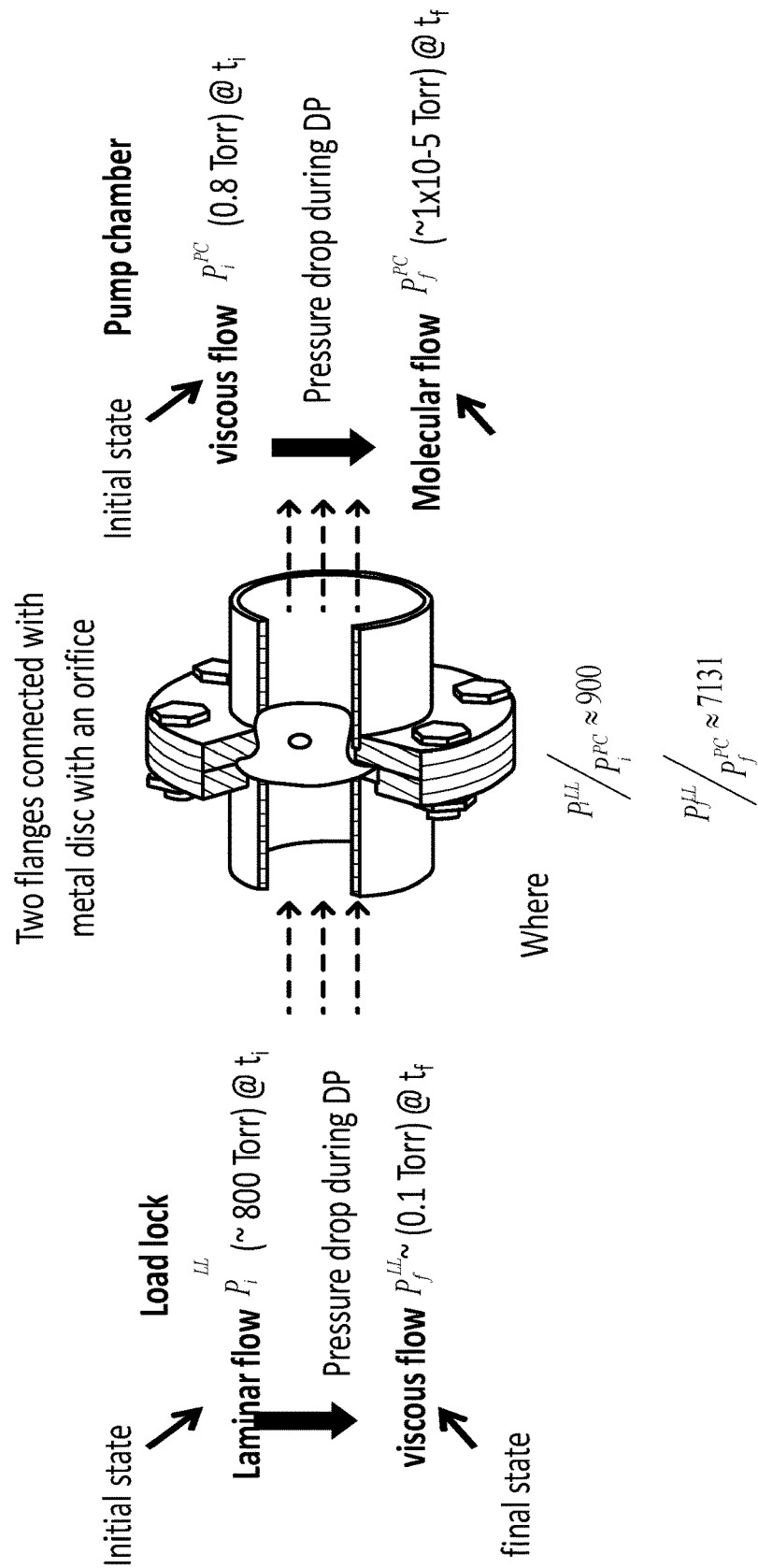
FIG. 14 depicts a schematic diagram of an orifice on a disc located between a load lock chamber and a pumping chamber.

FIG. 14 depicts a schematic diagram of orifice located between a load lock chamber and a pumping chamber. In ROx, the load lock and pump chambers are connected with one flexible tube and a pneumatic valve (V4), both equipped with UHV conflat flanges as schematically shown in FIG. 14. Typically, two conflat flanges press a metal gasket ring as a seal to prevent air leaks under UHV conditions. For differential pumping, ROx may use a blanket metal gasket (or disc) that has a 0.385 mm diameter orifice at the center. The orifice modulates the gas flow rate between the load lock and pump chamber during pump down from atmospheric pressure (800 Torr) to 0.1 Torr (set pressure point at the load lock chamber) using a turbomolecular pump backed by a mechanical pump. In the pump chamber, the initial pressure, prior to differential pumping is shown as 0.8 Torr. Following differential pumping, the final pressure in the pump chamber is shown as 10-5 Torr. Thus, differential pumping causes the load lock chamber to transition from laminar flow to viscous flow, and causes the pump chamber to transition from viscous flow to molecular flow. The initial pressure differential, $P_i^{LL}/P_i^{PC}$ is shown on the magnitude of 900. The final pressure differential, $P_f^{LL}/P_f^{PC}$ is shown on the magnitude of 7000. This allows the pump chamber to transition uninterruptedly from viscous to molecular flow exclusively using a turbomolecular pump (backed by a rough, mechanical pump). At the end of differential pumping, gas throughput is increased by rerouting the gas flow into the buffer and pump chambers.

There exist numerous advantages to applying differential pumping using a turbomolecular pump. For example, gas molecules are given momentum such as gas flow in one direction during a pump down (with the exception of hydrogen gas), preventing backstreaming of oxidants (e.g., water and molecular oxygen) and contaminants (e.g., oil vapor) from roughing pumps, (e.g., a mechanical or scroll pump), into capsule, load lock, buffer, and pump chambers, including the surface analysis chamber during the transition from atmospheric pressure to high vacuum conditions. Turbomolecular pumps have the widest operating pressure range and are capable of crossing over from high vacuum (molecular flow) to backing vacuum (viscous flow~3 Torr) and back to high vacuum without detrimental changes in performance. Further, turbomolecular pumps provide consistent throughputs in both low vacuum viscous and molecular flow regimes. These throughputs do not vary over time and not are dependent on the lifetime of hardware components of the turbomolecular pump. In general, a turbomolecular pump either operates fully at its specifications or completely malfunctions due to one or more faulty components. In other words, turbomolecular pumps have only two states: ON or OFF. The OFF state is most likely due to a faulty component.

Still further, turbomolecular pumps may provide an uninterrupted and continuous pump down, pressure peaks followed by a pump down, and pressure-vs.-time curves during the transition from differential pumping to high conductance pumping path. Differential pumping via a turbomolecular pump actuates a gas load (or amplitude) of a pressure spike into the buffer chamber as gases from the load lock chamber or the sample capsule travel on their way to the pump chamber. This gas load allows a pressure spike and pump down vs. time curves to be recorded a sampling rate of 10 milliseconds (this sampling rate is the fastest rate achievable with this configuration and is limited by the pressure controller). Further, this process yields highly repeatable pressure spikes, followed by the pump down, and repeatable pressure-vs.-time curves. This repeatability allows a user to generate FOMs for ROx and other equipment needed as part of the transfer (e.g., glove box).

Figure 15:
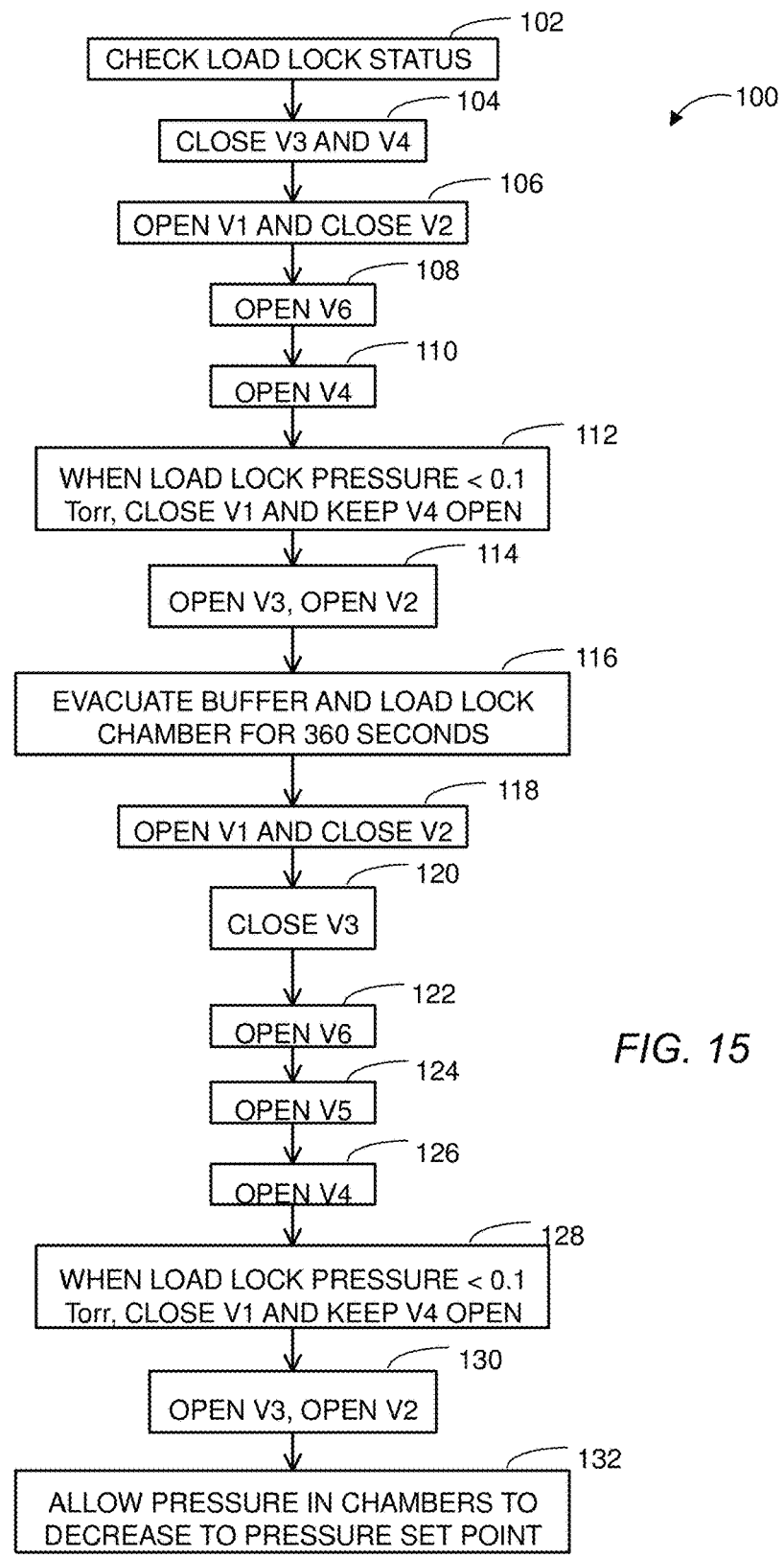
FIG. 15 depicts a flow chart for an example method for a semi-automated routine to activate differential pumping.

FIG. 15 depicts an embodiment of a method 100 for a semi-automated routine to activate differential pumping. The method will be described in reference to a ROx apparatus, such as the apparatus diagramed in FIG. 13, but may be applied to similar apparatuses. Method 100 may begin at 102 with determining the status of the load lock chamber. If the load lock chamber is under atmospheric pressure and manual valve V5 is closed, method 100 may proceed.

At 104, method 100 may include closing valves V3 and V4. This will isolate the load lock chamber from the buffer and pump chambers. At this point, the load lock chamber may be filled with 780 Torr of Argon (99.995%, water and molecular oxygen≤0.2 ppm) following purging for a user determined purge time interval with an inert gas.

At 106, method 100 may include opening valve V1 and closing valve V2. As a result of this, pumping to the buffer chamber is switched from the pumping chamber to the pump of the surface analysis chamber. This valve sequence allows for evacuation of the buffer chamber using pumps from the surface analysis chamber. This step minimizes outgassing from the walls of the buffer chamber and maintains the buffer chamber in the UHV range ($<4\times10^{-8}$ Torr).

At 108, method 100 may include opening valve V6. This manual valve usually remains open. At 110, method 100 may include opening valve V4. This step activates differential pumping between the load lock and pump chamber. Gas throughput may be modulated via a 0.385 mm diameter orifice (O1) while the pump chamber is under continuous pumping by a turbomolecular pump (backed by a rough pump).

At 112, method 100 may include allowing the load lock pressure to decrease below 0.1 Torr, followed by closing valve V1 and maintaining valve V4 in the open state. This step continues differential pumping but isolates the buffer chamber from the STC chamber of the surface analysis chamber.

At 114, method 100 may include opening valve V3 followed by opening valve V2. As a result of this, argon gas is re-routed into the buffer chamber (which has a higher gas throughput) and directly into the pump chamber while valve V4 remains open.

At 116, method 100 may include evacuating the buffer and load lock chambers for 360 seconds with the turbomolecular pump. As a result of this action, the pressures in the load lock and buffer chambers should drop below $2\times10^{-7}$ Torr. At this point, the capsule is under atmospheric pressure (e.g., inert gas at 760 Torr) 27. An objective of differential pumping is to evacuate the capsule from atmospheric pressure to a vacuum pressure of 0.1 Torr or an alternative chosen set point.

At 118, method 100 may include opening valve V1 and closing valve V2. As a result of this action, pumping of the buffer chamber is switched from the pumping chamber to the pumps of the surface analysis chamber. At 120, method 100 may include closing valve V3. This action isolates the load lock from the buffer chamber. At 122, method 100 may include opening valve V6. Valve V6 is usually open.

At 124, method 100 may include opening valve V5. This action manually opens the valve of the capsule. The pressure between the load lock chamber and capsule may equilibrate to 350 Torr. At 126, method 100 may include opening valve V4. This action activates differential pumping between the load lock and pump chamber. Gas throughput is controlled and limited via the orifice (O1) while the pump chamber is under continuous pumping by a turbomolecular pump (backed by a rough pump).

At 128, method 100 may include allowing the pressure in the load lock to drop from 350 Torr to less than 0.1 Torr, followed by closing valve V1 and maintaining valve V4 in the open state. This action continues differential pumping, but isolates the buffer chamber from the STC chamber of the surface analysis chamber.

At 130, method 100 may include opening valve V3, followed by opening valve V2. This action results in argon gas being re-routed into the buffer chamber and directly into the pump chamber while valve V4 remains open.

At 132, method 100 may include allowing the pressure in the buffer, load lock, and capsule chambers to decrease to the set pressure point, for example 2×10-7 Torr. The result of this action is that the load lock and capsule chambers are under vacuum and ready for sample retrieval and introduction into the surface analysis chamber.

FIG. 16 depicts an example plot of representative pressure vs. time curves during a differential pumping operation. The differential purging operation is depicted in three stages: Load lock purging, differential pumping and high conductance. During load lock purging, the load lock pressure (line A) and pump chamber pressure (line B) remain substantially constant. The pressure in the buffer chamber increases, then decreases to $4\times10^{-8}$ Torr.

As the operation switches to differential pumping, the pump chamber pressure spikes to 1.3 Torr. Following this transition, the load lock, pump chamber and buffer chamber pressures decrease throughout the differential pumping chamber, until the load lock pressure reaches 0.1 Torr. At this point, valve V1 is closed, causing a pressure spike in the pump chamber and buffer chamber. Following this spike, the turbomolecular pump is allowed to evacuate the chambers for 360 seconds, resulting in the pump down vs. time curve during high conductance.

Figure 17C:
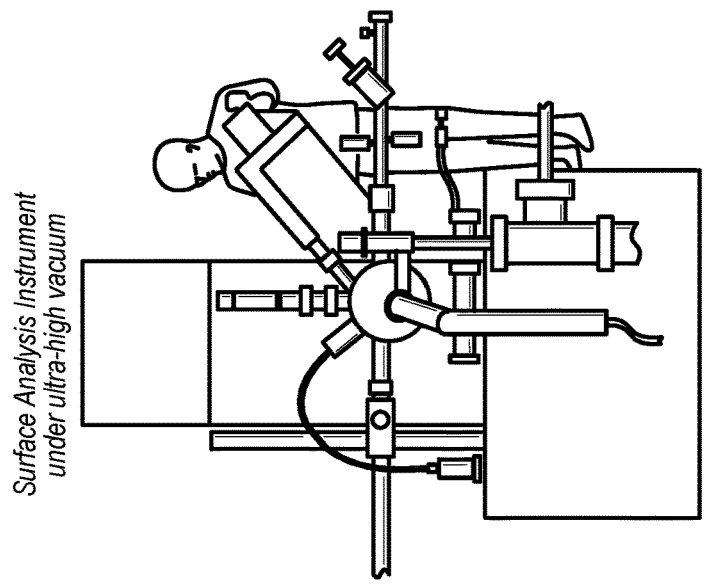
FIGS. 17A-C depict diagrams of an example application of the ROx.
Figure 17B:
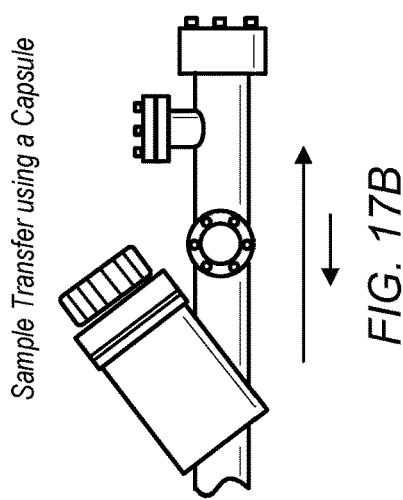
Figure 17A:
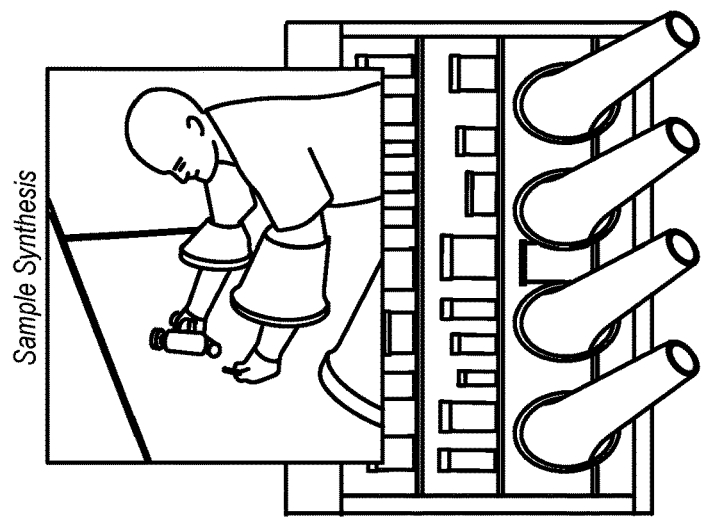

FIGS. 17A-C depict diagrams of an example application of the ROx. The depicted application involves transferring samples from a glove box to a UHV surface analysis chamber. In some embodiments, samples may be transferred in the opposite direction, from the analysis chamber to the glove box. Samples may be synthesized in a glove box under inert gas, for example Argon at 1000 Torr. The inert environment may contain trace levels of water and molecular oxygen, on the order of 1 part-per-million, or a partial pressure of $10^{-4}$ Torr. Samples may be transferred using a capsule from the glove box to the analysis chamber (or vice-versa). The surface analysis chamber may be under UHV, with partial pressure on the order of 2×10-9 Torr, and may contain traces of water and molecular oxygen on the order of $10^{-9}$-$10^{-10}$ Torr. The surface analysis chamber may include an analysis instrument, for example an X-Ray photoelectron spectrometer (XPS).

The ROx interface may be applied in the transfer of samples, using a capsule to physically carry the samples, from a glove box or other high pressure chamber to a surface analysis chamber or other UHV chamber. ROx may be coupled to the surface analysis chamber either as an interface or in conjunction with an existing load lock chamber. Sample transfer may be facilitated from multiple purge boxes.

A subroutine or combination of subroutines may be run in conjunction with the transfer of samples from a glove box to a UHV chamber. The subroutines may be utilized to measure pressure curves, including a pressure spike and pump down vs. time curves, and may be further utilized to develop Figures of Merit (FOMs) for the sample transfer. As described above with regard to differential pumping, following the loading of samples to a capsule in a glove box under atmospheric pressure, the capsule may be evacuated from atmospheric pressure to high vacuum using differential pumping. Differential pumping may be executed by pneumatic valves in a semiautomatic sequence mode. After differential pumping is completed, other pneumatic valves may be activated to switch to high conductance pumping. Pressure gauges may be used to measure and record pressure spikes and pump down vs. time curves. Pressure spikes and pump down vs. time curves may be acquired for a plurality of distinct pumping stages, including ROx conditioning, environment pumping, capsule pumping and outgassing. The pressure spikes and pump down vs. time curves may then be fit to a plurality of parameterized functions. The fit parameters may be designated as FOMs, and may be further utilized to evaluate the reliability of sample transfer.

Figure 18:
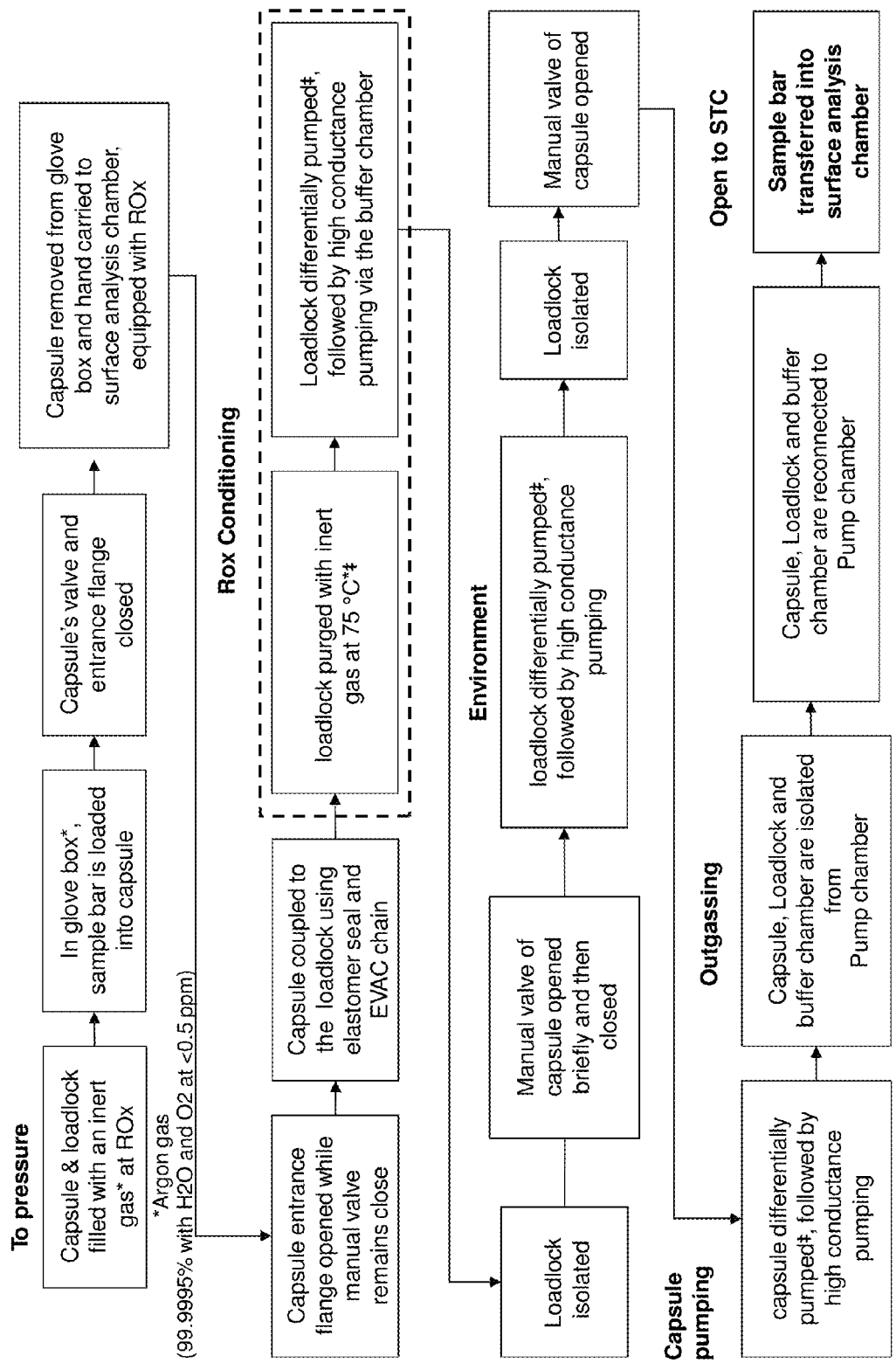
FIG. 18 depicts a flow chart for an example method for using ROx analysis for transferring samples between chambers and acquiring Figures of Merit.

FIG. 18 depicts a flow chart for an example high level method for using ROx analysis for transferring samples between chambers and acquiring Figures of Merit. In one example, samples are transferred from a glove box to a surface analysis chamber. The method illustrates four subroutines that are described further below including ROx conditioning, environment pumping, capsule pumping and outgassing, but more or fewer subroutines may be used to define pumping stages.

Each subroutine may include numerous steps or sequences. The ROx conditioning subroutine may include checking inert gas purity (e.g., Argon), purge sequence, and vacuum baseline levels of the load lock, pump, and buffer chambers. This subroutine may ensure that the load lock has returned to baseline vacuum after it has been exposed to ambient air during the release and re-attachment of the capsule. The environment pumping subroutine may include checking the purity of a carrier inert gas (e.g., Argon from a glove box where samples were loaded) in the capsule with respect to the purity of the inert gas in ROx (e.g., Argon). The capsule may be opened to release gases into an evacuated load lock and then closed during pump down.

The capsule pumping subroutine may include opening the manual valve of the capsule and maintaining the valve open during pump down. This subroutine further includes checking the vacuum baseline level of the capsule carrying samples. The outgassing subroutine may include isolating the buffer chamber, load lock chamber and capsule from the pump chamber, checking for the rate of outgassing of samples in the capsule by recording a pressure rise for 60 sec. Following the pressure rise, the pump chamber may reconnected, and a pump down of the chamber and capsule may be commanded a function of time.

Table 1 depicts a matrix that may be used to evaluate sample transfer from a glove box to a surface analysis chamber using pump down curve ratios.

TABLE 1

| | Conditioning ROx | Environment | Capsule Pump | Outgassing |
|---|---|---|---|---|
| Set I | R1 & R2 | E1 | C1 | O1 |
| Set II | R1 & R2 | E2 | C2 | O2 |
| Ratio | [abs(R1 − R2)]/R1 | [abs(E1 − E2)]/E1 | [abs(C1 − C2)]/C1 | — |

Set I comprises baseline curves for ROx acquired using 99.9995% Argon (including less than 0.5 ppm of $H_2O$ and $O_2$) as a reference. After loading samples in a glove box and reconnecting the capsule to ROx, curves E2, C2 and O2 are measured from gases which originated from the glove box. The ratios have a parameterized fitting method to calculate in a finite number of steps a set of FOMs at the four distinct pumping stages of ROX conditioning, environment pumping, capsule pumping and outgassing.

Figure 19:
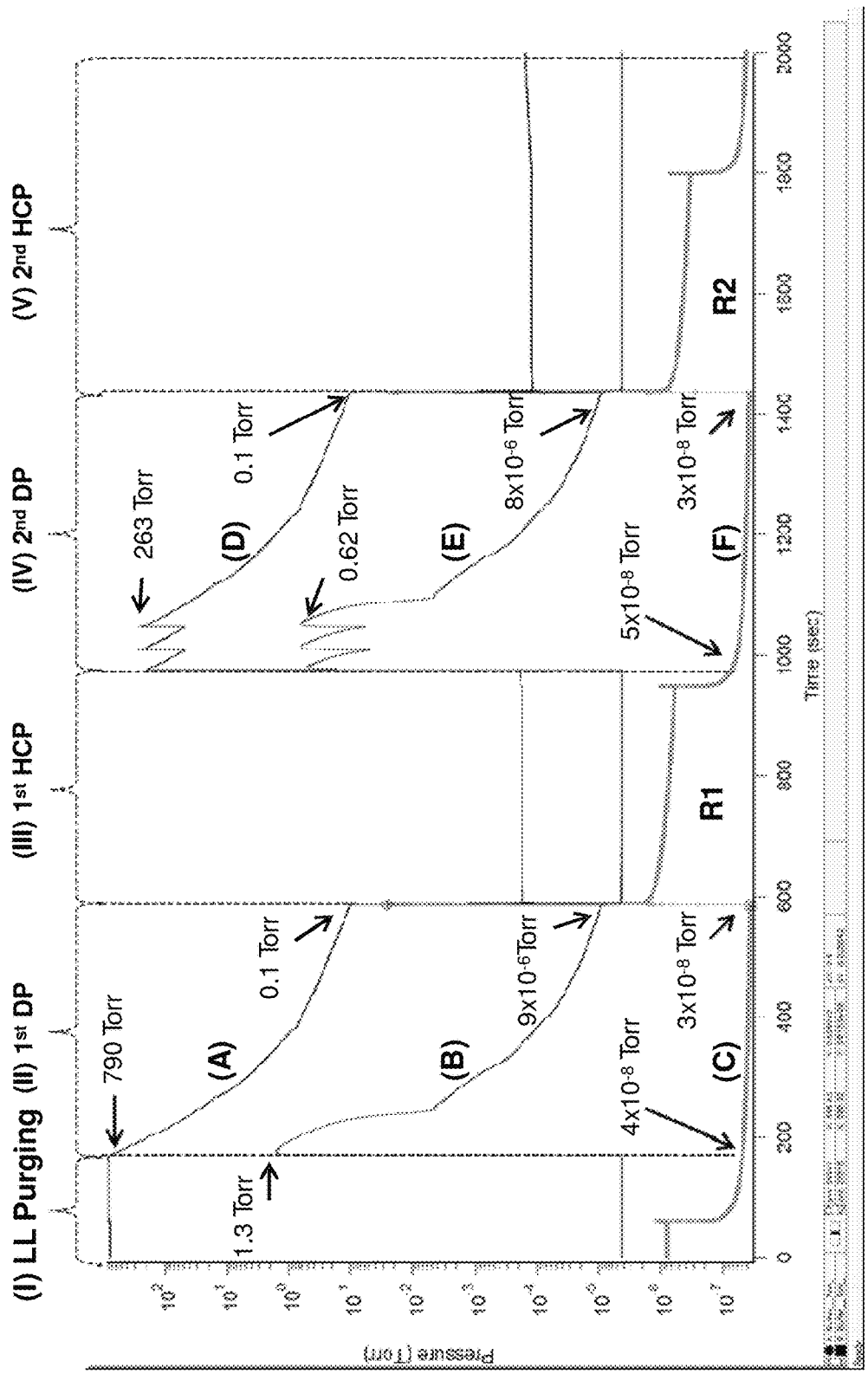
FIG. 19 depicts an example plot of representative pressure vs. time curves during a differential pumping operation.

FIG. 19 depicts an example plot of representative pressure vs. time curves during a differential pumping operation. The plot depicted in the example depicts representative spectra measured using the ROx conditioning subroutine showing (1) Load lock Purge, (2) Differential Pumping and (3) High Conductance pumping. Without a break in pressure recording, the load lock was re-pressurized with 200 Torr of Inert gas, pump down is re-start with (4) Differential Pumping, followed by (5) High Conductance pumping. Changes in pressure were recorded at the Load lock, Pump, and Buffer Chambers; each equipped with its own pressure gauges. FIG. 19 depicts each pressure-vs.-time curve, overlayed using different colors, recorded at these chambers. The purpose of re-pressurization is to check the "condition" of ROx by recording the pressure spike & pump down vs. time curves for the second time at the Buffer Chamber (curves C and F). A detailed analysis of these curves depicts a variation of these curves is due to intrinsic water level (0.5 part-per-million) contained within the inert gas Argon gas source. If all the components of ROx are performing to specifications, the variation of these curves is set based on acceptable limits.

Figure 20:
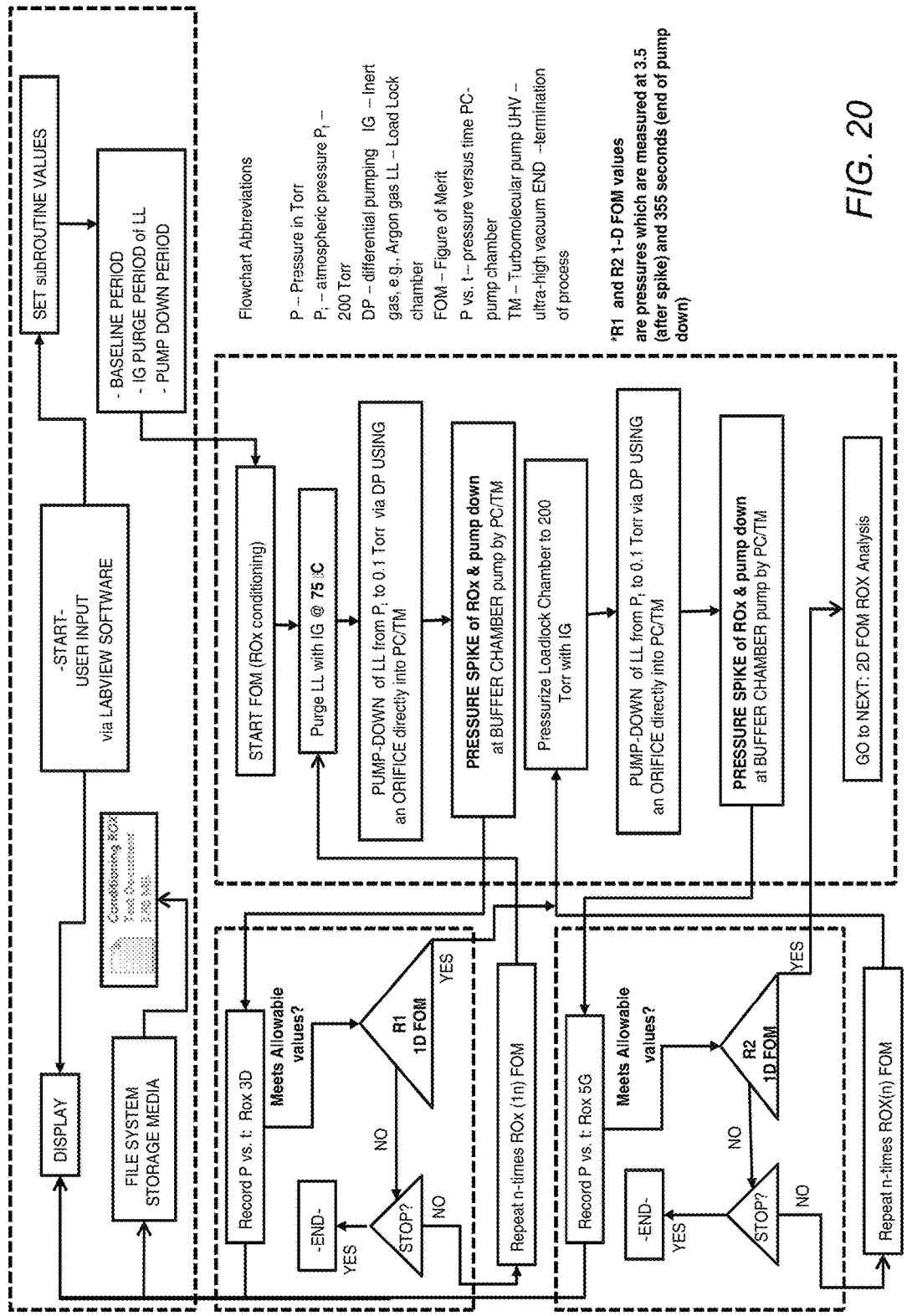
FIG. 20 depicts a flow chart for an example method for measuring pressure spike and pump down vs. time curves and calculating Figures of Merit for ROx conditioning.

FIG. 20 depicts a flow chart for an example method for measuring pressure spike and pump down vs. time curves and calculating Figures of Merit for ROx conditioning. The method may be executed as part of a larger routine or subroutine, such as the method shown in FIG. 18, or may be executed independently. In some embodiments, following the completion of this method, an additional method may be executed, for example, the method shown in FIG. 24. This method or similar methods may be used to calculate FOM values for a sample transfer routine.

Table 2 depicts a description of values of pressure spike and pump down vs. time curves as depicted in FIG. 19. Values in table 2 may be derived through a method, such as the method depicted in FIG. 20. In regions II and IV for the load lock, differential pumping is executed by pressure values chosen for the initial and final pressure for the load lock (curves A & D), pump (curves B & E), and buffer (curves R1 & R2) chambers. These pressure set points may be chosen by the user. In regions III and V, figures of merit (FOM) are derived for the ROx from the pressure-vs.-time curves (D & H) where the magnitude of the pressure spike may be primarily determined by the final pressure of the load lock and pump down pressure or total time may be chosen by the user.

TABLE 2

| | | 1st Differential Pumping (Region II) | | | 1st High Conductance pumping (Region III) | | | | |
|---|---|---|---|---|---|---|---|---|---|
| | | Chamber | Initial P | Final P | | Chamber | Initial P | Pressure spike | Final P | Pump down time |
| | P vs. t curve | (Pressure gauge) | (Torr) | (Torr) | P vs. t curve | (Pressure gauge) | (Torr) | (Torr) | (Torr) | (sec) |
| R1 Curve | A | Load lock (P2) | 830 | 0.1 | R1 | Buffer (P1) | 3.2 × 10−8 | 3.1 × 10−2 | 5.9 × 10−7 | 355 |
| | B | Pump (P3) | 1.5 | 1 × 10−5 | | | | | | |
| | C | Buffer/Surface Analysis (P1) | 4 × 10−8 | 3.2 × 10−8 | | | | | | |

| | | 2nd Differential Pumping (Region IV) | | | 2nd High Conductance pumping (Region V) | | | | |
|---|---|---|---|---|---|---|---|---|---|
| | | Chamber | Initial P | Final P | | Chamber | Initial P | Pressure spike | Final P | Pump down time |
| | P vs. t curve | (Pressure gauge) | (Torr) | (Torr) | P vs. t curve | (Pressure gauge) | (Torr) | (Torr) | (Torr) | (sec) |
| R2 Curve | D | Load lock (P2) | 250 | 0.1 | R2 | Buffer (P1) | 3.1 × 10−8 | 3.1 × 10−2 | 3.4 × 10−7 | 355 |
| | E | Pump (P3) | 2.3 | 1 × 10−5 | | | | | | |
| | F | Buffer/Surface Analysis (P1) | 3 × 10−8 | 3.1 × 10−8 | | | | | | |

Figure 21:
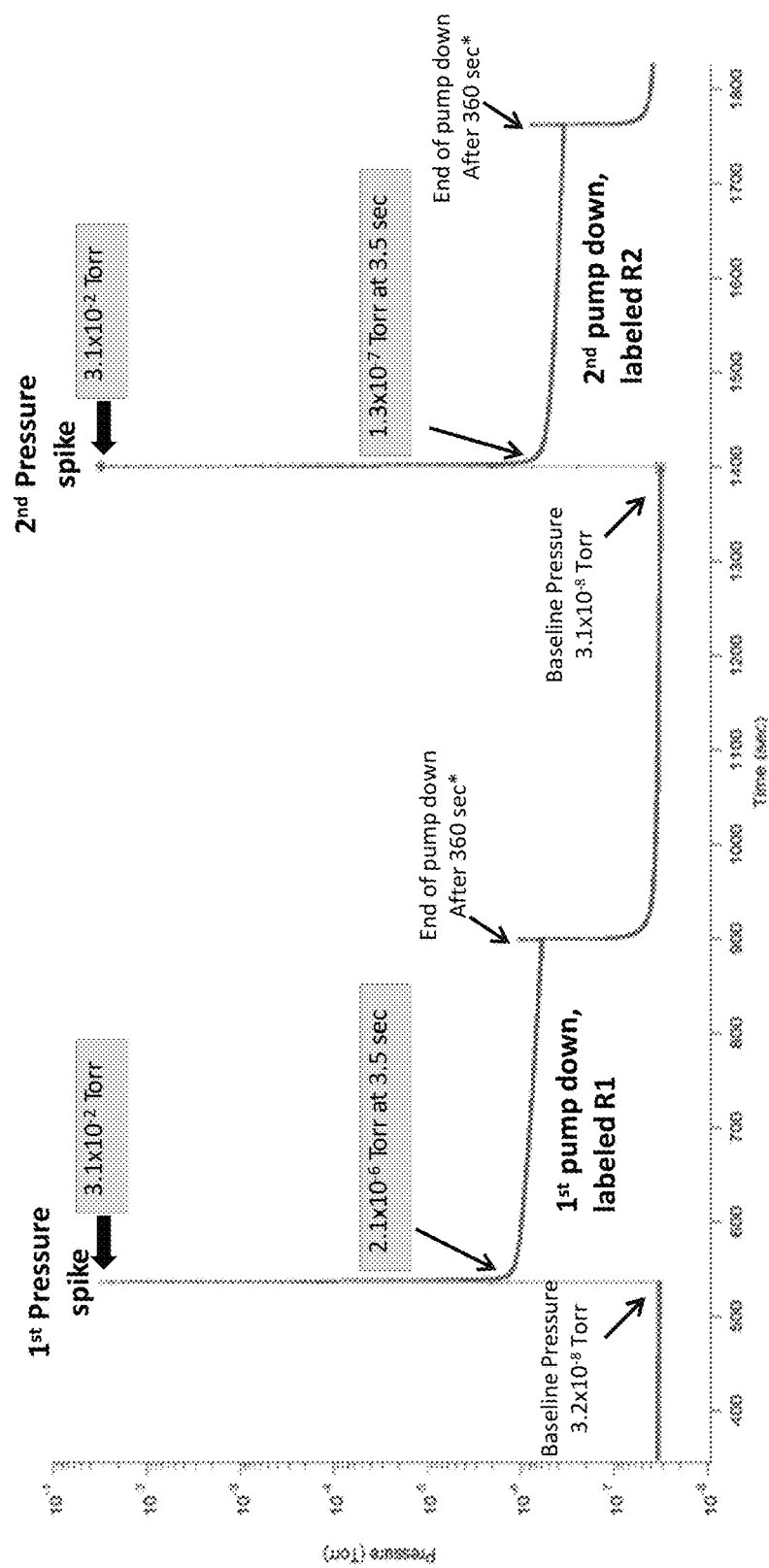
FIG. 21 depicts an example plot of example pressure spike and pump down vs. time curves for a buffer chamber.

FIG. 21 depicts an example plot of example pressure spike and pump down vs. time curves for a buffer chamber. In this example, prior to launching the 1st and 2nd pressure spike, the baseline pressure of the buffer chamber is maintained at ~3×10$^{-8}$ Torr using pumps of the surface analysis chamber. The ensuing pressure spike, which has the same magnitude for both pump downs, serves as a time reference, allowing a direct comparison between the 1st and 2nd pump down when plotted on the same scale, using time as an independent variable. The line shape and magnitude of the pressure spike is measured using a sampling rate of 50 Hz, i.e., every 20 millisecond. After starting the pressure spike, the total time for each pump down is set to 360 sec, using the beginning of the pressure spike as a reference.

FOMs may be calculated from the values derived for the two pressure spikes and pump down vs. time curves depicted in FIG. 21. The first pressure spike and pump down may be recorded after purging and labeled as R1. A one-point analysis FOM may be calculated at 3.5 and 355 seconds and labeled as 1-dimensional FOM (1-D FOM-R1). The second pressure spike and pump down may be recorded after re-pressurization of the load lock and subsequent pump down and labeled as R2. A one-point analysis FOM may be calculated at 3.5 and 355 seconds and labeled as 1-dimensional FOM (1-D FOM-R2). A full range analysis FOM may be calculated from t=0 to 355 seconds and labeled as 2 dimensional FOM (2-D FOM-ROx Ratio) where the ratio is set equal to {absolute (R1−R2)}/R1. The 2-D FOM-ROx Ratio may be represented by a curve by plotting this ratio as a dependent variable against time from t=0 to t=355 seconds.

Figure 22:
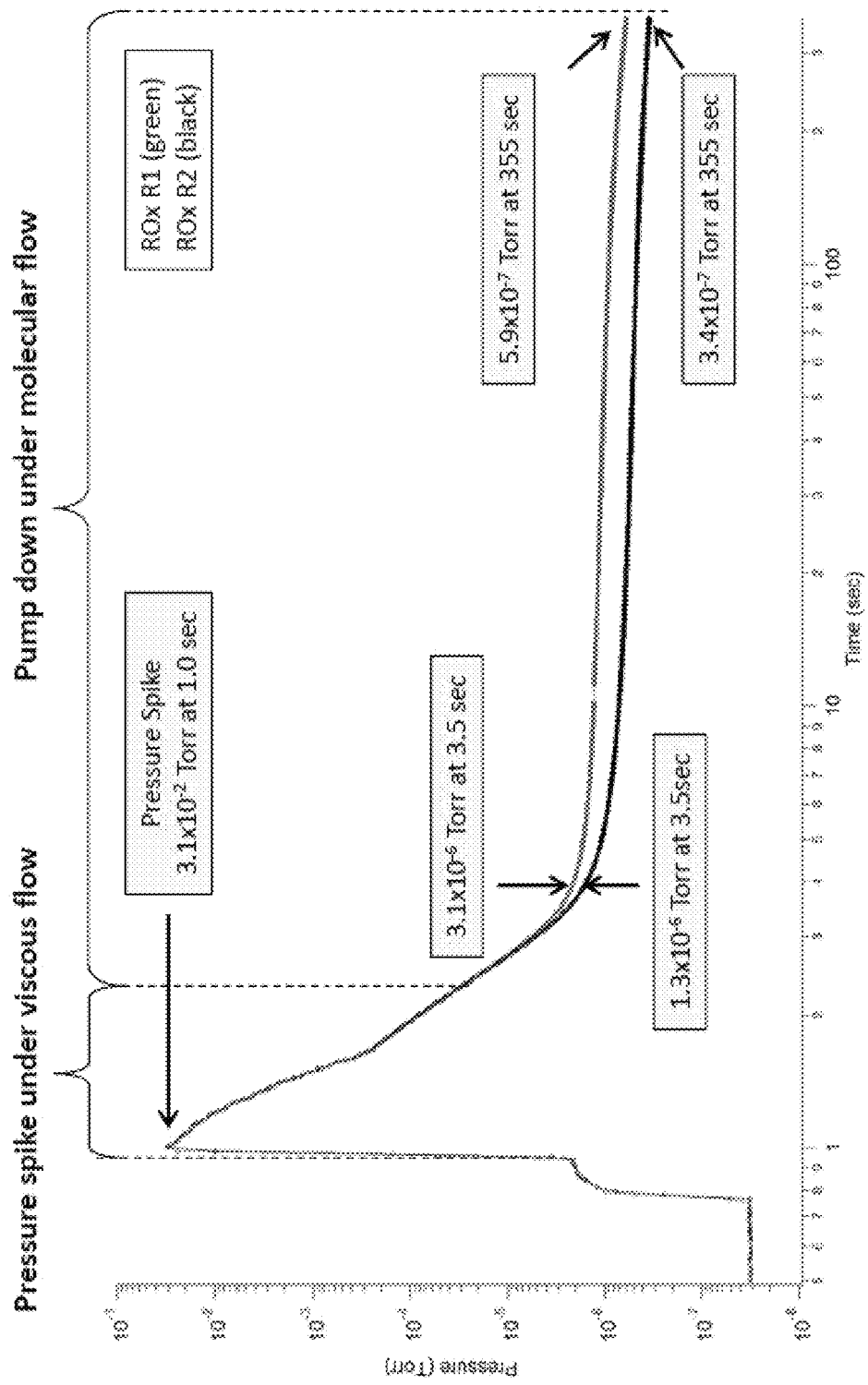
FIG. 22 depicts an example plot of two example pressure spike and pump down vs. time curves acquired with ROx conditioning and one-dimensional Figures of Merit.

FIG. 22 depicts an example plot of two example pressure spike and pump down vs. time curves acquired with ROx conditioning and one-dimensional Figures of Merit. Using the pressure spikes as a time reference peak, the pump down curves, R1 and R2, are overlapped by plotting then against time as the independent variable. The magnitude of these pressure spikes (pressure 3.1×10$^{-2}$ Torr) are identical since the gas flow is under viscous flow, while the pump down region is under molecular flow (pressure<1×10$^{-5}$ Torr) after ~3 seconds after the spike. 1-D FOM for R1 & R2 are pressure values which are measured at 3.5 and 355 seconds. The divergence is due to water adsorption on the wall of the chambers. The baseline pressure is 1.1×10$^{-7}$ Torr.

Table 3 depicts a summary of 1-Dimensional FOMs for ROx conditioning as described above. At t=3.5 and t=355 seconds, the pressure and ratio values in Table 3 may be considered typical values for ROx conditions, and therefore may be assigned as 1-D FOMs for ROx conditioning.

TABLE 3

| | Time (sec) | |
|---|---|---|
| Curve | 3.5 | 355 |
| R1 (Torr) | 3.10E−06 | 5.90E−07 |
| R2 (Torr) | 1.30E−06 | 3.40E−07 |
| Ratio ([absolute (R1 − R2)]/R1) | 0.58 | 0.42 |

Figure 23:
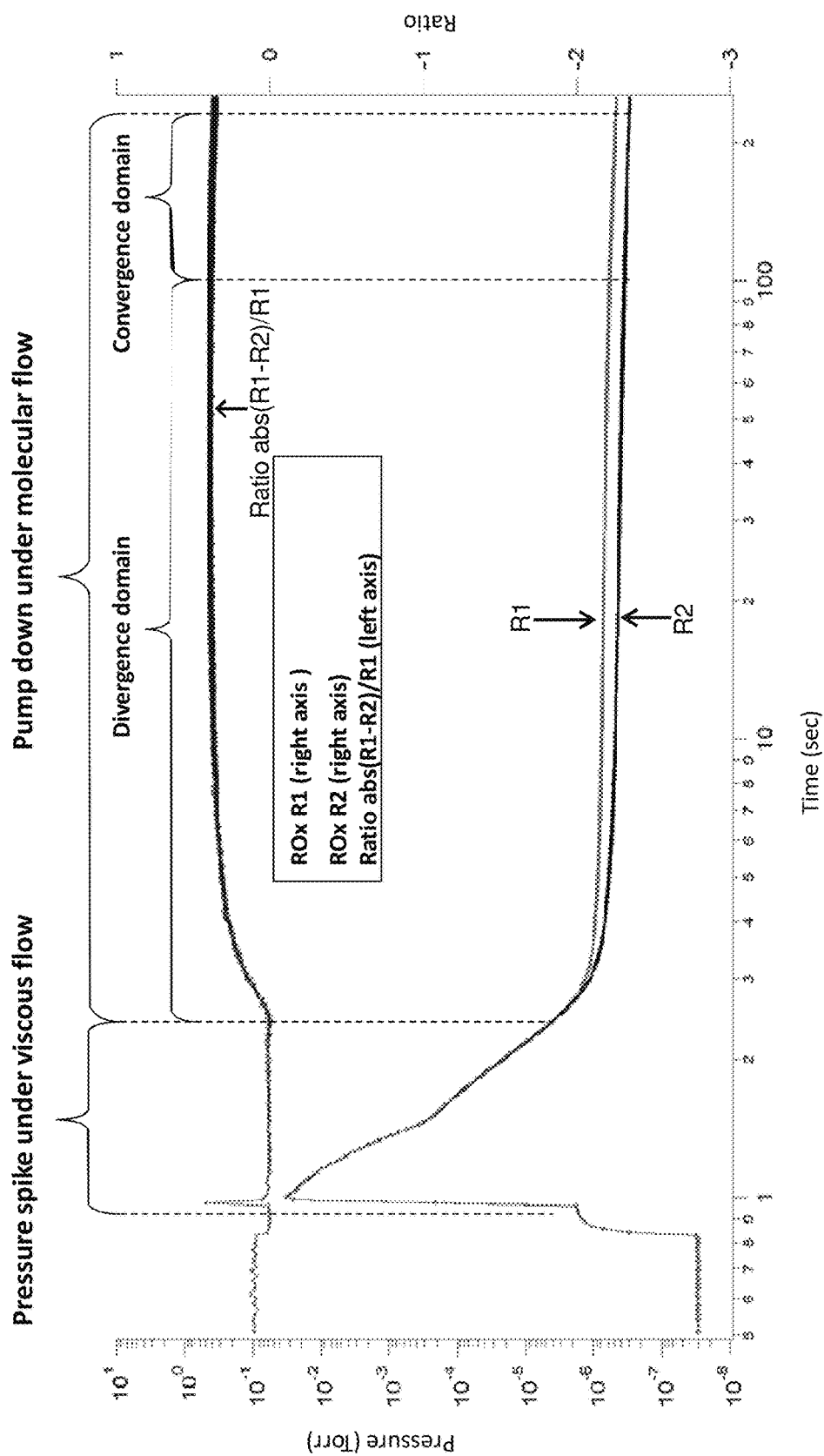
FIG. 23 depicts an example plot of example pressure spike and pump down vs. time curves acquired during ROx conditioning and used to calculate two-dimensional Figures of Merit.

FIG. 23 depicts an example plot of example pressure spike and pump down vs. time curves acquired during ROx conditioning and used to calculate two-dimensional Figures of Merit. Within the molecular flow region, the pump down ratio, {absolute (R1−R2)}/R1, vs. time is divided into two domains. R2 initially sharply diverges from R1 between 2.5 to 5 seconds and then reaches at steady state between 5-100 seconds. This time domain is labeled the divergence domain. From 100 to 360 seconds, both R1 and R2 are slowly converging as the buffer and load lock chambers are pumping down to the baseline pressure, i.e., 3×10-8 Torr. This region is labeled as the convergence domain.

The divergence domain may be used to determine IF levels of oxidant(s) or/and molecular contaminant, (e.g., water and outgassing solvents), are above the specifications of ROx. This region is fitted to single or a sum of exponential functions with the following form:

Single Exponential Function $= y_0 + A_1 \exp\left\{\frac{(x-x_0)}{\tau_1}\right\}$ Sum of Exponential Functions =

$$y_0 + A_1 \exp\left\{\frac{(x-x_0)}{\tau_1}\right\} + A_2 \exp\left\{\frac{(x-x_0)}{\tau_2}\right\}$$

In both examples, $X_0$ is a constant, not a fitting coefficient. The fitting parameters, ($y_0$, A1, A2, tau1, and tau2) of this function may be assigned as the values for the figure of merits for divergence due oxidants and/or contamination. X is time, serving as the independent variable, from 2 to 100 seconds.

The convergence domain may be used to determine a pump down rate between 100 and 360 seconds. It may be fitted to a simple linear function (i.e. f=ax+b). The fitting parameters (a=rate and b=y intercept) of this function may be assigned as the values for the FOMs for this domain. X is time, serving as the independent variable, from 100 to 360 seconds.

If the convergence domain does not fit to a linear function, it may be fitter to a single exponential function with the following form:

$$\text{Exponential Function} = y_0 + A_1 \exp\left\{\frac{-(x - x_0)}{\tau_1}\right\}$$

The fitting parameters, ($y_0$, A, tau) of this function may be assigned as the values for the FOMs for the convergence domain due to the concentration of oxidants and/or contamination during the pump down. A user may decide if the values of these parameters meet the specification for their applications with respect to the acceptable levels of oxidant(s) and/or molecular contaminant (e.g., water and pump oil).

Figure 24:
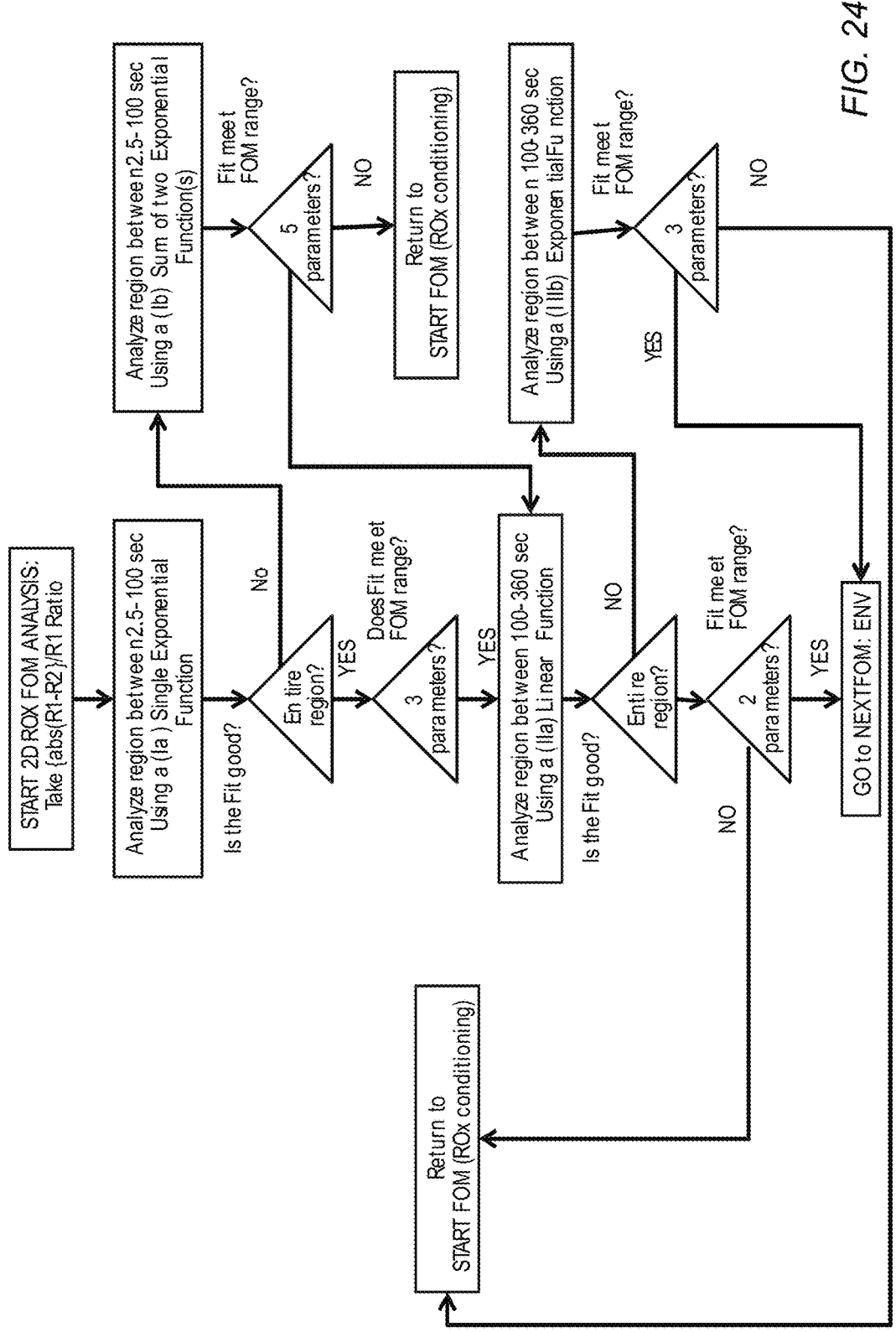
FIG. 24 depicts a flow chart for an example method for two-dimensional ROx Figures of Merit analysis.

FIG. 24 depicts a flow chart for an example method for two-dimensional ROx Figures of Merit analysis. The method may be executed as part of a larger routine or subroutine, such as the method shown in FIG. 18, or may be executed independently. In some embodiments, following the completion of this method, an additional method may be executed, for example, the method shown in FIG. 28. This method or similar methods may be used to calculate FOM values for a sample transfer routine.

Figure 25:
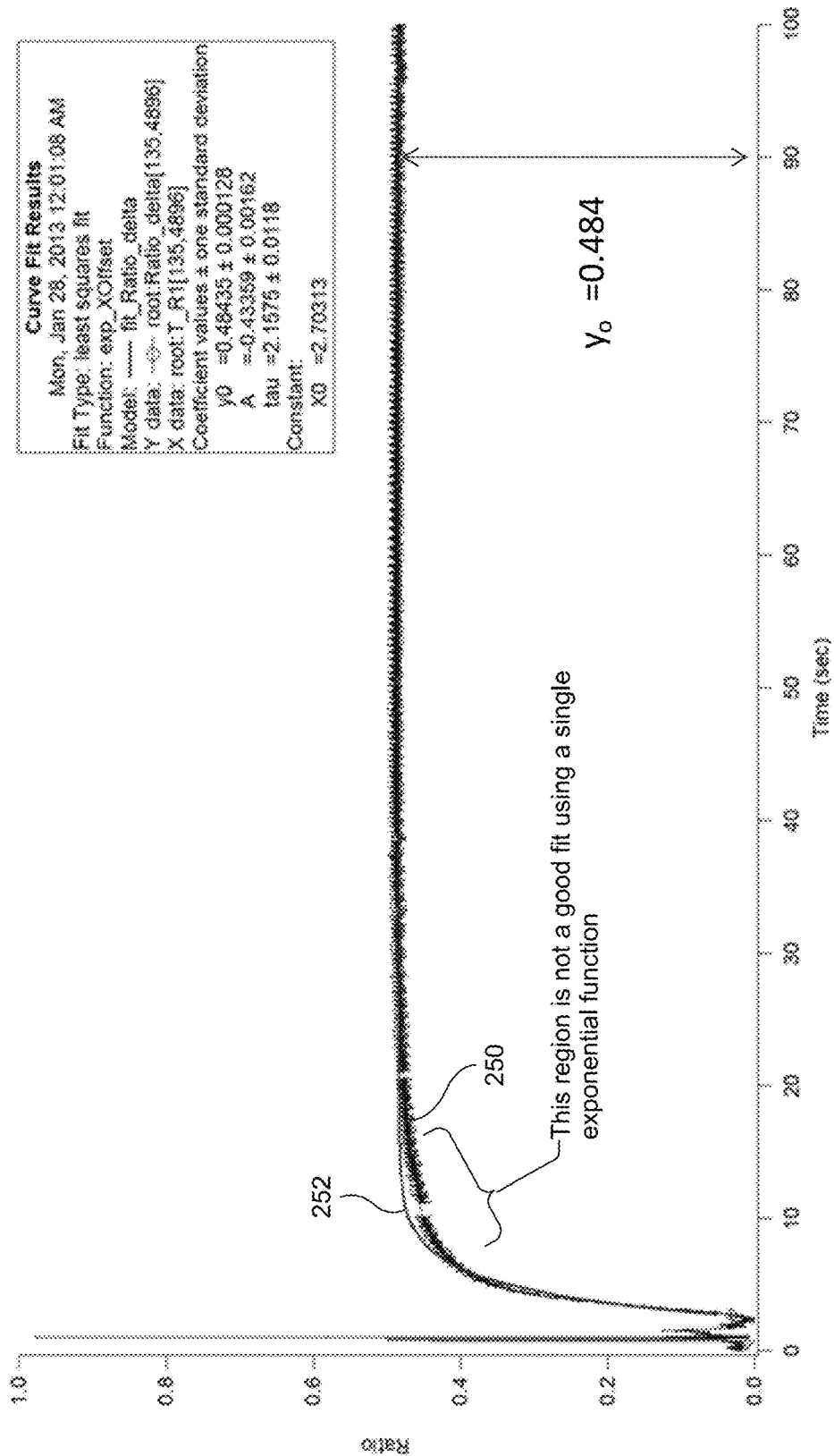
FIG. 25 depicts an example plot of an example curve fit of a ratio curve at a divergence domain using a single exponential function.
Figure 26:
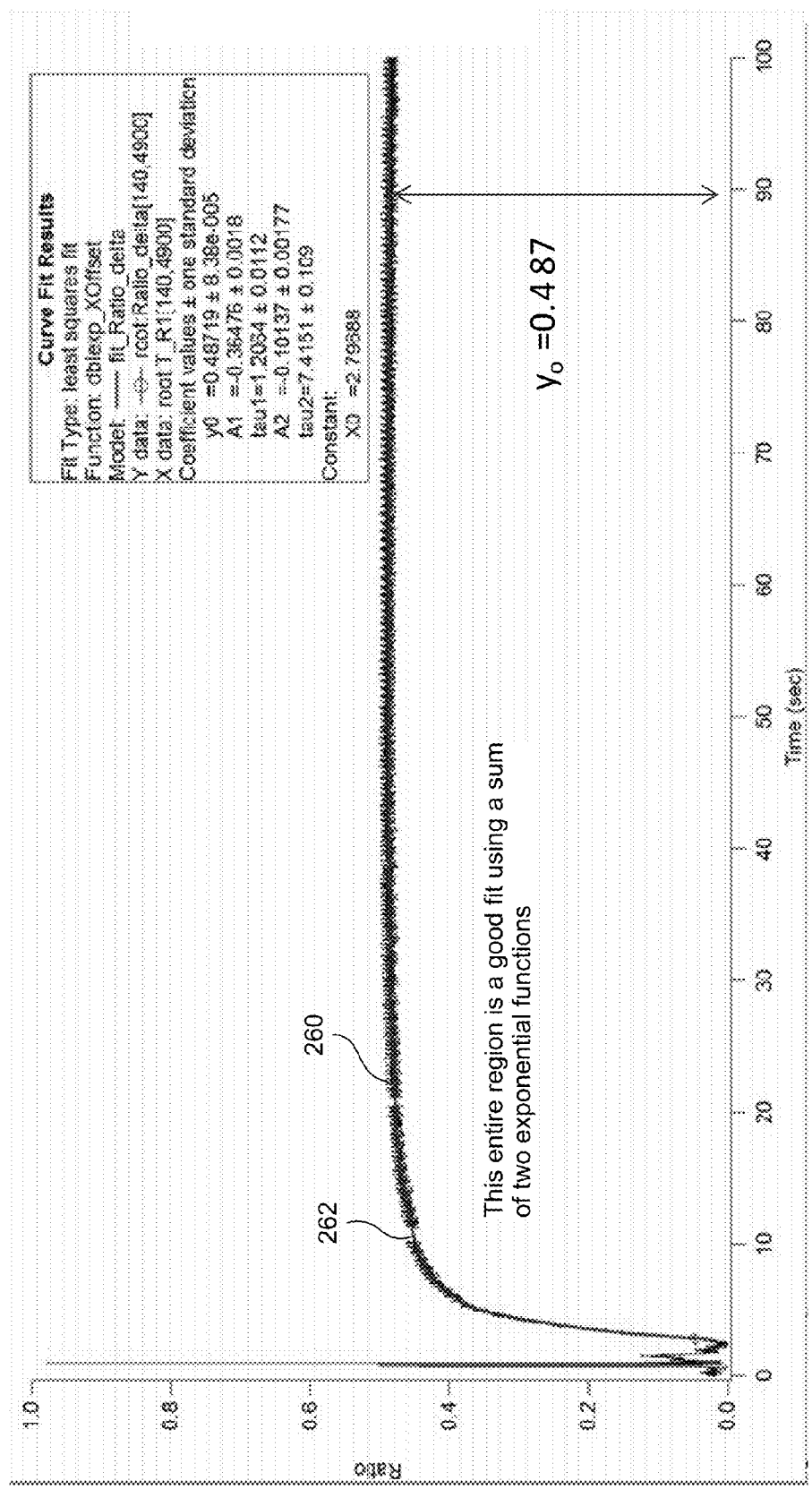
FIG. 26 depicts an example plot of an example curve fit of a ratio curve at a divergence domain using a sum of two exponential functions.
Figure 27:
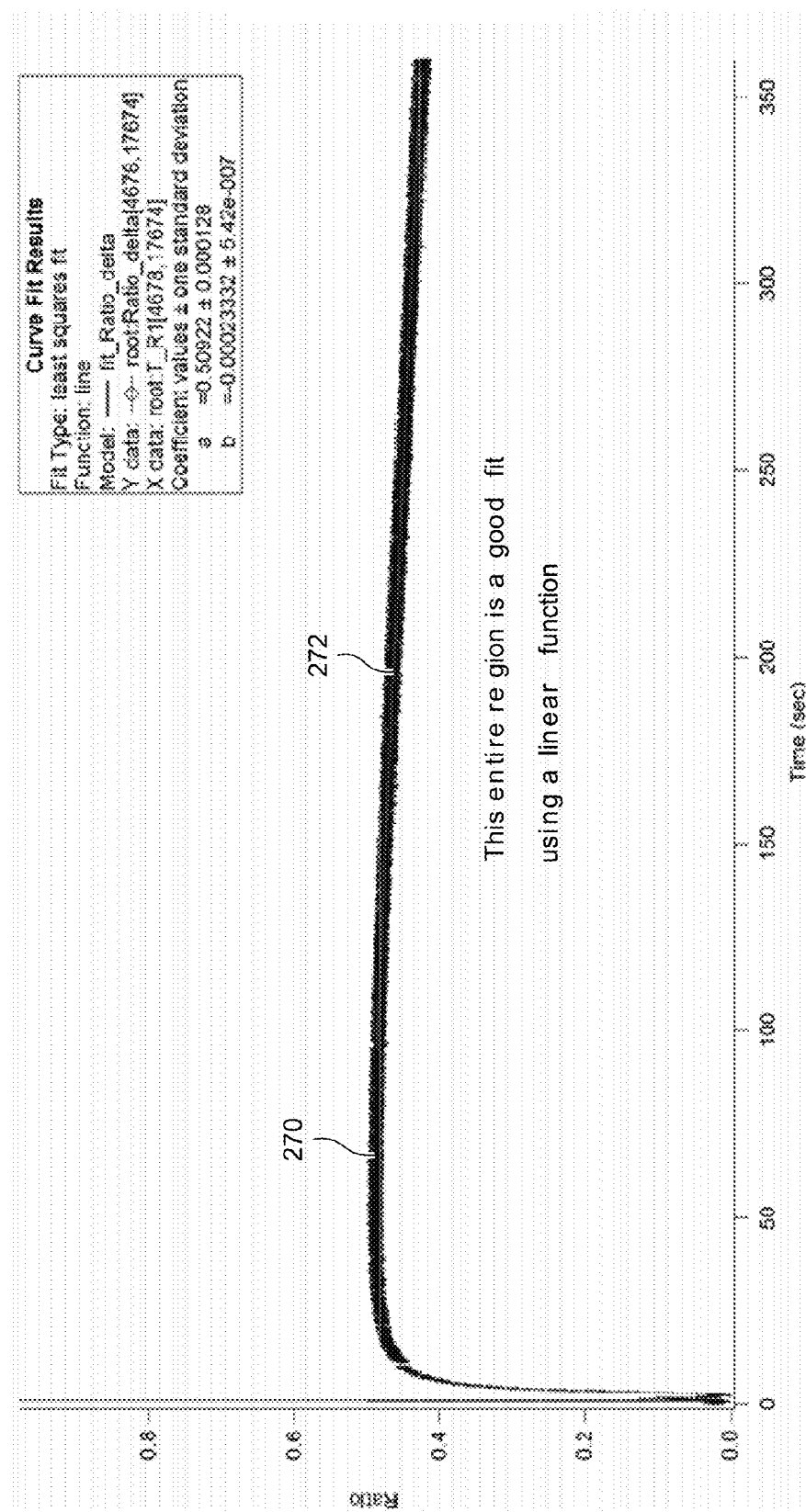
FIG. 27 depicts an example plot of an example curve fit of a ratio curve at a convergence domain using a linear function.

FIGS. 25-27 show example plots of example curve fitting as described above. FIG. 25 depicts an example plot of an example curve fit of a ratio curve at a divergence domain using a single exponential function (experimental ratio 250 vs. single exponential equation fit 252). FIG. 26 depicts an example plot of an example curve fit of a ratio curve at a divergence domain using a sum of two exponential functions (experimental ratio 260 vs. double exponential equation fit 262). FIG. 27 depicts an example plot of an example curve fit of a ratio curve at a convergence domain using a linear function (experimental ratio 270 vs. linear equation fit 272). As shown in FIG. 25, the single exponential function does not fit the ratio curve at the divergence domain for this example. However, the sum of two exponential functions does fit the ratio curve at the divergence domain for this example, as shown in FIG. 26. As shown in FIG. 27, a linear function fits the ratio curve at the convergence domain for this example.

Table 4 depicts a summary of the curve fits of the ratio curve at the divergence and convergence domains as depicted in FIGS. 25-27. The curve fits may be used to calculate six FOM values for ROx conditioning through a method of quality control, for example through a method of statistical processing control (SPC). SPC may be used to ensure that ROx operates at its full potential.

TABLE 4

| Domain | FOM | Value | 1 sigma standard deviation |
|---|---|---|---|
| Divergence | y0 | 0.487 | ±8.4e−5 |
| | A1 | −0.36 | ±0.0018 |
| | tau1 | 1.21 | ±0.01 |
| | A2 | −0.1 | ±0.0004 |
| | tau2 | 7.4 | ±0.1 |
| Convergence | a (intercept) | 0.509 | ±1.2e−04 |
| | b (rate) | −2.3E−04 | ±5.4E−07 |

Figure 28:
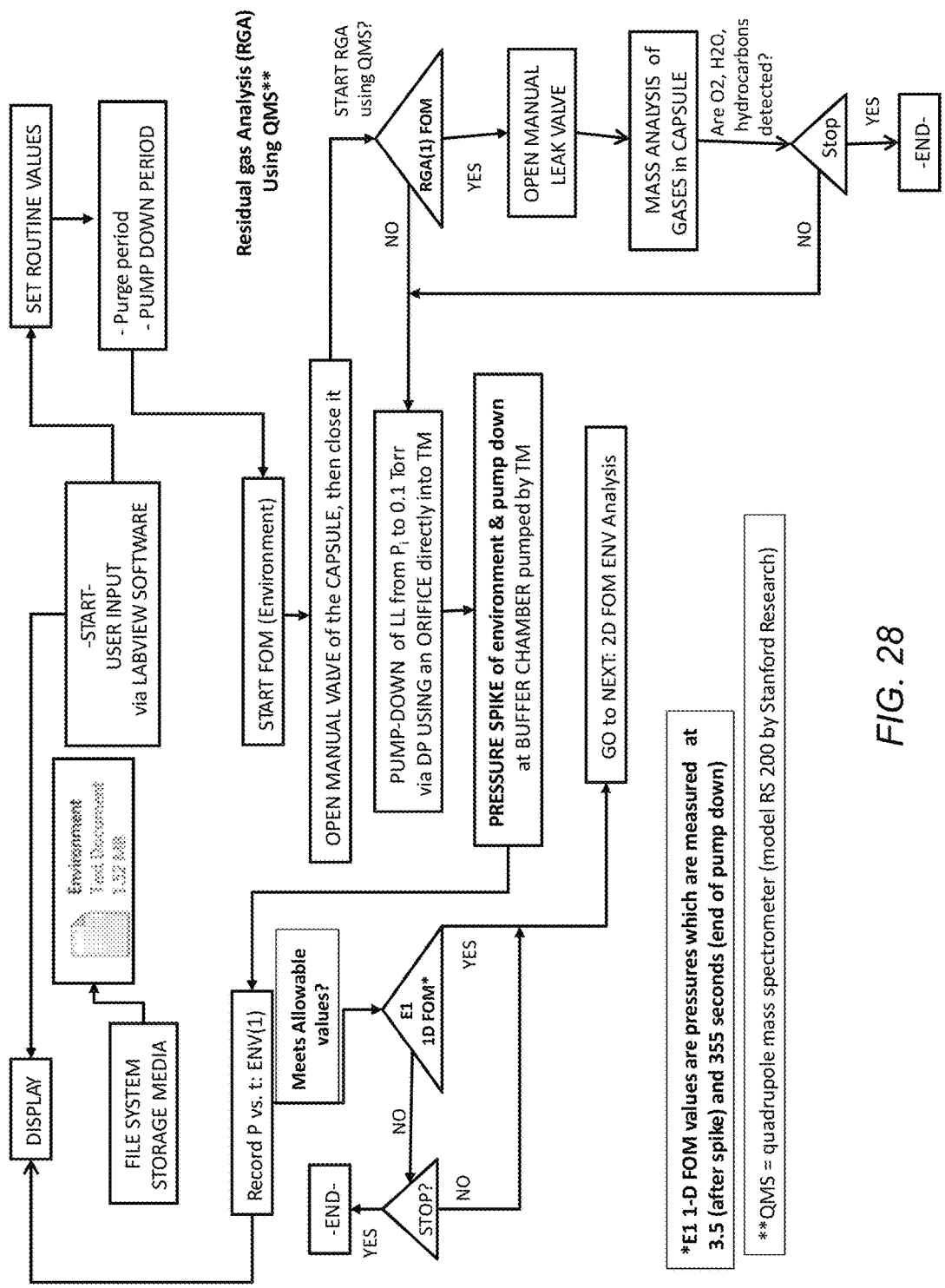
FIG. 28 depicts a flow chart for an example method for evaluating the environment to test gaseous contents of a glove box.

FIG. 28 depicts a flow chart for an example method for evaluating the environment to test gaseous contents of a glove box. The method may be executed as part of a larger routine or subroutine, such as the method shown in FIG. 18, or may be executed independently. In some embodiments, following the completion of this method, an additional method may be executed, for example, the method shown in FIG. 30. This method or similar methods may be used to calculate FOM values for a sample transfer routine.

Figure 29:
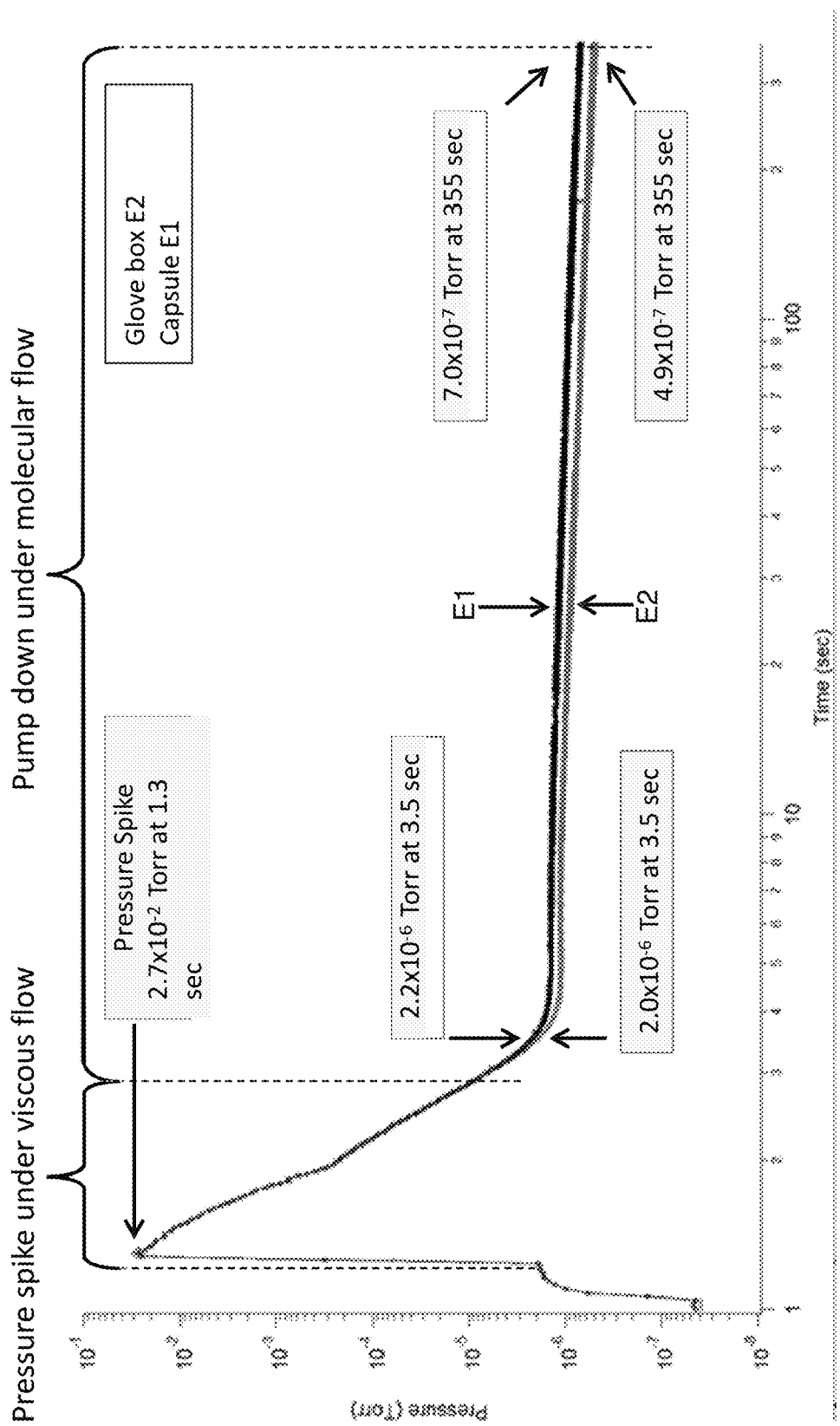
FIG. 29 depicts an example plot of two example pressure spike and pump down vs. time curves acquired with ROx Environment and Glove box environment routines and one-dimensional Figures of Merit.

FIG. 29 depicts an example plot of two example pressure spike and pump down vs. time curves acquired with ROx Environment and Glove box environment routines and one-dimensional Figures of Merit. Using the pressure spikes as a time reference peak, the pump down curves, E1 and E2, may be overlapped and plotted against time as the independent variable. The magnitude of these pressure spike (pressure $2.7 \times 10^{-2}$ Torr) are identical since the gas flow is under viscous flow while the pump down region is under molecular flow (pressure $<1 \times 10^{-5}$ Torr) after ~2.5 seconds. 1-D FOM for E1 & E2 are pressure values measured at 3.5 and 355 seconds.

Table 5 depicts a summary of the 1-dimensional FOMs for environment pumping based on the pump down curves depicted in FIG. 29. The Ratio FOM is set equal to [absolute (E1−E2)]/E1. At t=3.5 and t=355 seconds, the ratio values may be assigned as 1-dimensional FOMs for environment pumping.

TABLE 5

| | Time (sec) | |
|---|---|---|
| Curve | 3.5 | 355 |
| E1 ROx (Torr) | 2.20E−06 | 7.00E−07 |
| E2 ENV (Torr) | 2.00E−06 | 4.90E−07 |
| Ratio FOM [absolute (E1 − E2)]/E1 | 0.09 | 0.30 |

Figure 30:
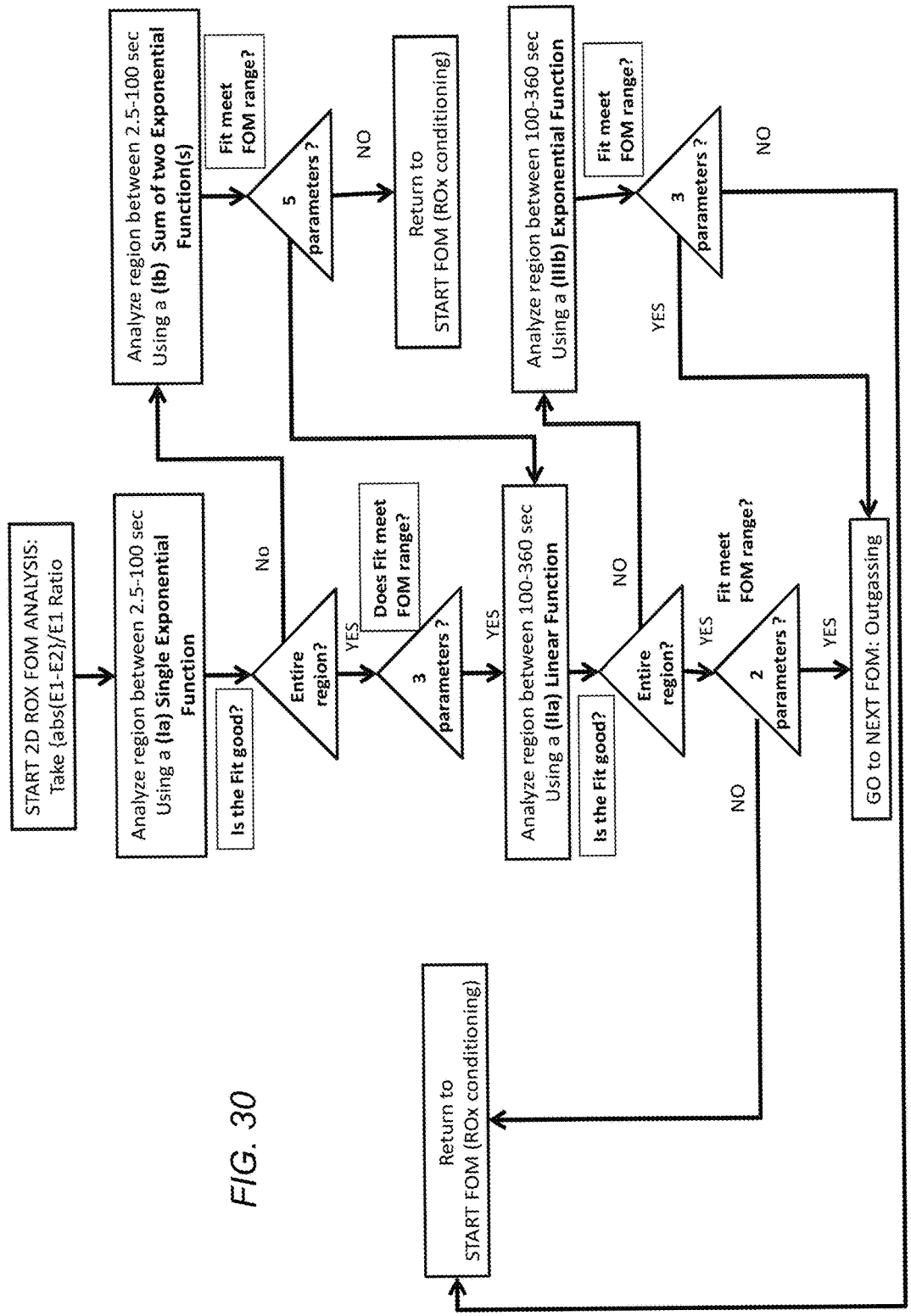
FIG. 30 depicts a flow chart for an example method for two-dimensional ROx Figures of Merit analysis.

FIG. 30 depicts a flow chart for an example method for two-dimensional ROx Figures of Merit analysis. The method may be executed as part of a larger routine or subroutine, such as the method shown in FIG. 18, or may be executed independently. In some embodiments, following the completion of this method, an additional method may be executed, for example, the method shown in FIG. 35. This method or similar methods may be used to calculate FOM values for a sample transfer routine.

Figure 31:
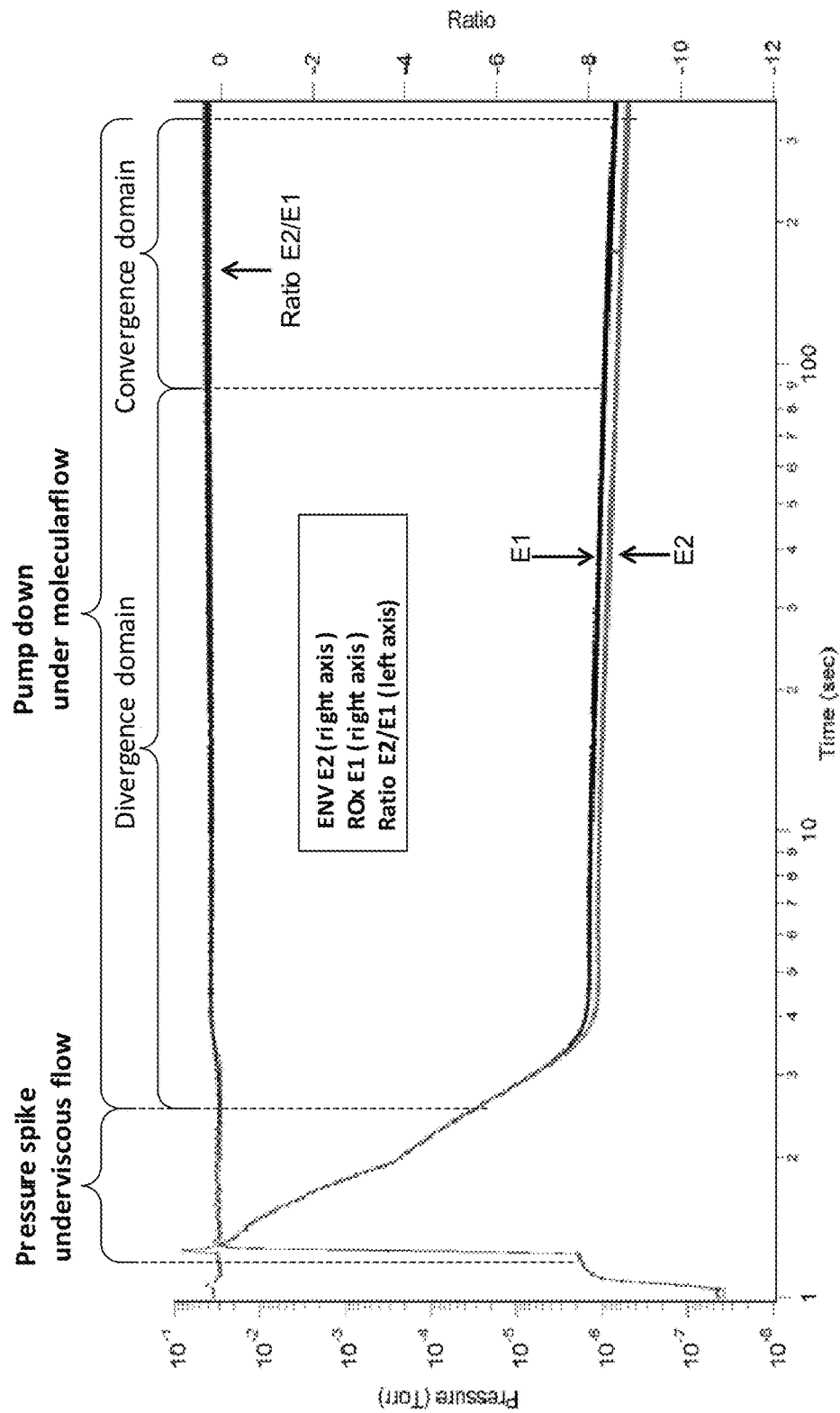
FIG. 31 depicts an example plot of example pressure spike and pump down vs. time curves acquired during an environment routine and used to calculate two-dimensional environment Figures of Merit.

FIG. 31 depicts an example plot of example pressure spike and pump down vs. time curves acquired during an environment routine and used to calculate two-dimensional environment Figures of Merit. Within the molecular flow region, the pump down ratio, {absolute (E1−E2)}/E1, vs. time is divided into two domains. E2 initially sharply diverges from E1 between 2.5 to 5 seconds and then reaches at steady state between 5-100 seconds. This time domain is labeled the divergence domain. From 100 to 360 seconds, both E1 and E2 are slowly converging as the buffer and load lock chambers are pumping down to the baseline pressure, e.g., $1\times10^{-7}$ Torr. This region is labeled as the convergence domain.

Figure 32:
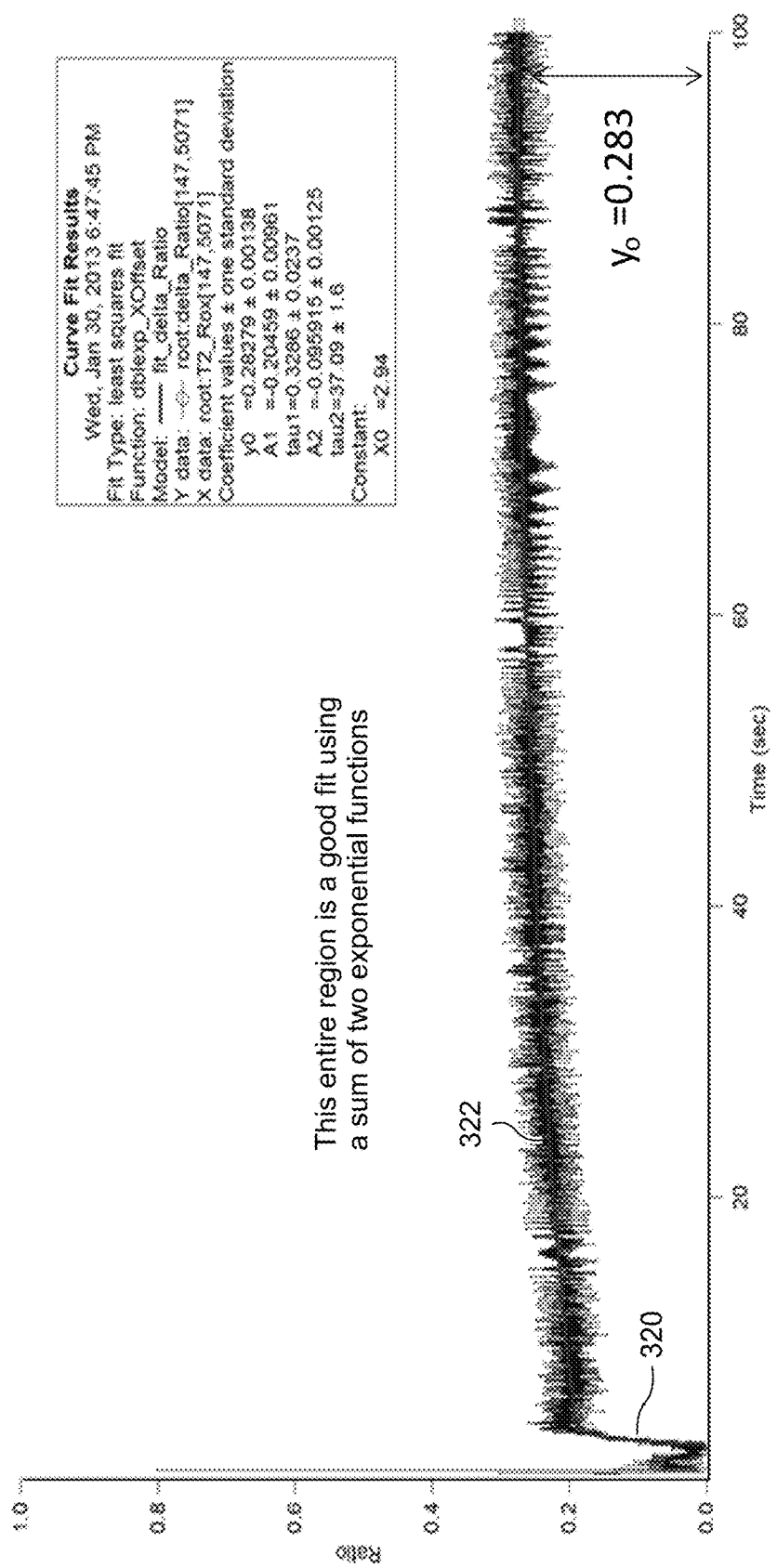
FIG. 32 depicts an example plot of an example curve fit of a ratio curve at a divergence domain using a sum of two exponential functions.
Figure 33:
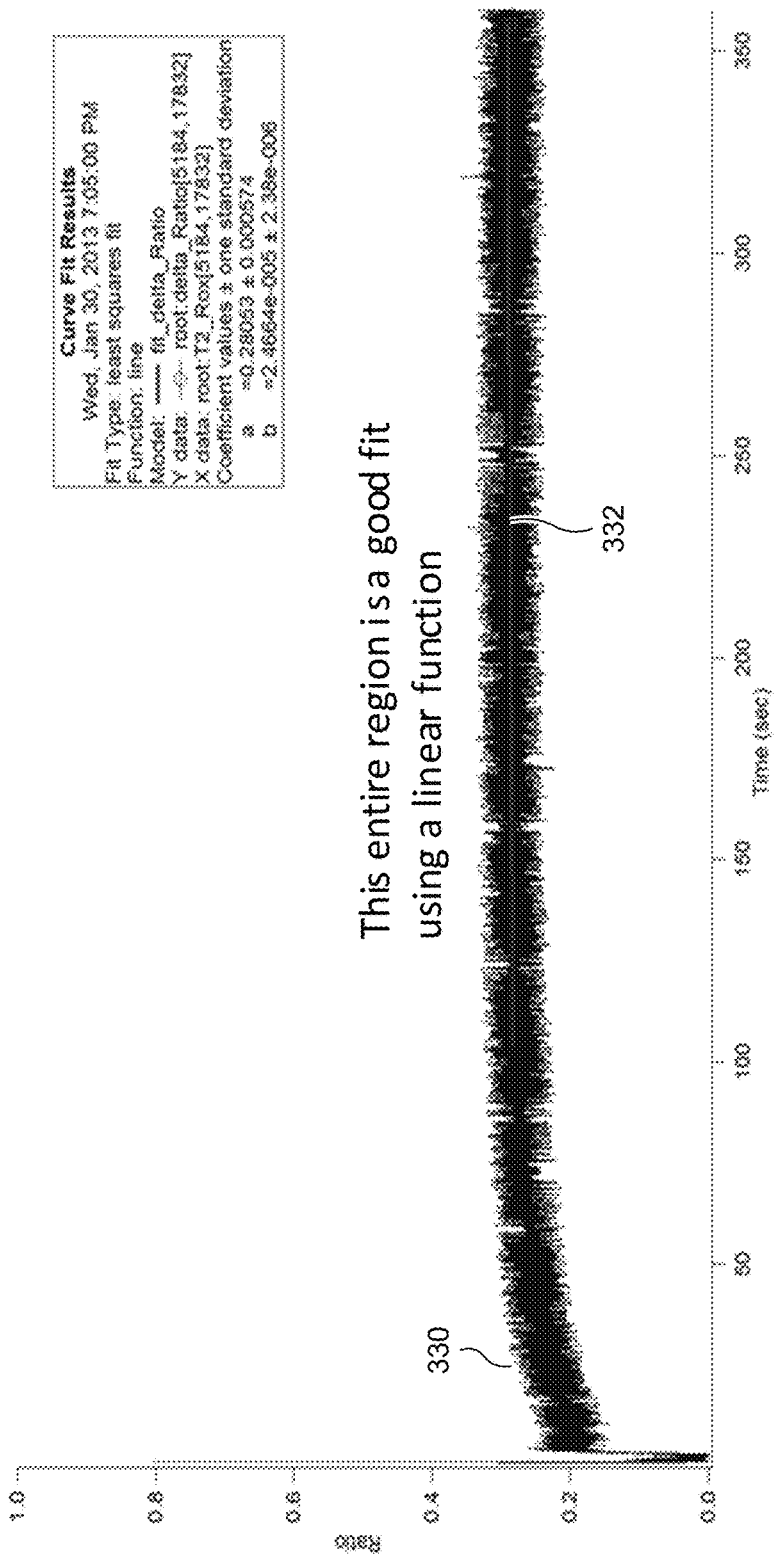
FIG. 33 depicts an example plot of an example curve fit of a ratio curve at a convergence domain using a linear function.

FIGS. 32-33 show example plots of example curve fits of ratio curves as described above. FIG. 32 depicts an example plot of an example curve fit of a ratio curve at a divergence domain using a sum of two exponential functions (experimental ratio 320 vs. sum of two exponential equations fit 322). The sum of two exponential functions fits the ratio curve at the divergence domain for this example. This curve fit maybe used to calculate environmental pumping FOM values between 2.8 and 100 seconds. FIG. 33 depicts an example plot of an example curve fit of a ratio curve at a convergence domain using a linear function (experimental ratio 320 vs. linear equation fit 322). The linear function fits the ratio curve at the convergence domain for this example. This curve fit maybe used to calculate environmental pumping FOM values between 100 and 360 seconds.

Table 6 depicts a summary of the curve fits of the ratio curve at the divergence and convergence domains as depicted in FIGS. 32-33. The curve fits may be used to calculate six FOM values for environment pumping through a method of quality control, for example through a method of statistical processing control (SPC).

TABLE 6

| Domain | FOM | Value | 1 sigma standard deviation |
|---|---|---|---|
| Divergence | y0 | 0.487 | ±8.4e−5 |
| | A1 | −0.36 | ±0.0018 |
| | tau1 | 1.21 | ±0.01 |
| | A2 | −0.1 | ±0.0004 |
| | tau2 | 7.4 | ±0.1 |
| Convergence | a (intercept) | 0.509 | ±1.2e−04 |
| | b (rate) | −2.3E−04 | ±5.4E−07 |

Figure 34:
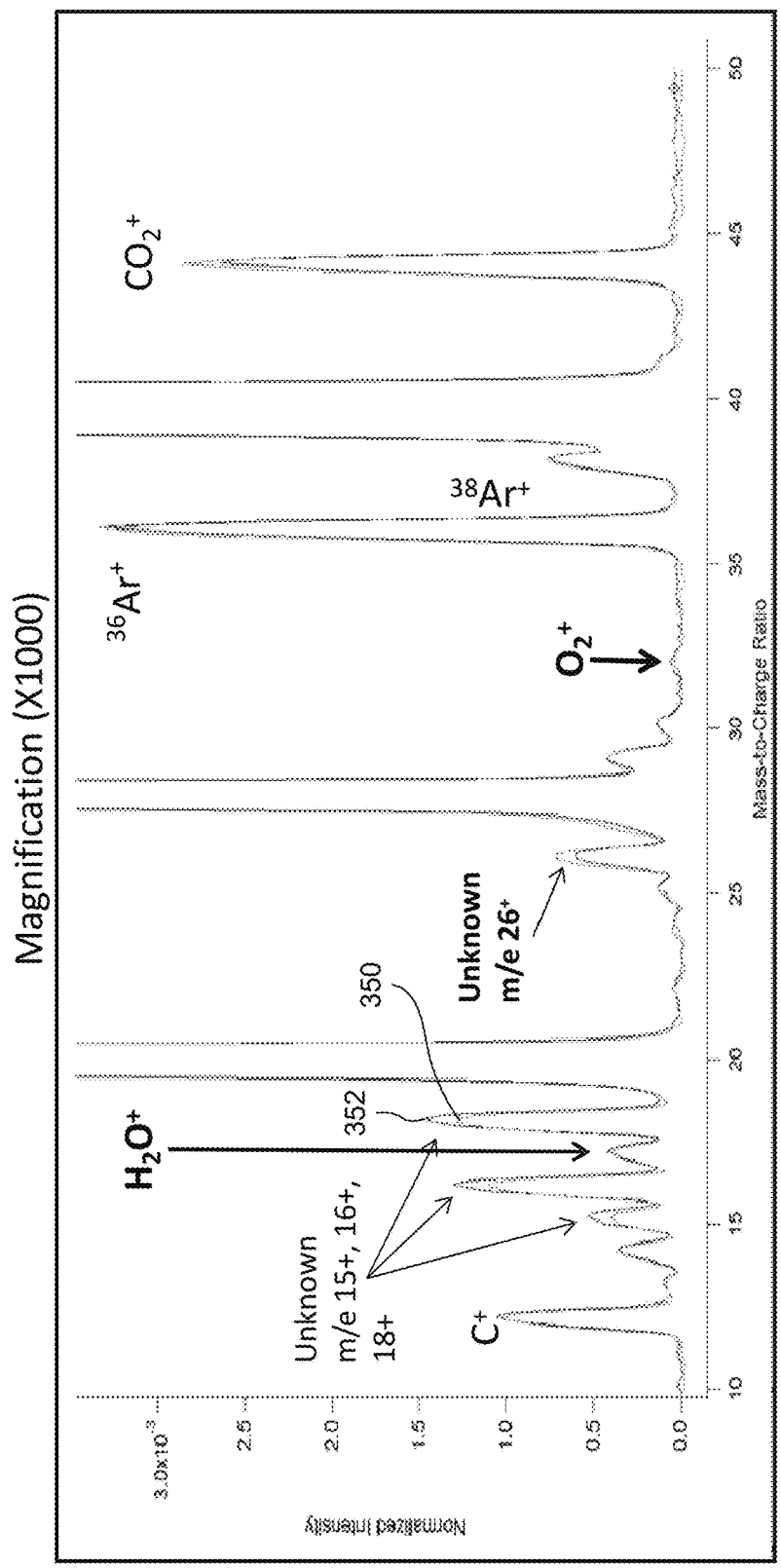
FIG. 34 depicts an example plot of normalized residual gas analysis Figures of Merit at 1000× magnification.

FIG. 34 depicts an example plot of normalized residual gas analysis Figures of Merit at 1000× magnification. At 1000 fold magnification, trace contaminants can be observed, including $C^+$, $H_2O^+$, $O_2^{+38}Ar^+$, as well as unidentifiable masses m/e $15^+$, $16^+$, $18^+$ and $26^+$. In this example, trace contaminants are detected for the glove box 350 including m/e 26+ and CO2+, and trace contaminants are detected for ROx 352, including m/e $15^+$, $16^+$ and $17^+$. For some applications, these contaminants may be at acceptable levels. Trace levels of water and oxygen are shown at equivalent levels in both the ROx and the glove box. Thus, this comparison demonstrates the ability of ROx to transfer samples under Argon with equivalent trace levels of oxidants compared to a glove box.

Figure 35:
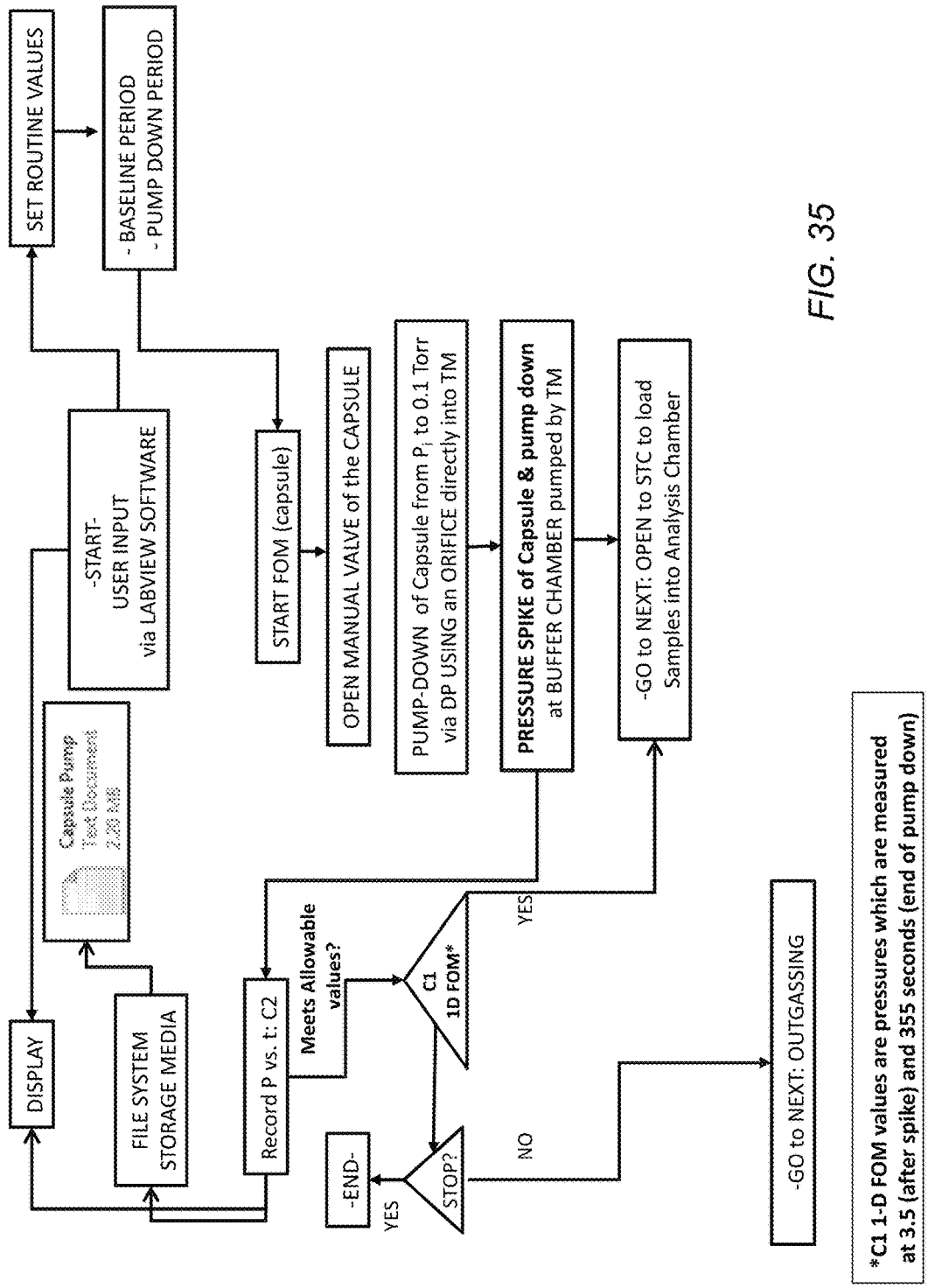
FIG. 35 depicts a flow chart for an example method for evaluating capsule pumping to test a sample capsule and samples enclosed therein.

FIG. 35 depicts a flow chart for an example method for evaluating capsule pumping to test a sample capsule and samples enclosed therein. The method may be executed as part of a larger routine or subroutine, such as the method shown in FIG. 18, or may be executed independently. In some embodiments, following the completion of this method, an additional method may be executed, for example, the method shown in FIG. 40. This method or similar methods may be used to calculate FOM values for a sample transfer routine.

Figure 36:
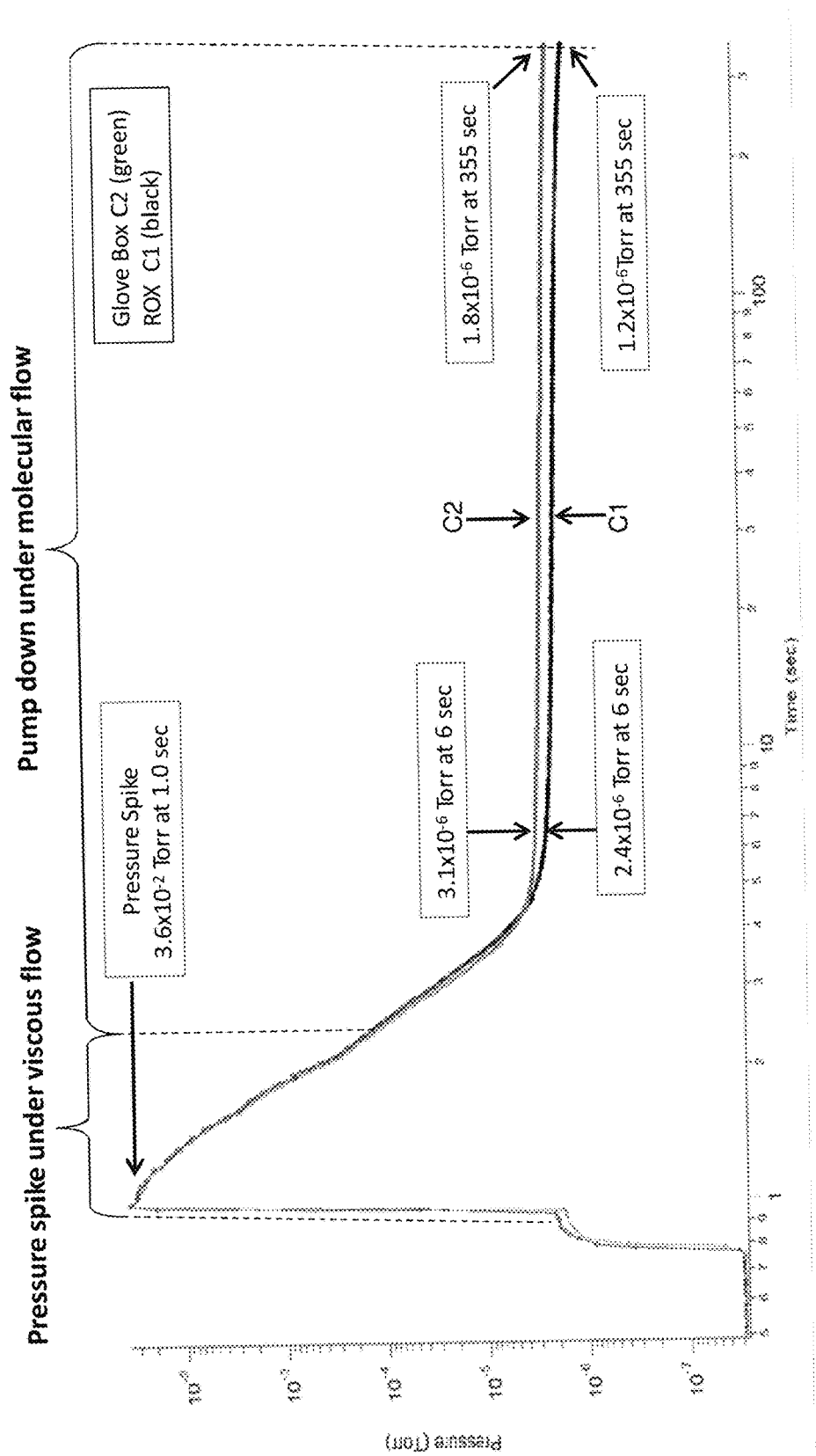
FIG. 36 depicts an example plot of two example pressure spike and pump down vs. time curves acquired with ROx Capsule and Glove box capsule routines and one-dimensional Figures of Merit.

FIG. 36 depicts an example plot of two example pressure spike and pump down vs. time curves acquired with ROx Capsule and Glove box routines and one-dimensional Figures of Merit. Using the pressure spikes as a time reference peak, the pump down curves, C1 and C2, are overlapped and plotted against time as the independent variable. The magnitude of these pressure spike (pressure 2.7×10-2 Torr) are identical since the gas flow is under viscous flow while the pump down region is under molecular flow (pressure<1× 10-5 Torr) after ~2.5 seconds. 1-D FOM for C1 & C2 are pressure values measured at 6 and 355 seconds.

Table 7 depicts a summary of the 1-dimensional FOMs for capsule pumping based on the pump down curves depicted in FIG. 36. The Ratio FOM is set equal to [absolute (C1−C2)]/C1. At t=3.5 and t=355 seconds, the ratio values may be assigned as 1-dimensional FOMs for capsule pumping.

TABLE 7

| | Time (sec) | |
|---|---|---|
| Curve | 6 | 355 |
| C1 ROx (Torr) | 3.10E−06 | 1.80E−06 |
| C2 Glove Box (Torr) | 2.4E−06 | 1.20E−06 |
| Ratio FOM [absolute (C1 − C2)]/C1 | 0.23 | 0.33 |

Figure 37:
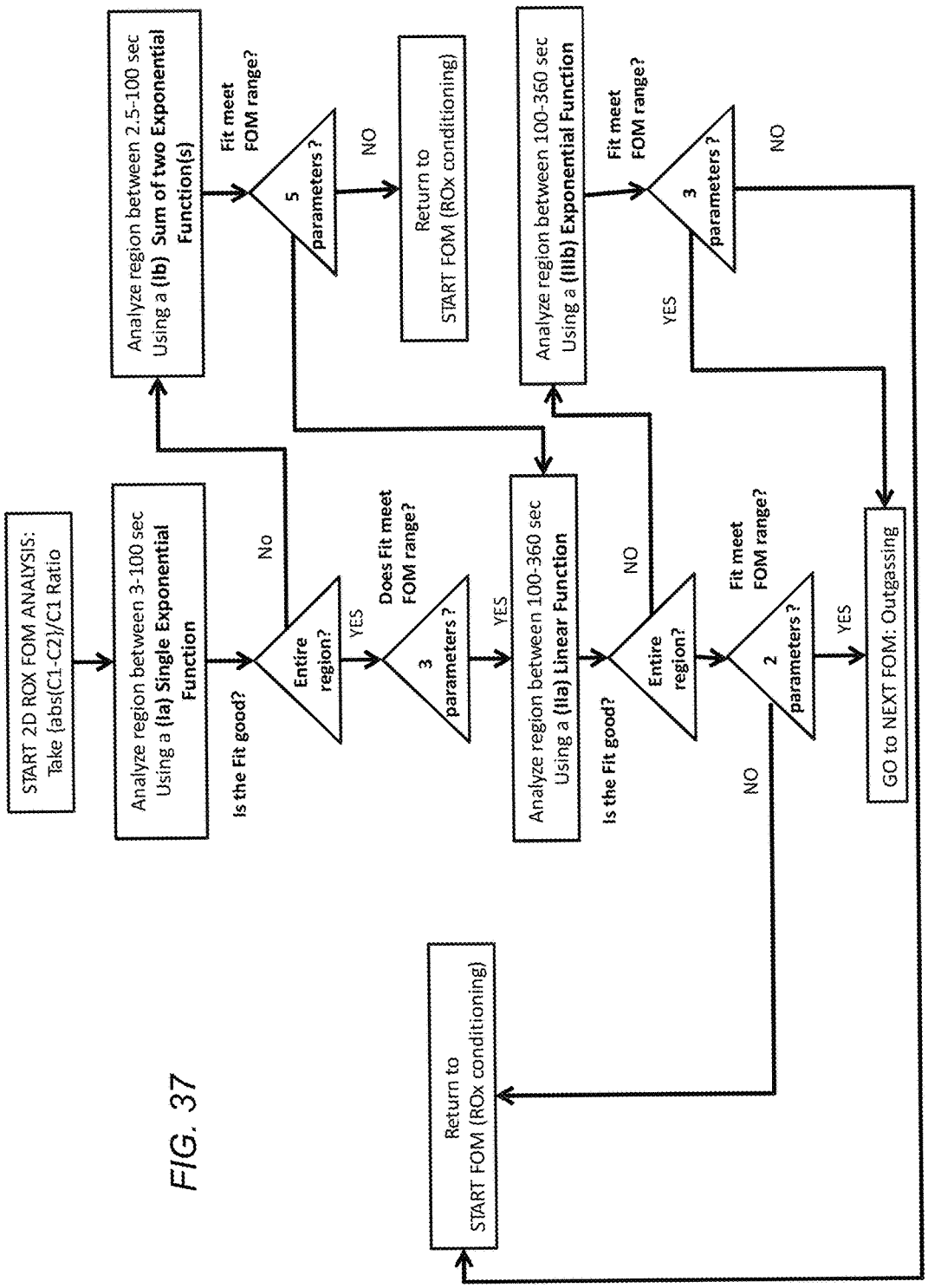
FIG. 37 depicts a flow chart for an example method for two-dimensional ROx Figures of Merit analysis.

FIG. 37 depicts a flow chart for an example method for two-dimensional ROx Figures of Merit analysis. The method may be executed as part of a larger routine or subroutine, such as the method shown in FIG. 18, or may be executed independently. In some embodiments, following the completion of this method, an additional method may be executed, for example, the method shown in FIG. 40. This method or similar methods may be used to calculate FOM values for a sample transfer routine.

Figure 38:
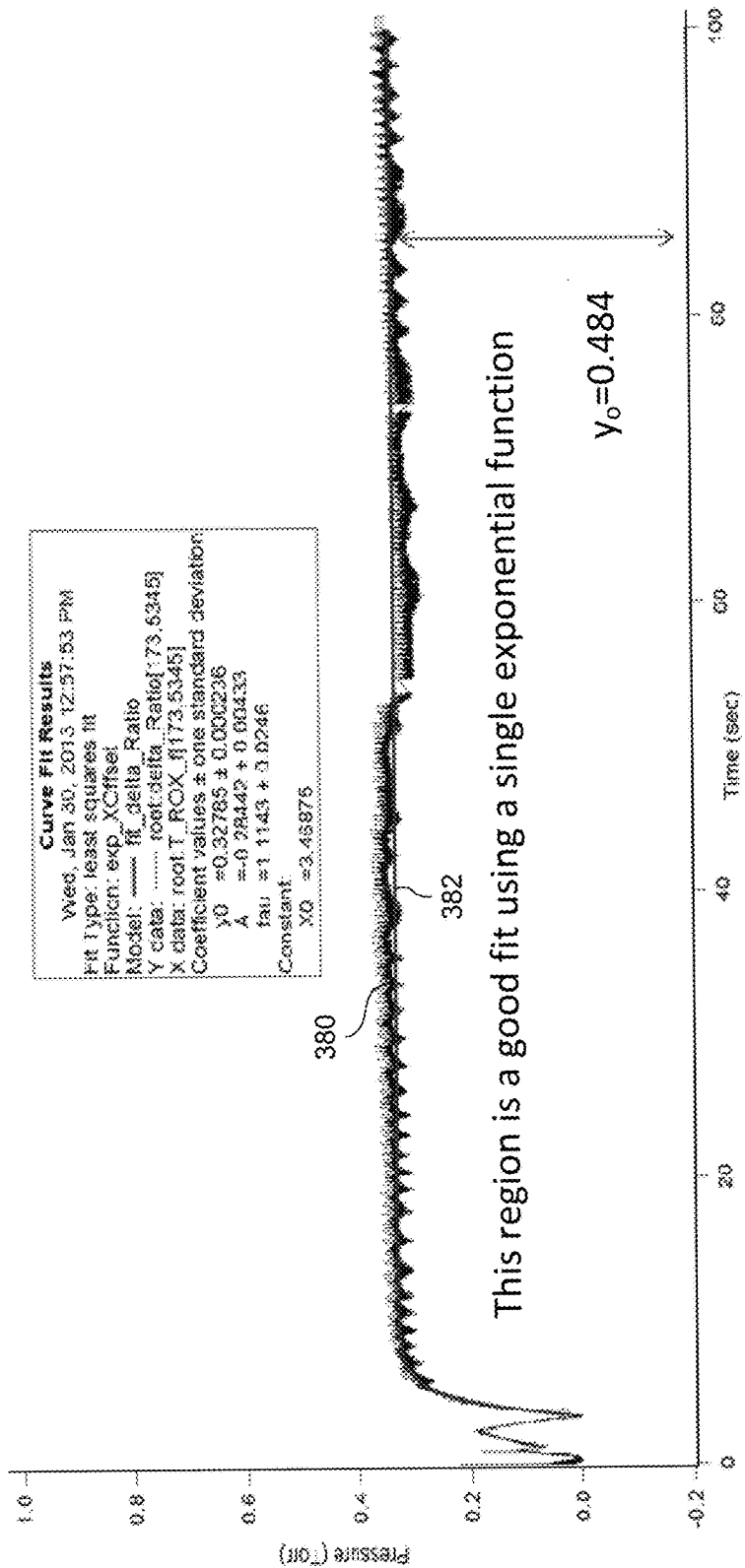
FIG. 38 depicts an example plot of an example curve fit of a ratio curve at a divergence domain using a single exponential function.
Figure 39:
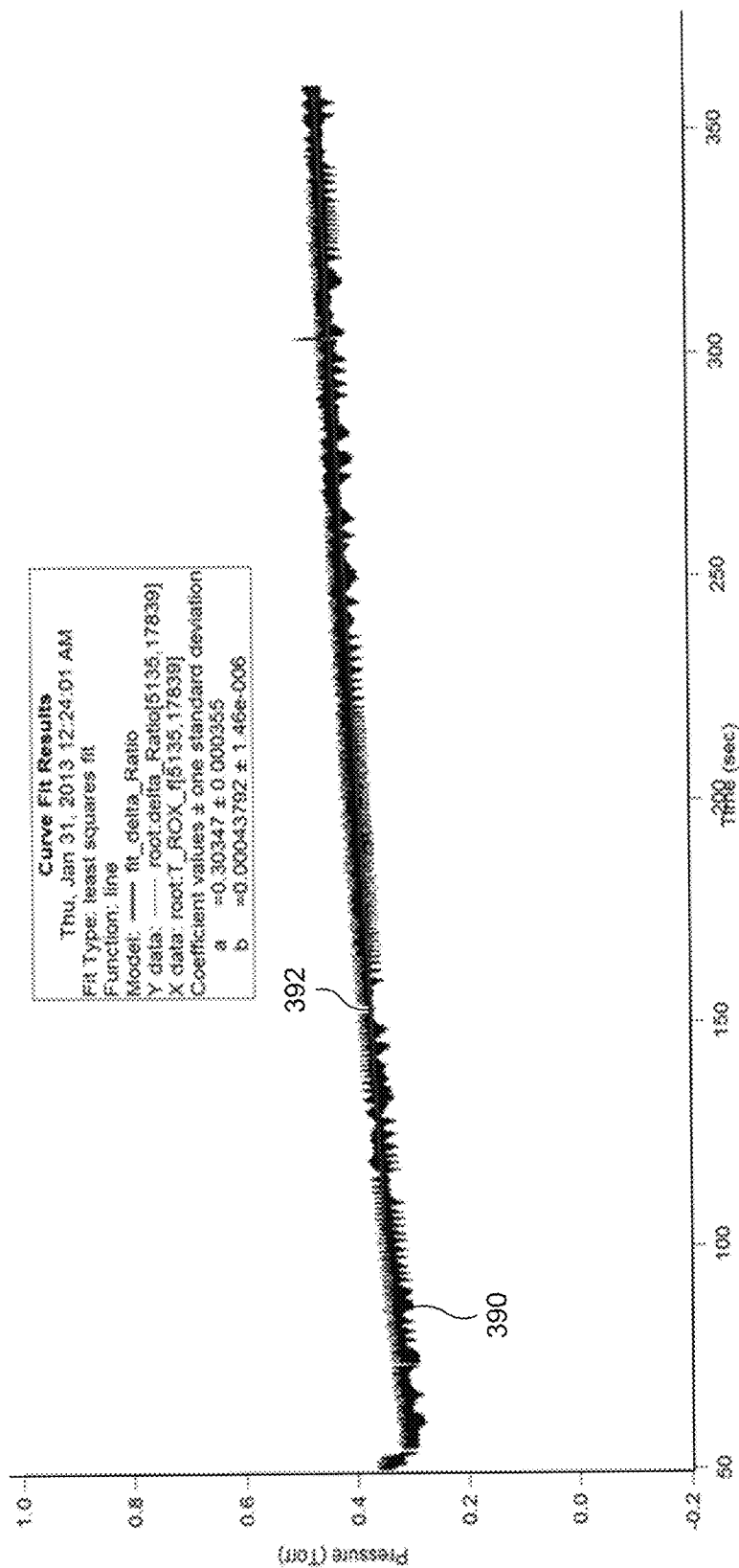
FIG. 39 depicts an example plot of an example curve fit of a ratio curve at a convergence domain using a linear function.

FIGS. 38-39 show example plots of example curve fits of ratio curves as described above. FIG. 38 depicts an example plot of an example curve fit of a ratio curve at a divergence domain using a single exponential function (experimental ratio 380 vs. single exponential equation fit 382). The single exponential function fits the ratio curve at the divergence domain for this example. This curve fit maybe used to calculate capsule pumping FOM values between 3.4 and 100 seconds. FIG. 39 depicts an example plot of an example curve fit of a ratio curve at a convergence domain using a linear function (experimental ratio 390 vs. linear equation fit 392). The linear function fits the ratio curve at the convergence domain for this example. This curve fit maybe used to calculate capsule pumping FOM values between 100 and 360 seconds.

Table 8 depicts a summary of the curve fits of the ratio curve at the divergence and convergence domains as depicted in FIGS. 38-39. The curve fits may be used to calculate FOM values for capsule pumping through a method of quality control, for example through a method of statistical processing control (SPC).

TABLE 8

| Domain | FOM | Value | 1 sigma standard deviation |
|---|---|---|---|
| Divergence | y0 | 0.327 | ±2.3e−4 |
| | A1 | −0.28 | ±0.004 |
| | tau1 | 1.11 | ±0.01 |
| | A2 | — | — |
| | tau2 | — | — |
| Convergence | a (intercept) | 0.303 | ±3.6e−04 |
| | b (rate) | 4.4E−04 | ±1.4E−06 |

Figure 40:
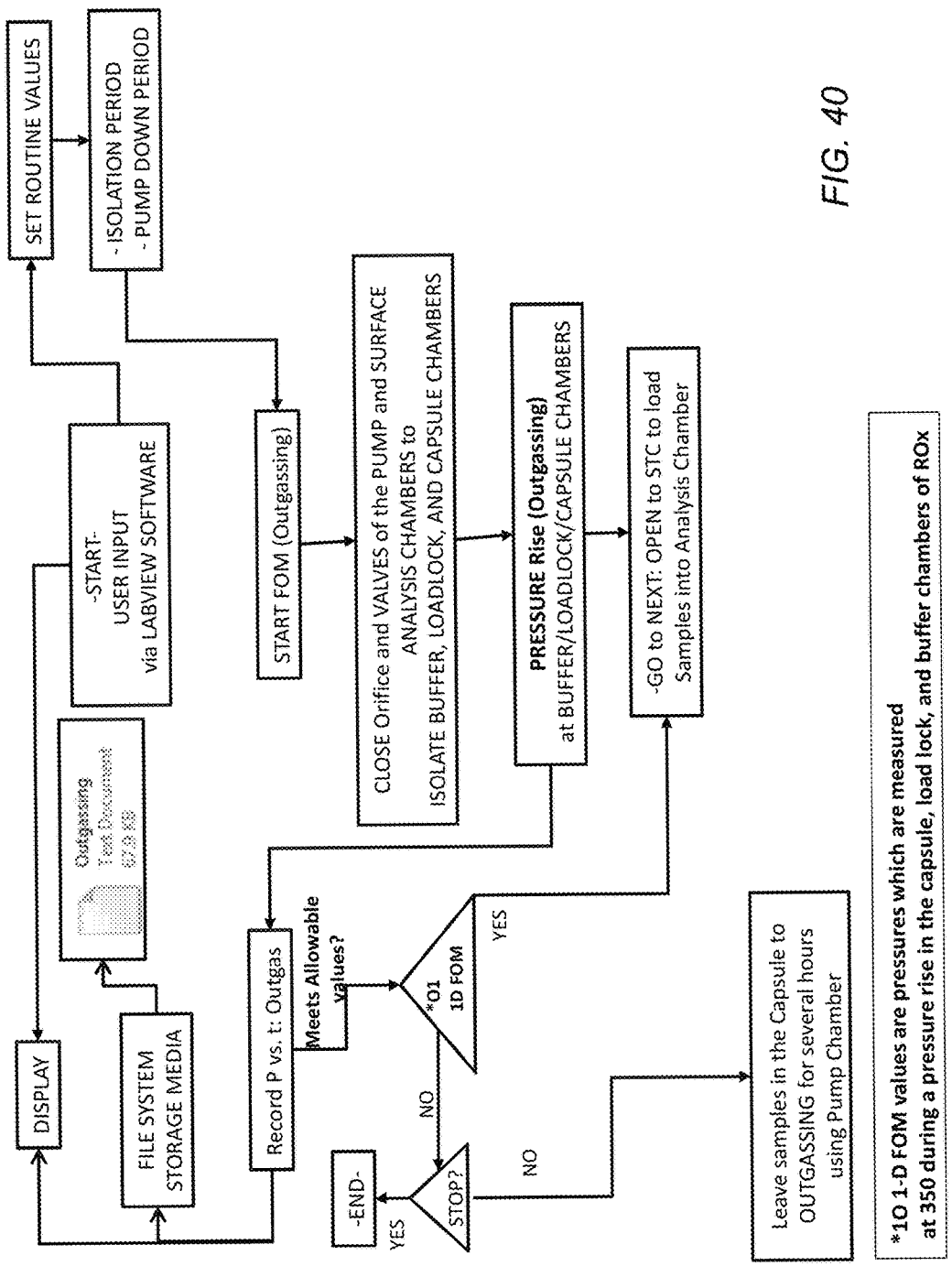
FIG. 40 depicts a flow chart for an example method for evaluating outgassing to test pressure rise vs. time curves due to outgassing after exposure to Argon at 850 Torr.

FIG. 40 depicts a flow chart for an example method for evaluating outgassing to test pressure rise vs. time curves due to outgassing after exposure to Argon at 850 Torr. The method may be executed as part of a larger routine or subroutine, such as the method shown in FIG. 18, or may be executed independently. In some embodiments, following the completion of this method, an additional method may be executed, for example, a method for opening the sample transfer capsule to load samples into an analysis chamber under UHV. This method or similar methods may be used to calculate FOM values for a sample transfer routine.

Figures 41A, 41B:
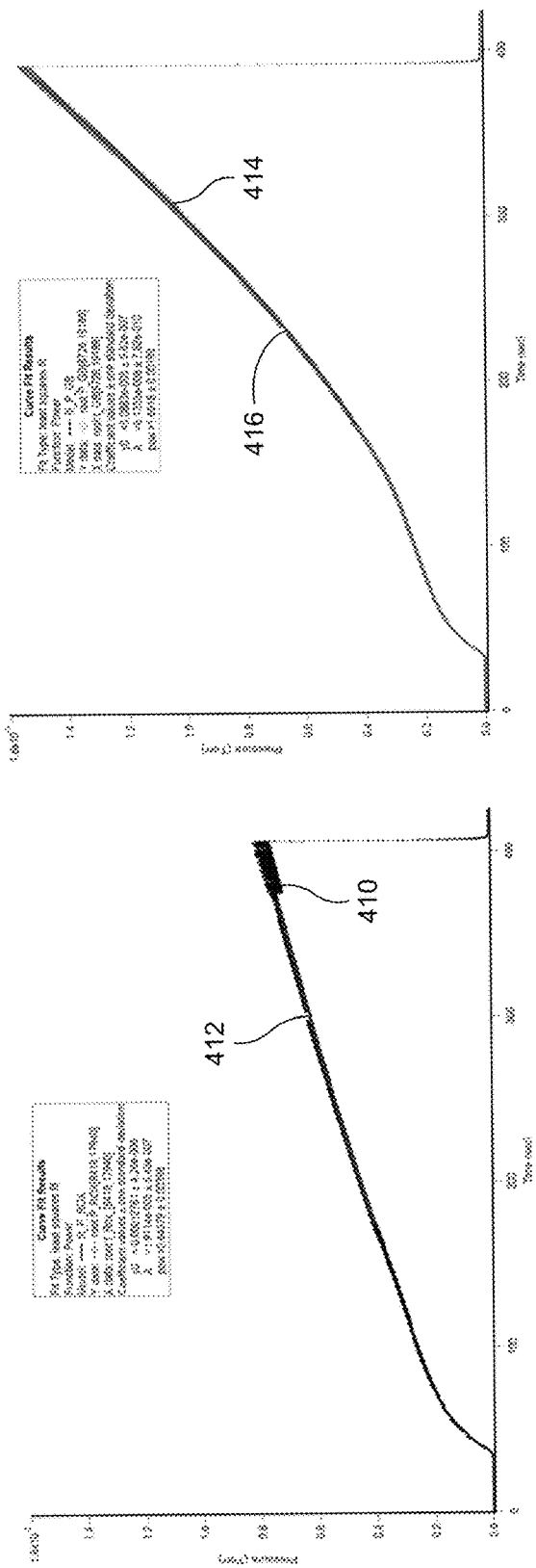
FIG. 41A an example plot of the curve fit of an example pressure vs. time curve for ROx.
FIG. 41B an example plot of the curve fit of an example pressure vs. time curve for a Glove Box.

FIGS. 41A and 41B show example curve fit plots using power functions that may be used to calculate outgassing FOM values between 175 and 350 seconds. FIG. 41A an example plot of the curve fit of an example pressure vs. time curve for ROx (experimental ratio 410 vs. power equation fit 412). FIG. 41B an example plot of the curve fit of an example pressure vs. time curve for a Glove Box (experimental ratio 414 vs. power equation fit 416). In both plots, the power equation fits the experimental ratios derived for outgassing.

Figure 42:
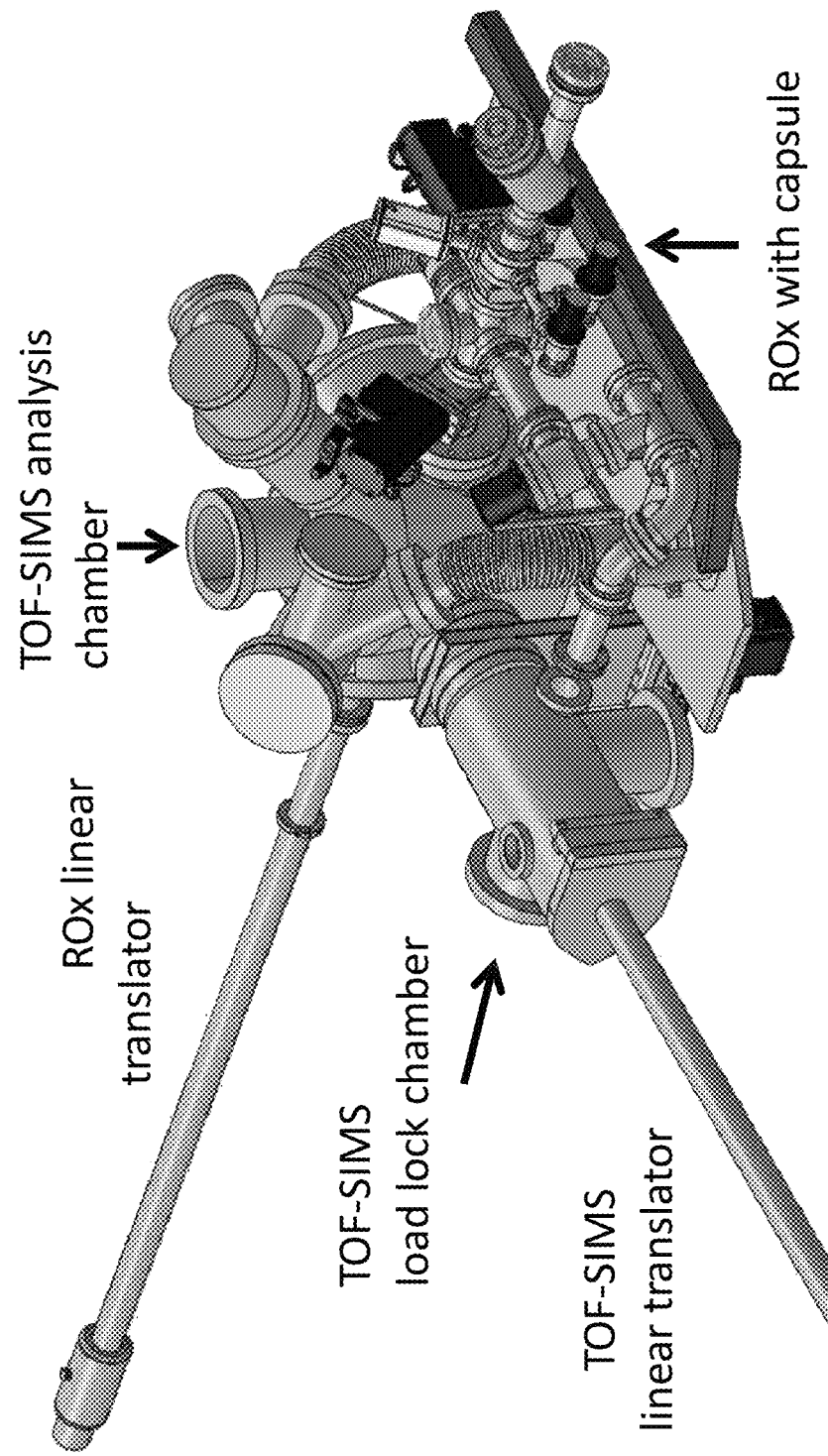
FIG. 42 depicts a schematic diagram of an example ROx installation design as a lock on a surface analysis chamber.

FIG. 42 depicts an example of an installation design for a ROx interface. FIG. 42 depicts a schematic diagram of an example ROx installation design as a lock on a surface analysis chamber. In this example, the surface analysis chamber is a time of flight secondary ion mass spectrometer (Tof-SIMS) analysis chamber. To install ROx on a Tof-SEMS analysis chamber, the ROx interface was redesigned to accommodate the space constraints, vibration limitations, and protect the vacuum integrity of the TOF-SEMS analysis chamber. The pumps of the ToF-SEMS for the load lock may be used to evacuate the interface and maintain vacuum on the order of $1\times10^{-8}$ Torr.

FIGS. 43A-D depict data showing how installation of ROx may be used to reduce the oxidation of samples at the Nano scale. A first case study was performed evaluating the growth of native oxide on a silicon surface, in this example a commercial silicon wafer, as measured by XPS. A first experiment was performed comparing the oxidation of silicon in ambient air and under vacuum for 6 hours following the etching of silicon oxide. A cleaned silicon with native silicon oxide was included for comparison. A second experiment was performed evaluating the oxidation of silicon under vacuum, under 850 Torr of Argon in a glove box, and under 850 Torr of Argon in ROx for six hours following the etching of silicon oxide. A cleaned silicon with native silicon oxide was included for comparison. In the second experiment, Argon purity was 99.9995% with less than 0.5 ppm of water and molecular oxygen.

FIGS. 43A-D depicts an example set of plots depicting the oxidation of a crystalline silicon wafer. XPS spectra are shown for the oxidation of Si in air (43A-B) and ~850 Torr of Argon (43C-D). The Si 2p transition clearly depicts two oxidation states of Si substrate 460 (99.7 eV) and silicon oxide 462 (102 eV). Compared to native silicon oxide 464, oxidation of an etched silicon was 55% in air and ~10% in Argon. Both (A) ROX 466 and (B) glove box 468 showed similar oxidation rates for silicon.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for transferring samples in a controlled environment, comprising:
   a sample container configured to convey a sample from a first device to a second device, wherein the first device is under pressure and the second device is under vacuum, wherein the second device comprises:
      a load chamber configured to accept the sample from the sample container;
      a pump chamber coupled to the load chamber using a conduit, wherein the pump chamber is in fluid communication with the load chamber via the conduit during use;
      a high vacuum pump coupled to the pump chamber;
      a vacuum pump coupled to the pump chamber through the high vacuum pump in sequence;
      an orifice sized to restrict the flow of fluids through the conduit coupling the pump chamber to the load chamber, wherein the orifice is configured to allow for a transition from a viscous into a molecular flow using differential pumping, and wherein the second device is configured to monitor a pressure spike within a portion of the second device.

2. The system of claim 1, wherein the orifice comprises a plurality of orifices.

3. The system of claim 1, wherein the orifice comprises a plurality of orifices, wherein at least some of the plurality of orifices are in series.

4. The system of claim 1, wherein the orifice comprises a variably sized orifice.

5. The system of claim 1, wherein the orifice comprises a variably size orifice, wherein the variably size orifice is remotely controlled.

6. The system of claim 1, wherein the system is configured to allow for a transition from a viscous into a molecular flow, without a power interruption and/or isolation of the high vacuum pump.

7. The system of claim 1, wherein the system is configured to achieve differential pumping.

8. The system of claim 1, wherein the first device comprises a contained inert atmosphere.

9. The system of claim 1, wherein the first device comprises a contained inert atmosphere, wherein the inert atmosphere is comprises a pressure greater than an atmospheric pressure outside of the first device.

10. The system of claim 1, wherein the sample container is positionable in the load chamber.

11. A system for transferring samples in a controlled environment, comprising:
    a sample container configured to convey a sample from a first device to a second device, wherein the first device is under pressure and the second device is under vacuum, wherein the second device comprises:

a load chamber configured to accept the sample from the sample container;

a vacuum pump coupled to the load chamber using a conduit, wherein the vacuum pump is in fluid communication with the load chamber via the conduit during use; and a variable orifice sized to restrict the flow of fluids through the conduit coupling the vacuum pump to the load chamber, wherein the orifice is configured to allow for a transition from a viscous into a molecular flow using differential pumping, and wherein the second device is configured to monitor a pressure spike within a portion of the second device.

12. The system of claim 11, wherein the variable orifice comprises a plurality variably size orifices.

13. The system of claim 11, wherein the pressure spike is tunable.

* * * * *